US010618935B2

(12) United States Patent
Ko et al.

(10) Patent No.: US 10,618,935 B2
(45) Date of Patent: *Apr. 14, 2020

(54) ANTIBODY-DRUG CONJUGATE (ADC) AND METHOD FOR FORMING THE SAME

(71) Applicant: Industrial Technology Research Institute, Hsinchu (TW)

(72) Inventors: Yi-Ju Ko, Taipei (TW); Jheng-Sian Li, Xiluo Township (TW); Maggie Lu, Zhudong Township (TW); On Lee, Hsinchu (TW); Ping-Fu Cheng, Taipei (TW); Chun-Min Liu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 388 days.

This patent is subject to a terminal disclaimer.

(21) Appl. No.: 15/341,834

(22) Filed: Nov. 2, 2016

(65) Prior Publication Data

US 2017/0119902 A1    May 4, 2017

Related U.S. Application Data

(60) Provisional application No. 62/250,107, filed on Nov. 3, 2015.

(51) Int. Cl.
| | | |
|---|---|---|
| *A61K 47/68* | (2017.01) | |
| *C07K 1/10* | (2006.01) | |
| *C07K 7/02* | (2006.01) | |
| *C07K 5/02* | (2006.01) | |
| *A61K 47/55* | (2017.01) | |

(52) U.S. Cl.
CPC .............. *C07K 7/02* (2013.01); *A61K 47/551* (2017.08); *A61K 47/6817* (2017.08); *A61K 47/6889* (2017.08); *C07K 5/0207* (2013.01)

(58) Field of Classification Search
None
See application file for complete search history.

(56) References Cited

U.S. PATENT DOCUMENTS

| | | | |
|---|---|---|---|
| 7,091,186 B2 | 8/2006 | Senter et al. | |
| 7,659,241 B2 | 2/2010 | Senter et al. | |
| 7,989,434 B2 | 8/2011 | Feng | |
| 8,034,959 B2 | 10/2011 | Ng et al. | |
| 8,288,352 B2 | 10/2012 | Doronina et al. | |
| 8,343,928 B2 | 1/2013 | Doronina et al. | |
| 8,470,980 B2 | 6/2013 | Hutchinson et al. | |
| 8,609,105 B2 | 12/2013 | Senter et al. | |
| 8,703,714 B2 | 4/2014 | Doronina et al. | |
| 8,871,720 B2 | 10/2014 | Doronina et al. | |
| 8,877,706 B2 | 11/2014 | Li et al. | |
| 8,889,855 B2 | 11/2014 | Deng | |
| 8,906,376 B2 | 12/2014 | Senter et al. | |
| 9,062,094 B2 | 6/2015 | Rau et al. | |
| 2009/0318668 A1 | 12/2009 | Beusker et al. | |
| 2010/0062008 A1 | 3/2010 | Senter et al. | |
| 2011/0020343 A1 | 1/2011 | Senter et al. | |
| 2011/0027274 A1 | 2/2011 | Cheng et al. | |
| 2012/0107332 A1 | 5/2012 | Jeffrey | |
| 2012/0225089 A1 | 9/2012 | Bouchard et al. | |
| 2015/0017246 A1 | 1/2015 | Huang | |
| 2015/0044238 A1 | 2/2015 | Doronina et al. | |
| 2015/0110815 A1 | 4/2015 | Park et al. | |
| 2015/0165063 A1 | 6/2015 | Flygare et al. | |
| 2015/0299337 A1 | 10/2015 | Ochiai et al. | |
| 2016/0130356 A1 | 5/2016 | DeSander et al. | |

FOREIGN PATENT DOCUMENTS

| | | |
|---|---|---|
| CN | 101980725 A | 2/2011 |
| CN | 102973947 A | 3/2013 |
| CN | 101490087 A | 11/2013 |
| JP | 6-293795 A | 10/1994 |
| JP | 7-188285 A | 7/1995 |
| JP | 2006-500333 A | 1/2006 |
| JP | 2009-501800 A | 1/2009 |
| JP | 2014-521319 A | 8/2014 |
| JP | 2015-505850 A | 2/2015 |
| TW | 201515662 A | 5/2015 |
| TW | 201605481 A | 2/2016 |
| WO | WO 90/14844 A2 | 12/1990 |
| WO | WO 91/13904 A1 | 9/1991 |
| WO | WO 95/09864 A1 | 4/1995 |
| WO | WO 2004/010957 A2 | 2/2004 |

(Continued)

OTHER PUBLICATIONS

Vippagunta et al. "Crystalline Solids," Advanced Drug Delivery Reviews, 2001, 48, pp. 11 and 18) (Year: 2001).*
Braga et al.; Stuct. Bond. 2009, 132, 25-50, specifically, p. 27, 3rd paragraph, p. 47, last paragraph (Year: 2009).*
Rudikoff et al. (PNAS USA, 1982, 79: 1979-1983) (Year: 1982).*
Coleman et al. (Research in Immunology, 1994; 145(1): 33-36) (Year: 1994).*
Abaza et al. (Journal of Protein Chemistry, vol. 11, No. 5, 1992, pp. 433-444 (Year: 1992).*
Gussow et al. (1991, Methods in Enzymology 203:99-121) (Year: 1991).*
Ibragimova and Wade (Biophysical Journal, Oct. 1999, vol. 77, pp. 2191-2198) (Year: 1999).*

(Continued)

*Primary Examiner* — Mark Halvorson
*Assistant Examiner* — Kauser M Akhoon
(74) *Attorney, Agent, or Firm* — Birch, Stewart, Kolasch & Birch, LLP

(57) ABSTRACT

An antibody-drug conjugate (ADC) of formula (I) or a pharmaceutically acceptable salt or solvate thereof is provided. In formula (I), p is an integer ranging from 1 to 26, A is an antibody, and -(L-D) is a linker-drug unit. L is a linker unit having a glycopeptide, and D is a drug unit. The antibody is conjugated to the linker unit through a cysteine residue of the antibody. A method for forming an antibody-drug conjugate (ADC) is also provided.

$A\text{-}(L\text{-}D)_p$          (I)

10 Claims, 25 Drawing Sheets

(56) References Cited

FOREIGN PATENT DOCUMENTS

| WO | WO 2005/082023 A2 | 9/2005 |
|---|---|---|
| WO | WO 2005/112919 A2 | 12/2005 |
| WO | WO 2006/060533 A2 | 6/2006 |
| WO | WO 2006/132670 A2 | 12/2006 |
| WO | WO 2007/008603 A1 | 1/2007 |
| WO | WO 2007/008848 A2 | 1/2007 |
| WO | WO 2007/089149 A2 | 8/2007 |
| WO | WO 2008/034124 A2 | 3/2008 |
| WO | WO 2008/083312 A2 | 7/2008 |
| WO | WO 2008/103693 A2 | 8/2008 |
| WO | WO 2009/017394 A1 | 2/2009 |
| WO | WO 2009/099741 A1 | 8/2009 |
| WO | WO 2010/009124 A2 | 1/2010 |
| WO | WO 2010/062171 A2 | 6/2010 |
| WO | WO 2011/130598 A1 | 10/2011 |
| WO | WO 2011/133039 A2 | 10/2011 |
| WO | WO 2012/113847 A1 | 8/2012 |
| WO | WO 2012/166560 A1 | 12/2012 |
| WO | 101573384 A | 2/2013 |
| WO | WO 2013/055990 A1 | 4/2013 |
| WO | WO 2013/068874 A1 | 5/2013 |
| WO | WO 2013/072813 A2 | 5/2013 |
| WO | WO 2013/122823 A1 | 8/2013 |
| WO | WO 2013/149946 A1 | 10/2013 |
| WO | WO 2013/149948 A1 | 10/2013 |
| WO | WO 2013/166155 A1 | 11/2013 |
| WO | WO 2013/173391 A1 | 11/2013 |
| WO | WO 2013/181597 A2 | 12/2013 |
| WO | WO 2013/185117 A1 | 12/2013 |
| WO | WO 2013/190292 A2 | 12/2013 |
| WO | WO 2013/192360 A1 | 12/2013 |
| WO | WO 2014/008375 A1 | 1/2014 |
| WO | WO 2014/064423 A1 | 5/2014 |
| WO | WO 2014/065661 A1 | 5/2014 |
| WO | WO 2014/067960 A2 | 5/2014 |
| WO | WO 2014/068443 A1 | 5/2014 |
| WO | WO 2014/072484 A1 | 5/2014 |
| WO | WO 2014/080251 A1 | 5/2014 |
| WO | WO 2014/088432 A1 | 6/2014 |
| WO | WO 2014/093379 A1 | 6/2014 |
| WO | WO 2014/094353 A1 | 6/2014 |
| WO | WO 2014/094354 A1 | 6/2014 |
| WO | WO 2014/100762 A1 | 6/2014 |
| WO | WO 2015/054659 A1 | 4/2015 |
| WO | WO 2015/123679 A1 | 8/2015 |

OTHER PUBLICATIONS

Doronina et al., "Development of potent monoclonal antibody auristatin conjugates for cancer therapy", Nature Biotechnology, Jul. 2003, vol. 21, pp. 778-784.
Doronina et al., "Novel Peptide Linkers for Highly Potent Antibody-Auristatin Conjugate", Bioconjugate Chemistry, 2008, vol. 19, pp. 1960-1963.
Sun et al., "Reduction-Alkylation Strategies for the Modification of Specific Monoclonal Antibody Disulfides", Bioconjugate Chemistry, 2005, vol. 16(5), pp. 1282-1290.
European Search Report for Appl. No. 16196898.7 dated Mar. 23, 2017.
McCombs, J.R., et al, "Antibody Drug Conjugates: Design and Selection of Linker, Payload and Conjugation Chemistry," The AAPS Journal, Mar. 2015, vol. 17, No. 2, pp. 339-351.
Taiwanese Office Action for Appl. No. 105135455 dated Feb. 6, 2018.
Japanese Decision to Grant a Patent for Application No. 2016-214926, dated Sep. 5, 2018.
Badescu et al., "Bridging Disulfides for Stable and Defined Antibody Drug Conjugates," Bioconjugate Chemistry, vol. 25, May 3, 2014, pp. 1124-1136.
Doronina et al., "Novel Peptide Linkers for Highly Potent Antibody-Auristatin Conjugate," Bioconjugate Chemistry, vol. 19, No. 10, 2008 (published online Sep. 20, 2008), pp. 1960-1963.
Dubowchik et al., "Cathepsin B-Sensitive Dipeptide Prodrugs. 1. A Model Study of Structural Requirements for Efficient Release of Doxorubicin," Bioorganic & Medicinal Chemistry Letters, vol. 8, 1998, pp. 3341-3346.
Extended European Search Report for Appl. No. 16196894.6 dated May 16, 2017.
Jeffrey et al., "Design, Synthesis, and in Vitro Evaluation of Dipeptide-Based Antibody Minor Groove Binder Conjugates," Journal of Medical Chemistry, vol. 48, No. 5, 2005 (Published on Web Feb. 5, 2005), pp. 1344-1358.
Jeffrey et al., "Dipeptide-based highly potent doxorubicin antibody conjugates," Bioorganic & Medicinal Chemistry Letters, vol. 16, 2006 (available online Nov. 3, 2005), pp. 358-362.
Liang et al., "Novel cathepsin B-sensitive paclitaxel conjugate: Higher water solubility, better efficacy and lower toxicity," Journal of Controlled Release, vol. 160, 2012 (available online Mar. 3, 2012), pp. 618-629.
Partial European Search Report for Appl. No. 16196894.6 dated Mar. 17, 2017.
Taiwanese Office Action and Search Report issued in Taiwanese Application No. 105135454 dated Aug. 9, 2017.
Toki et al., "Protease-Mediated Fragmentation of p-Amidobenzyl Ethers: A New Strategy for the Activation of Anticancer Prodrugs," Journal of Organic Chemistry, vol. 67, No. 6, 2002 (Published on Web Feb. 12, 2002), pp. 1866-1872.
Verma et al., "The cryptophycins as potent payloads for antibody drug conjugates," Bioorganic & Medicinal Chemistry Letters, vol. 25, 2015 (available online Jan. 2, 2015), pp. 864-868.
Industrial Technology Research Institute, "Smart Target Drug Delivery Technology And Application Development Project" (Year 103, December), Jan. 2015, [retrieved on Nov. 1, 2017], Retrieved from the Internet.
Japanese Office Action for Application No. 2016-214926 dated Dec. 14, 2017.
Japanese Office Action for Application No. 2016-215442 dated Dec. 20, 2017.

* cited by examiner

ANTIBODY-DRUG CONJUGATE (ADC) AND METHOD FOR FORMING THE SAME

CROSS REFERENCE TO RELATED APPLICATIONS

This application claims the benefit of U.S. Provisional Application No. 62/250,107, filed Nov. 3, 2015, the entirety of which is incorporated by reference herein.

TECHNICAL FIELD

The technical field relates to an antibody-drug conjugate (ADC) and a method for forming the same, and in particular it relates to an antibody-drug conjugate (ADC) including an antibody conjugated with a glycopeptide-containing linker-toxin and a method for forming the same.

BACKGROUND

Antibodies have high-degree identification abilities with respect to their corresponding antigens, and many cytotoxic drug molecules cannot be used for cancer therapy because they cannot selectively kill cancer cells. Therefore, the connection of antibodies and highly toxic drugs (such as toxins) becomes a highly selective and specific conjugated drug.

An antibody-drug conjugate (ADC) is composed of antibodies, linkers, and drugs (such as toxins). However, these toxins appear to be highly cytotoxic (IC50<1 nM) due to they have to be performed with high dose. One of the toxins commonly used in ADCs is auristatin derivative such as MMAE and MMAF.

One of the linkers commonly used in ADCs is MC-Val-Cit. Among these commonly used linkers, the MC-Val-Cit-PAB developed by Seattle Genetics is the most widely applied system. Toxins of ADCs are liberated by breaking the bonding linkage between linkers and toxins via cathepsin B. However, the linker system is poor aqueous solubility. It requires a high content, 20%, of organic solvent used as a co-solvent to dissolve the linker-toxin during the conjugation process of ADCs, so that the conjugation reaction can be completed in a homogeneous phase.

However, the above-mentioned introducing organic solvent may result in antibody degeneration or antibody aggregation, and further result in yield reduction or product failure of the ADCs. In addition, incomplete removal of organic solvent may potentially be one of the reasons that the final ADC products cannot pass quality control.

Therefore, the development of novel ADC drugs is a challenge in assisting human beings meet anti-cancer medical needs.

SUMMARY

The disclosure provides an antibody-drug conjugate (ADC) of formula (I) or a pharmaceutically acceptable salt or solvate thereof:

$$A\text{-}(L\text{-}D)_p \quad (I)$$

In formula (I), p is an integer ranging from 1 to 26, A is an antibody, and -(L-D) is a linker-drug unit. L is a linker unit having a glycopeptide, and D is a drug unit. The antibody is conjugated to the linker unit through a cysteine residue of the antibody.

The disclosure also provides a method for forming the above-mentioned antibody-drug conjugate (ADC). The method includes the steps of reacting an antibody and a reducing agent in a buffer to form a first solution, preparing a linker-drug unit in organic phase or aqueous phase to form a second solution, in which the linker has a glycopeptide, performing a conjugation process by mixing the first solution and the second solution to form a mixture solution, and purifying the mixture solution. The concentration of an organic solvent in the mixture solution is in a range of about 0% (v/v) to about 2% (v/v).

A detailed description is given in the following embodiments with reference to the accompanying drawings.

BRIEF DESCRIPTION OF THE DRAWINGS

The present invention may be more fully understood by reading the subsequent detailed description and examples with references made to the accompanying drawings, wherein.

DETAILED DESCRIPTION

Figure 1:
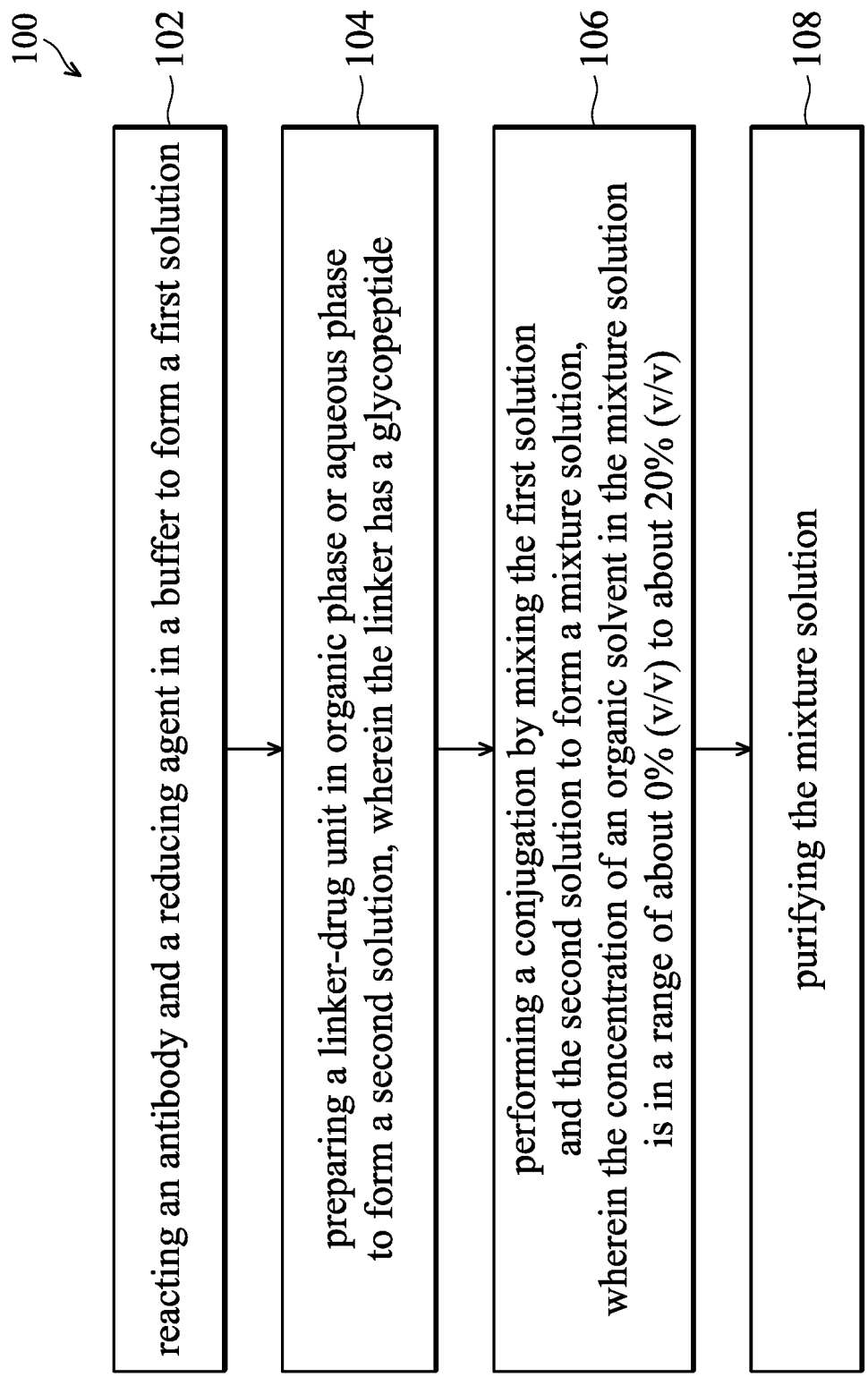
FIG. 1 is a flow diagram illustrating a method for forming an antibody-drug conjugate (ADC) in accordance with some embodiments of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

The present disclosure provides an ADC including a novel linker-toxin with increased aqueous solubility. During the conjugation process of the ADC, the use of an organic solvent is decreased or even avoided, thereby reducing the aggregation of the ADC and the problems resulted from the remaining organic solvent. Therefore, the stability of ADC is improved.

The said novel linker-toxins are designed to introduce sugar groups such as pentose (such as ribose, xylose or arabinose) and hexose (such as glycosamine or glucose) to dipeptide linkers, such as Val-Cit and Phe-Cit, which can be recognized by cathepsin B. In other words, the novel linker-toxins include a novel sugar amino acid-containing linker which is characterized as having a cathepsin B recognized dipeptide in its C-terminal and a high hydrophilic sugar amino acid unit in its N-terminal to improve the aqueous solubility of said linker or linker-containing substance. Both the carboxylic group in the C-terminal and the amino group in the N-terminal of the linker may be a linking point for attaching spacers, linkers, ligands, drugs, toxins, imaging molecules, antibodies, peptides or delivery molecules.

In the present disclosure, several antibodies and the sugar amino acid-containing linker-toxins are conjugated to form novel ADCs. In one embodiment, the present application provides an antibody-drug conjugate (ADC) of formula (I) or a pharmaceutically acceptable salt or solvate thereof.

A-(L-D)p      (I)

In formula (I), A represents an antibody. In some embodiments, the antibody can be a full-length antibody or an antibody fragment. In some embodiments, the antibody can be a chimeric antibody or a functionally active fragment thereof, a humanized antibody or a functionally active fragment thereof, a human antibody or a functionally active fragment thereof, or a mouse antibody or a functionally active fragment thereof. In other embodiments, the antibody can be an antibody from other species such as a rat antibody or a functionally active fragment thereof, a goat antibody or a functionally active fragment thereof, or a rabbit antibody or a functionally active fragment thereof. In some embodiments, the antibody is conjugated to the linker unit through a cysteine residue of the antibody. In some embodiments, the antibody may be a therapeutic antibody used for the treatment of tumor, chronic lymphocytic leukemia (CLL), or acute myeloid leukemia (AML). In certain embodiments, the antibody may include Herceptin, Erbitux, HLX-07, EG12014, anti-EpCAM Ab, IgG1, Rituximab, Ibritumomab tiuxetan, Tositumomab, Brentuximab vedotin, Alemtuzumab, IGN101, Adecatumumab, Labetuzumab, huA33, Pemtumomab, Oregovomab, CC49 (minretumomab), cG250, J591, MOv18, MORAb-003 (farletuzumab), 3F8, ch14.18, KW-2871, hu3S193, IgN311, Bevacizumab, IM-2C6, CDP791, Etaracizumab, Volociximab, Cetuximab, Panitumumab, Nimotuzumab, 806, Trastuzumab, Pertuzumab, MM-121, AMG 102, METMAB, SCH 900105, AVE1642, IMC-A12, MK-0646, R1507, CP 751871, KB004, IIIA4, Mapatumumab (HGS-ETR1), HGS-ETR2, CS-1008, Denosumab, Sibrotuzumab, F19, or 8106. However, it should be appreciated that the above antibodies are merely examples and the scope of the invention is not intended to be limited. As long as the inter-chain disulfide bonds in the antibody can be reduced to free thiols to be conjugated with linkers, the antibody can be used in the present disclosure.

In one embodiment, the antibody may be polyclonal antibodies or monoclonal antibodies. The antibody may be directed to a particular antigenic determinant, including for example a cancer cell antigen, a viral antigen, a microbial antigen, a protein, a peptide, a carbohydrate, a chemical, nucleic acid, or fragments thereof. Methods of producing polyclonal antibodies are known in the prior art. A monoclonal antibody (mAb) to an antigen-of-interest can be prepared using any technique known in the prior art. These include, but are not limited to, the hybridoma technique originally described by Köhler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). Such antibodies can be of any immunoglobulin class including IgG, IgM, IgE, IgA, and IgD and any subclass thereof. The hybridoma producing the mAbs for use in the disclosure may be cultivated in vitro or in vivo.

The monoclonal antibody can be, for example, a human monoclonal antibody, a humanized monoclonal antibody, an antibody fragment, or a chimeric antibody (e.g., a human-mouse antibody). Human monoclonal antibodies can be made by any of numerous techniques known in the prior art (e.g., Teng et al., 1983, Proc. Natl. Acad. Sci. USA 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the prior art. Traditional production of full-length bispecific antibodies is based on the coexpression of two immunoglobulin heavy chain-light chain pairs, where the two chains have different specificities (see, e.g., Milstein et al., 1983, Nature 305:537-

539; International Publication No. WO 93/08829, Traunecker et al., 1991, EMBO J. 10:3655-3659).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details of generating bispecific antibodies see, for example, Suresh et al., 1986, Methods in Enzymology 121:210; Rodrigues et al., 1993, J. Immunology 151:6954-6961; Carter et al., 1992, Bio/Technology 10:163-167; Carter et al., 1995, J. Hematotherapy 4:463-470; Merchant et al., 1998, Nature Biotechnology 16:677-681. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies may be derived either biologically (i.e., by cell fusion techniques) or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The antibody also can be a functionally active fragment, derivative or analog of an antibody that immunospecifically binds to a target antigen (e.g., a cancer antigen, a viral antigen, a microbial antigen, or other antibodies bound to cells or matrix). In this regard, "functionally active" means that the fragment, derivative or analog is able to recognize the same antigen that the antibody from which the fragment, derivative or analog is derived recognized. Specifically, in an exemplary embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences may be used in binding assays with the antigen by any binding assay method known in the prior art (e.g., the BIA core assay) (see, e.g., Kabat et al., 1991, Sequences of Proteins of Immunological Interest, Fifth Edition, National Institute of Health, Bethesda, Md.; Kabat et al., 1980, J. Immunology 125(3): 961-969).

Other useful antibodies include fragments of antibodies such as, but not limited to, F(ab')2 fragments, Fab fragments, Fab', Fv fragments and heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54).

Recombinant antibodies, such as chimeric and humanized monoclonal antibodies, comprising both human and non-human portions, which may be made using standard recombinant DNA techniques, also may be used. (See, e.g., U.S. Pat. Nos. 4,816,567; and 4,816,397.) Humanized antibodies are antibody molecules from non-human species having one or more complementarity determining regions (CDRs) from the non-human species and a framework region from a human immunoglobulin molecule. (See, e.g., U.S. Pat. No. 5,585,089.) Chimeric and humanized monoclonal antibodies may be produced by recombinant DNA techniques known in the prior art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

Completely human antibodies can also be used. Human antibodies may be prepared, for example, using transgenic mice that are incapable of expressing endogenous immunoglobulin heavy and light chain genes, but which may express human heavy and light chain genes. The transgenic mice are immunized in the normal fashion with a selected antigen, e.g., all or a portion of a polypeptide of the disclosure. Monoclonal antibodies directed against the antigen may be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies. see, e.g., U.S. Pat. Nos. 5,625,126; 5,633,425; 5,569,825; 5,661, 016; and 5,545,806. Other human antibodies may be obtained commercially from, for example, Abgenix, Inc. (Freemont, Calif.) and Genpharm (San Jose, Calif.).

Human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903.) Human antibodies can also be produced using various techniques known in the prior art, including phage display libraries (see, e.g., Hoogenboom and Winter, 1991, J. Mol. Biol. 227:381; Marks et al., 1991, J. Mol. Biol. 222:581; Quan and Carter, 2002, "The rise of monoclonal antibodies as therapeutics," in Anti-IgE and Allergic Disease, Jardieu, P. M. and Fick Jr., R. B, eds., Marcel Dekker, New York, N.Y., Chapter 20, pp. 427-469).

In other embodiments, the antibody is a fusion protein of an antibody, or a functionally active fragment thereof. For example, an antibody can be fused via a covalent bond (e.g., a peptide bond) at either the N-terminus or the C-terminus to an amino acid sequence of another protein (or portion thereof, such as at least a 10, 20 or 50 amino acid portion of the protein) that is not the antibody.

Antibodies also include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including but not limited to specific chemical cleavage, acetylation, formylation, metabolic synthesis in the presence of tunicamycin, etc. Additionally, the analog or derivative may contain one or more unnatural amino acids.

Antibodies may have modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety). Antibodies immunospecific for a target antigen may be obtained commercially or from other sources or produced by any method known to one of skill in the art such as, e.g., chemical synthesis or recombinant expression techniques. The nucleotide sequence encoding antibodies immunospecific for a cancer cell antigen may be obtained, e.g., from the GenBank database or a database like it, the literature publications, or by routine cloning and sequencing.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, N.C.) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (Medimmune, Inc., MD) which is a humanized antibody for the treatment of sarcoma; Campath I/H (Leukosite, Mass.) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, Calif.) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100-105), mAbs against the CD40 antigen, such as S2C6 mAb (Francisco et al., 2000, Cancer Res. 60:3225-3231) and chimeric and humanized variants thereof, mabs against the cD33 antigen; mabs against the EphA2 antigen; mAbs against the CD70 antigen, such as 1F6 mAb and 2F2 mAb and chimeric and humanized variants thereof, and mAbs against the CD30 antigen, such as AC10 (Bowen et al., 1993, J. Immunol. 151:5896-5906; Wahl et al., 2002, Cancer Res. 62(13):3736-42) and chimeric and humanized variants thereof. Many other internalizing antibodies that bind to tumor associated antigens may be used and have been reviewed (see, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

In some embodiments, known antibodies for the treatment or prevention of an autoimmune disease are used in accordance with the compositions and methods of the disclosure. Antibodies immunospecific for an antigen of a cell that is responsible for producing autoimmune antibodies may be obtained from a commercial or other source or produced by any method known to one of skill in the art such as, e.g., chemical synthesis or recombinant expression techniques.

In some embodiments, the antibody is immunospecific for the treatment of an autoimmune disease such as, for example, anti-nuclear antibody; anti-ds DNA; anti-ss DNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL 70; anti-Jo; anti-U1 RNP; anti-La/SSB; anti-SSA; anti-SSB; anti-perital cells antibody; anti-histones; anti-RNP; C ANCA; P ANCA; anti centromere; anti fibrillarin, and anti-GBM antibody. In one embodiment, the antibody binds to an activated lymphocyte that is associated with an autoimmune disease.

In certain embodiments, the antibody may bind to a receptor or a receptor complex expressed on a target cell (e.g., an activated lymphocyte). The receptor or receptor complex may comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA 4, PD 1, and ICOS. Non-limiting examples of suitable TNF receptor superfamily members are CD27, CD40, CD95/Fas, CD134/OX40, CD137/4 1BB, TNF R1, TNFR2, RANK, TACI, BCMA, osteoprotegerin, Apo2/TRAIL R1, TRAIL R2, TRAIL R3, TRAIL R4, and APO 3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C type, S type, and I type lectin.

In another specific embodiment, useful antibody immunospecific for a viral or a microbial antigen are monoclonal antibodies. The antibodies can be chimeric, humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide ⅝) that is capable of eliciting an immune response.

Antibodies immunospecific for a viral or microbial antigen may be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen may be obtained, e.g., from the GenBank database or a database like it, literature publications, or by routine cloning and sequencing.

In a specific embodiment, useful antibodies are those that are useful for the treatment or prevention of viral or microbial infection in accordance with the methods disclosed herein. Examples of antibodies available useful for the treatment of viral infection or microbial infection include, but are not limited to, SYNAGIS (Medimmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG1 antibody useful for the treatment of cytomegalovirus (CMV); and anti-LPS antibodies.

Other antibodies useful in the treatment of infectious diseases include, but are not limited to, antibodies against the antigens from pathogenic strains of bacteria (e.g., *Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp.); pathogenic fungi (e.g., *Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminiths (*Enterobius vermicularis, Trichuris trichiura, Ascaris lumbricoides, Trichinella spiralis, Strongyloides stercoralis, Schistosoma ijaponicum, Schistosoma mansoni, Schistosoma haematobium*, and hookworms).

Other antibodies useful in this disclosure for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non A/Non B Hepatitis virus, Rhinoviridae, Coronaviridae, Rotoviridae, and Human Immunodeficiency Virus.

The antibody also can be an antibody that is present on a target cell or target cell population. For example, transmembrane polypeptides and other markers may be specifically expressed on the surface of one or more particular type(s) of target cells (e.g., a cancer cell) as compared to on one or more normal cells (e.g., a non-cancerous cell(s)). Often, such markers are more abundantly expressed on the surface of the target cells, or exhibit greater immunogenicity, as compared to those on the surface of the normal cells. The identification of such cell surface antigen polypeptides has given rise to the ability to specifically target cells for destruction via antibody-based therapies. Thus, in some embodiments, the antibodies include, but are not limited to, antibodies against tumor-associated antigens (TAA). Such tumor-associated antigens are known in the prior art, and can be prepared for use in generating antibodies using methods and information which are well known in the prior art.

In formula (I), -(L-D) is a linker-drug unit, in which L represents a linker unit having a glycopeptide, and D represents a drug unit. In formula (I), p may be an integer ranging from 1 to 26 depending on the number of inter-chain disulfide bonds present in the antibody A in the formula (I). In one embodiment, p can be an integer ranging from 2 to 8, or an integer of 4. In one embodiment, p can be an integer ranging from 2 to 12, or an integer of 8. In one embodiment, p can be an integer ranging from 2 to 26, or an integer of 12. In one embodiment, p can be an integer of 26.

In some embodiments, the linker unit (-L-) of the disclosure includes a sugar amino acid unit (-SAAs-) and a peptide unit (-AAs-). In some embodiments, the peptide unit can be dipeptide, tripeptide, tetrapeptide, pentapeptide, hexapeptide, heptapeptide, octapeptide, nonapeptide, decapeptide, undecapeptide or dodecapeptide.

In other embodiments, the linker unit (-L-) of the disclosure can be a formula of —C-SAAs-AAs-. In the formula, C— is a conjugating unit selected from a group consisting of

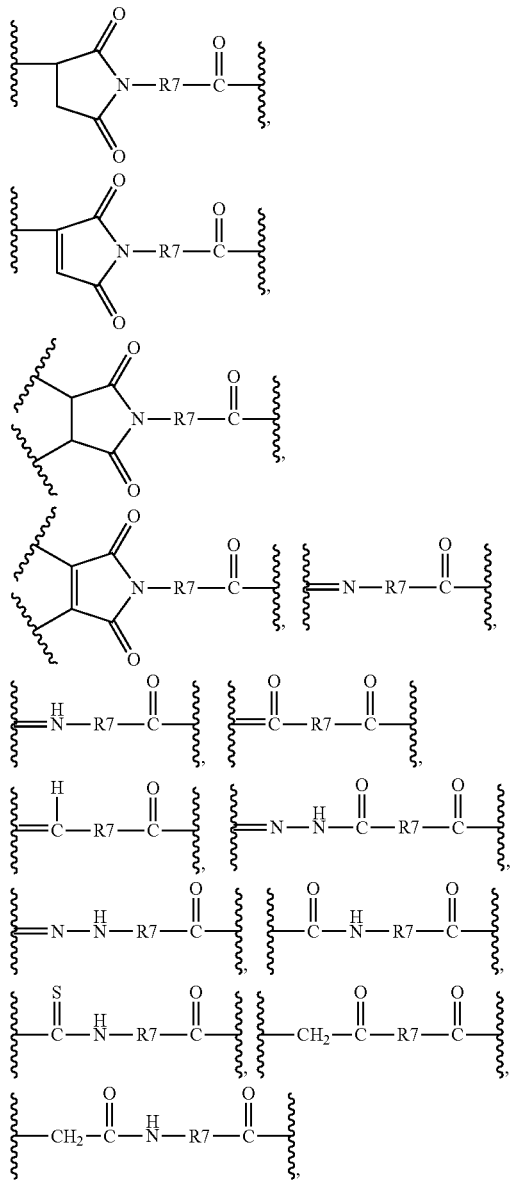

-continued

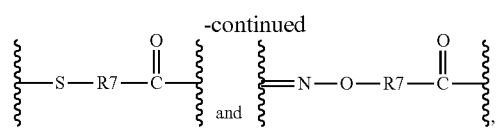

wherein R7 is selected from a group consisting of —C1-C10 alkylene-, —C3-C8 carbocyclo-, —O—(C1-C8 alkyl)-, -arylene-, —C1-C10 alkylene-arylene-, -arylene-C1-C10 alkylene-, —C1-C10 alkylene-(C3-C8 carbocyclo)-, —(C3-C8 carbocyclo)-C1-C10 alkylene-, —C3-C8 heterocyclo-, —C1-C10 alkylene-(C3-C8 heterocyclo)-, —(C3-C8 heterocyclo)-C1-C10 alkylene-, —(CH$_2$CH$_2$O)r- and —(CH$_2$CH$_2$O)r-CH$_2$—, and r is an integer ranging from 1 to 10.

In the formula, the sugar amino acid unit AAs-) of the disclosure is anted by formula (II):

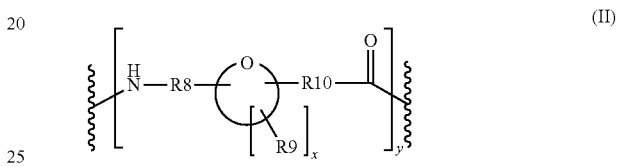

In formula (II), x may be an integer ranging from 1 to 8, y may be an integer ranging from 1 to 4,

may be tetrahydrofuran, dihydrofuran, tetrahydropyran or dihydropyran ring, each of R8 and R10 may be, independently, a single bond, methylene, hydroxymethylene, ethylene, ethylidene, hydroxyethylene, hydroxyethylidene, dihydroxyethylene, dihydroxyethylidene, vinylene, vinylidene, propylene, propylidene, trimethylene, hydroxypropylene, hydroxypropylidene, hydroxytrimethylene, dihydroxypropylene, dihydroxypropylidene, dihydroxytrimethylene, trihydroxypropylene, trihydroxypropylidene or trihydroxytrimethylene, each R9 may be, independently, hydroxyl, methyl, hydroxymethyl, ethyl, hydroxyethyl, dihydroxyethyl, propyl, hydroxypropyl, dihydroxypropyl or trihydroxypropyl, or any two R9 in the same ring carbon together with the carbon to which they are attached form a carbonyl group, or any two R9, R8 and any one R9, or R10 and any one R9 form a second tetrahydrofuran, dihydrofuran, tetrahydropyran or dihydropyran ring that fuses to the original tetrahydrofuran, dihydrofuran, tetrahydropyran or dihydropyran ring, or any two R9, R8 and any one R9, or R10 and any one R9 together with a methylene, ethylidene, 1-propylidene, 2-propylidene or benzylidene group form a cyclic acetal or ketal ring that fuses to the original tetrahydrofuran, dihydrofuran, tetrahydropyran or dihydropyran ring.

In the disclosure, examples of said sugar amino acids include but are not limited to:

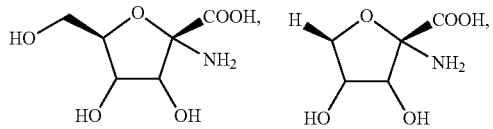

-continued
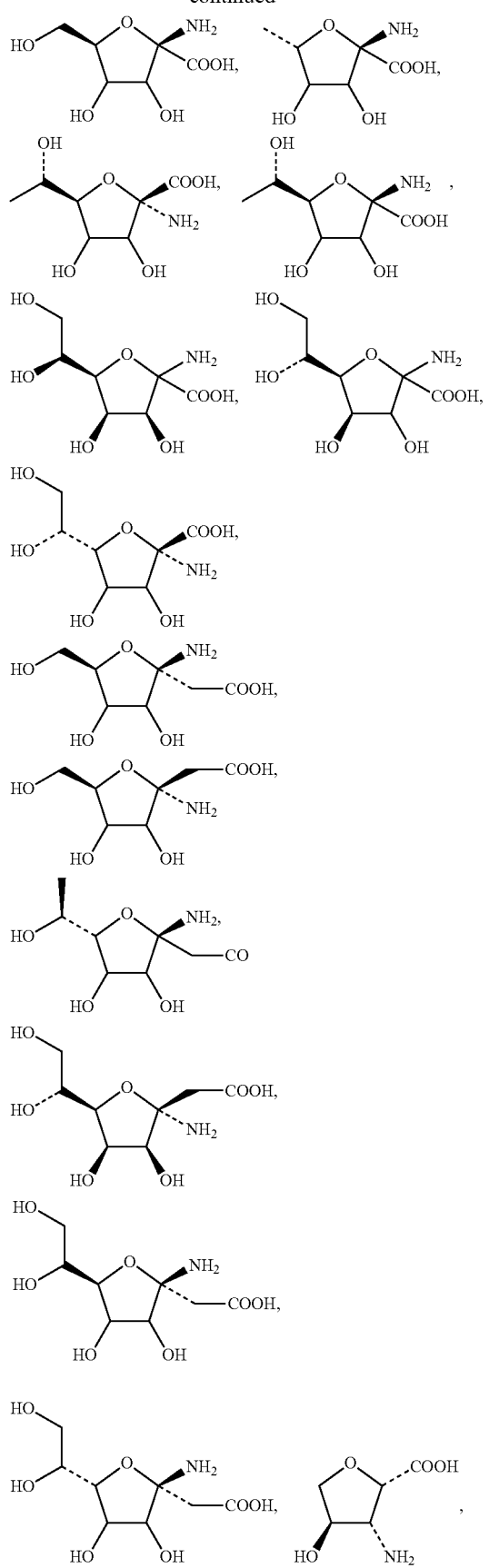
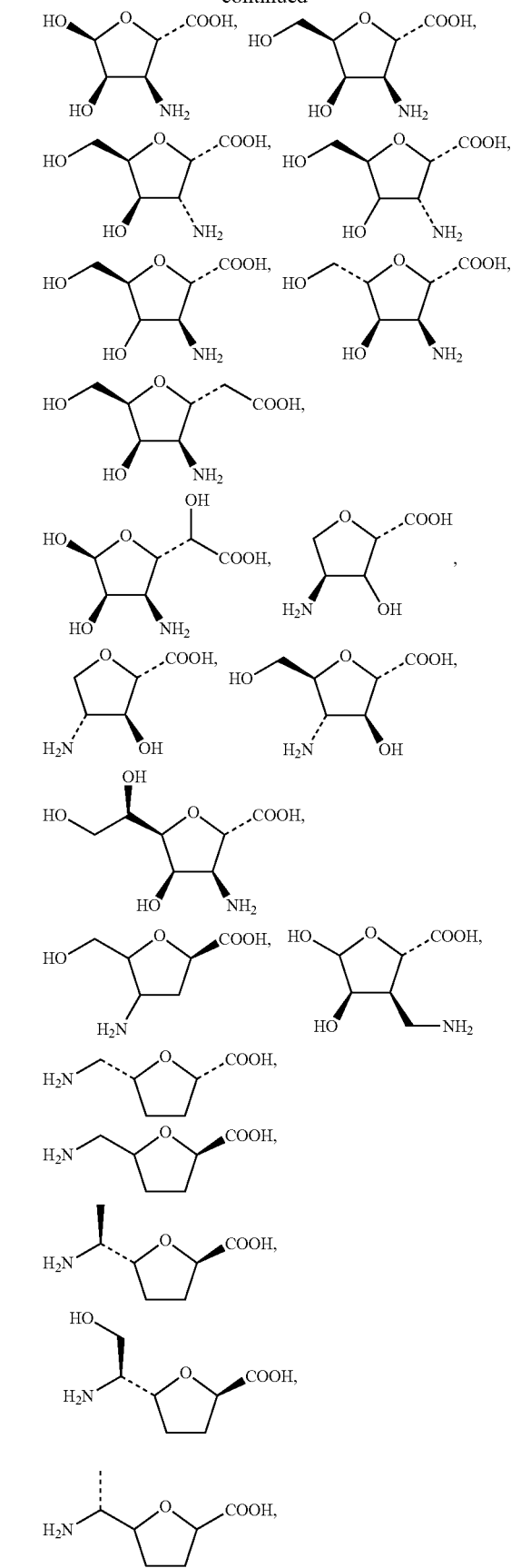

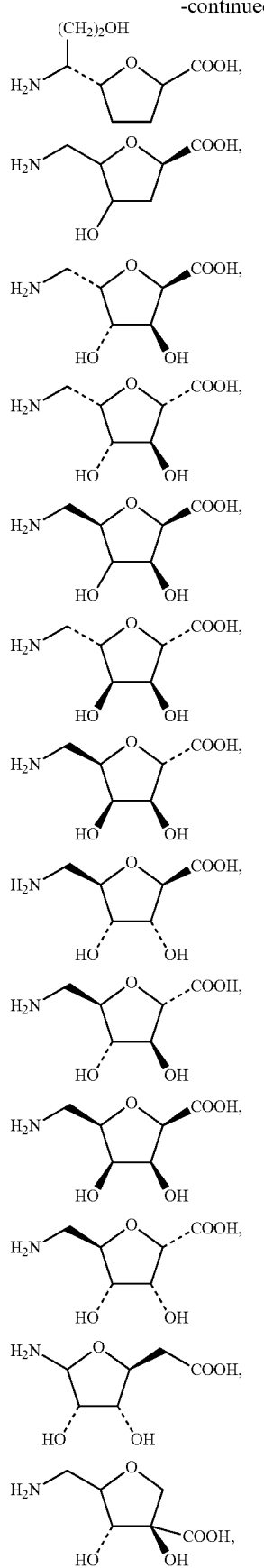
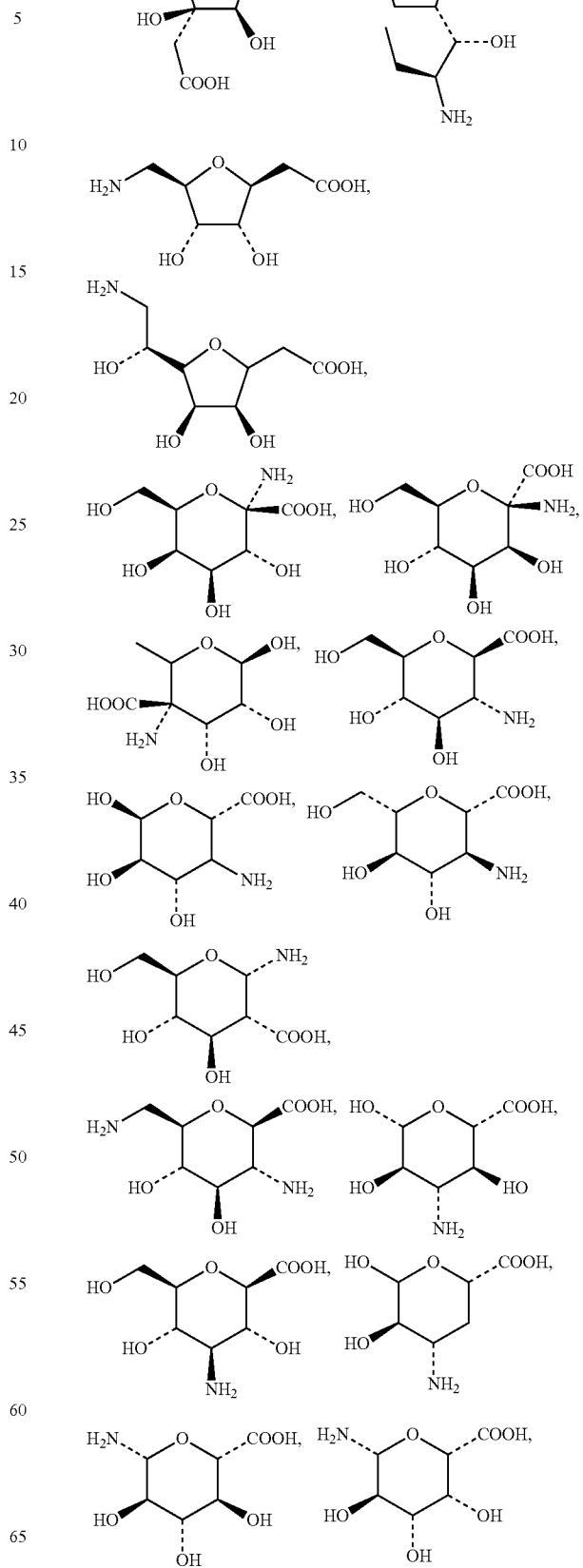

-continued

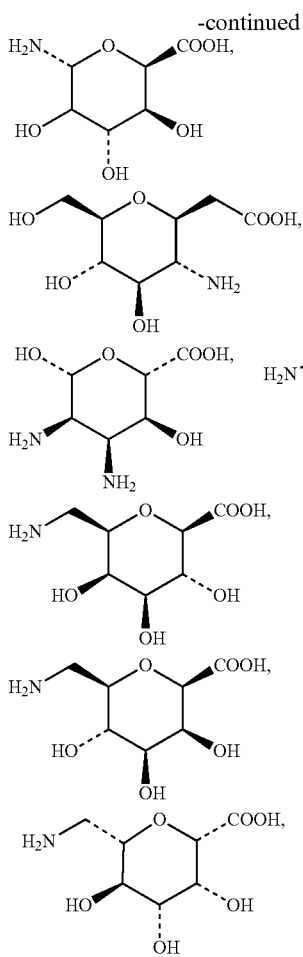

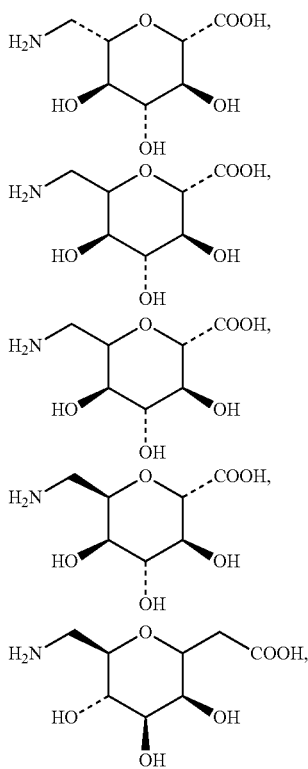

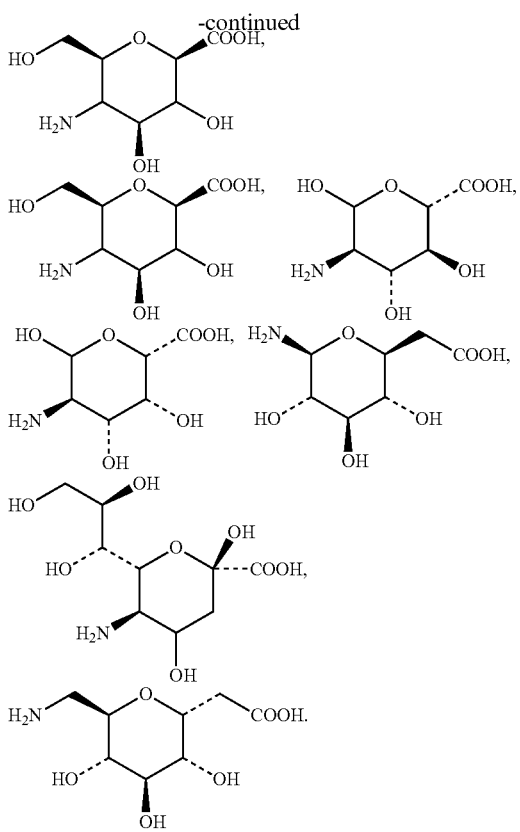

In the formula, the peptide unit (-AAs-) is represented by formula (III):

$$\begin{array}{c}(III)\end{array}$$

In formula (III), z is an integer ranging from 0 to 10, R11 may be —$(CH_2)_3NHC(=NH)NH_2$, —$(CH_2)_3NH_2$, —$(CH_2)_3NHCONH_2$, —$(CH_2)_4NHC(=NH)NH_2$, —$(CH_2)_4NH_2$ or —$(CH_2)_4NHCONH_2$, R12 can be H, methyl, ethyl, propyl, isopropyl, cyclopropyl, butyl, sec-butyl, isobutyl, tert-butyl, cyclobutyl, phenyl or benzyl, R13 may be hydrogen, methyl, isopropyl, cyclopropyl, butyl, sec-butyl, isobutyl, tert-butyl, cyclobutyl, cyclohexyl, phenyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl, 3-pyridylmethyl or 4-pyridylmethyl.

In some embodiments, the peptide unit (-AAs-) can be enzymatically cleaved by one or more enzymes, for example, by a tumor-associated protease to liberate a drug unit (-D).

In another embodiment, C— is the conjugating unit selected from a group consisting of

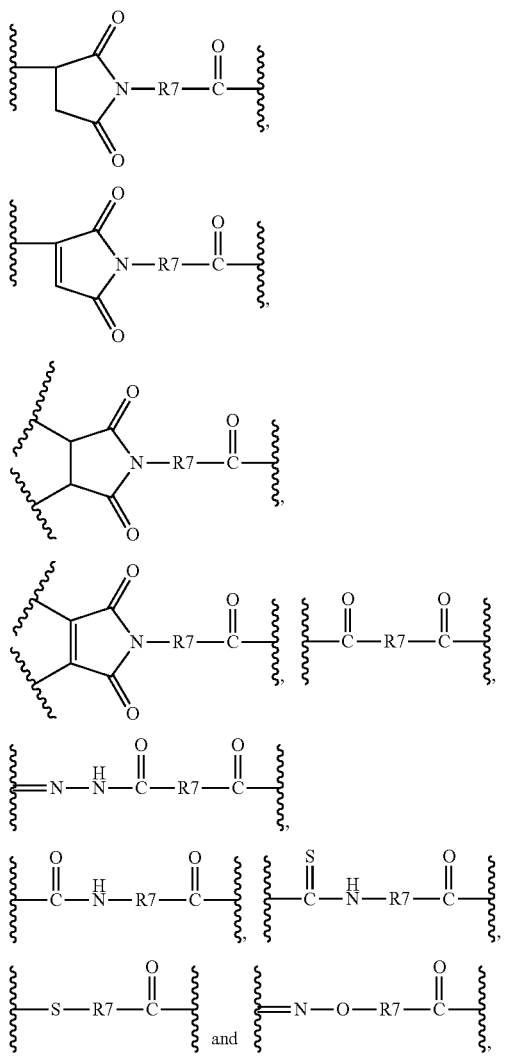

wherein R7 is selected from a group consisting of -1,5-pentylene-, -1,6-hexylene-, -1,4-cyclohexylene-, —(CH2CH2O)r-CH2- and —(CH2CH2O)r-CH2-CH2-, and r is an integer ranging from 2-5.

In still another embodiment, -SAAs- is the sugar amino acid unit selected from a group consisting of

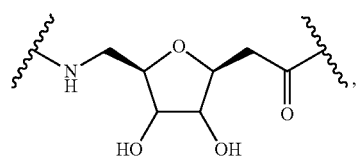

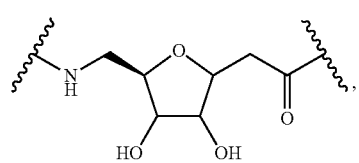

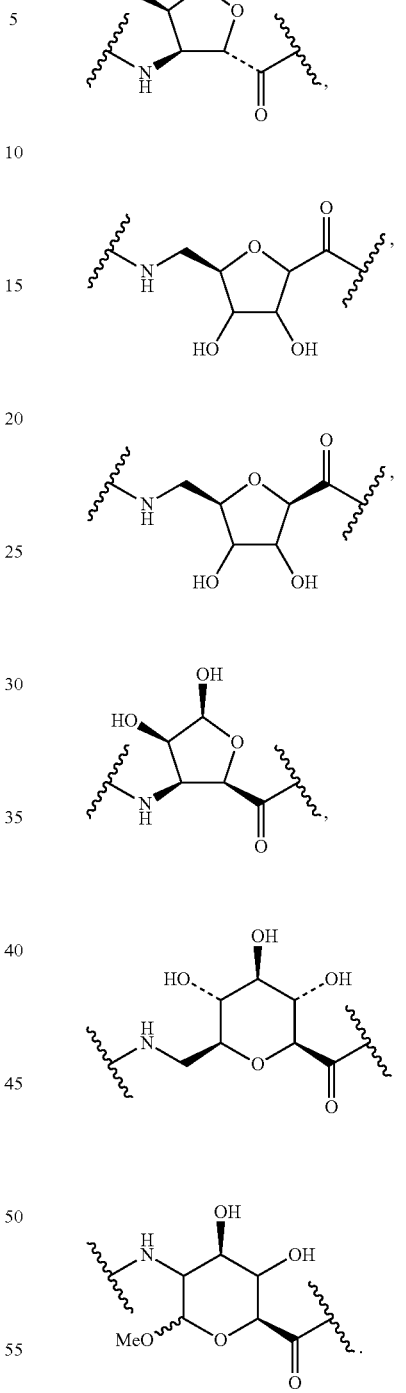

In one embodiment, the peptide unit (-AAs-) can be selected from a group consisting of -Val-Cit-, -Val-Lys-, -Val-Arg-, -Phe-Cit-, -Phe-Lys- and -Phe-Arg-.

However, it should be appreciated that the above structures are merely examples and the scope of the invention is not intended to be limited.

In one embodiment, the drug unit (-D) is the cytotoxic agent selected from a group consisting of

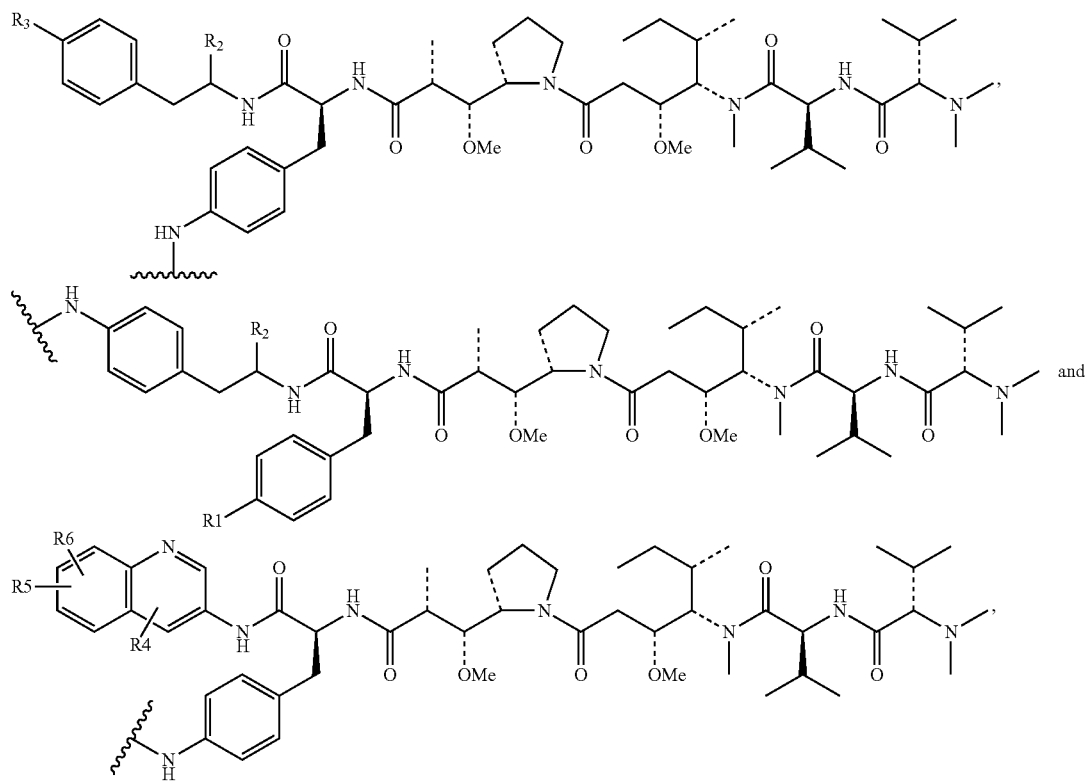

wherein R1, R2, R3, R4, R5 and R6 are each, independently, hydrogen, amino, nitro, halogen, hydroxyl, methoxy, ethoxy, carboxylic acid, methoxycarbonyl, ethoxycarbonyl, methylamino, dimethylamino, ethylamino, diethylamino, 1-pyrrolidinyl, 1-piperidinyl, 1-piperazinyl, aminocarbonyl, methylaminocarbonyl, dimethylaminocarbonyl, ethylaminocarbonyl, diethylaminocarbonyl, 1-pyrrolidinylcarbonyl, 1-piperidinylcarbonyl, 1-piperazinylcarbonyl, methyl, ethyl, propyl, isopropyl or phenyl.

In one embodiment, the drug unit (-D) is a cytotoxic agent selected from a group consisting of amanitins, anthracyclines, auristatins, baccatins, calicheamicins, camptothecins, cemadotins, colchicines, colcimids, combretastatins, cryptophysins, discodermolides, duocarmycins, echinomycins, eleutherobins, epothilones, estramustines, lexitropsins, maytansinoids, netropsins, puromycins, pyrrolobenzodiazepines, rhizoxins, taxanes, tubulysins, and vinca alkaloids.

In some embodiments, the drug unit (-D) can be calicheamicin, camptothecin, maytansinoid or anthracycline. In some embodiments, the Drug unit may be taxane, a topoisomerase inhibitor, vinca alkaloid or the like. In some typical embodiments, suitable cytotoxic agents include, for example, DNA minor groove binders (e.g., enediynes and lexitropsins, a CBI compound; see also U.S. Pat. No. 6,130, 237), duocarmycins, taxanes (e.g., paclitaxel and docetaxel), puromycins, and vinca alkaloids. Other cytotoxic agents include, for example, CC-1065, SN-38, topotecan, doxorubicin, rhizoxin, cyanomorpholino-doxorubicin, echinomycin, combretastatin, netropsin, epothilone, estramustine, cryptophysin, cemadotin, maytansinoid, discodermolide, eleutherobins or mitoxantrone.

In some embodiments, the drug unit (-D) can be an anti-tubulin agent. Examples of anti-tubulin agents include, auristatin, taxane and vinca alkaloid. Other anti-tubulin agents include, for example, baccatin derivatives, cemadotin, colchicine, colcimid, combretastatins, cryptophycins, discodermolide, eleutherobin, estramustine, maytansinoid, nocodazole or taxane analog.

In certain embodiments, the cytotoxic agent can be maytansinoids or another group of anti-tubulin agents. For example, in specific embodiments, the maytansinoid is maytansine or DM-1 (ImmunoGen, Inc.; see also Chari et al., 1992, Cancer Res. 52:127-131).

In certain embodiments, the cytotoxic or cytostatic agent can be dolastatin. In certain embodiments, the cytotoxic or cytostatic agent is of the auristatin class. Thus, in a specific embodiment, the cytotoxic or cytostatic agent is MMAE.

In another embodiment, a method 100 for forming an antibody-drug conjugate (ADC) is also provided. FIG. 1 is a flow diagram illustrating a method 100 for forming an antibody-drug conjugation (ADC) in accordance with some embodiments of the present disclosure.

First, the method 100 proceeds to step 102 by forming a first solution. The first solution is formed by reacting an antibody and a reducing agent in a buffer. In some embodiments, the antibody may be a full-length antibody or an antibody fragment. In some embodiments, the antibody may be a chimeric antibody or a functionally active fragment thereof, a humanized antibody or a functionally active fragment thereof, a human antibody or a functionally active fragment thereof, or a mouse antibody or a functionally active fragment thereof. In other embodiments, the antibody can be an antibody from other species such as a rat antibody or a functionally active fragment thereof, a goat antibody or a functionally active fragment thereof, or a rabbit antibody or a functionally active fragment thereof. In some embodiments, the antibody may be any appropriate antibody described above. In certain embodiments, the antibody may include Herceptin, Erbitux, HLX-07, EG12014, anti-Ep-CAM Ab, IgG1, Rituximab, Ibritumomab tiuxetan, Tositumomab, Brentuximab vedotin, Alemtuzumab, IGN101, Adecatumumab, Labetuzumab, huA33, Pemtumomab, Oregovomab, CC49 (minretumomab), cG250, J591, MOv18, MORAb-003 (farletuzumab), 3F8, ch14.18, KW-2871, hu3S193, IgN311, Bevacizumab, IM-2C6, CDP791, Etaracizumab, Volociximab, Cetuximab, Panitumumab, Nimotuzumab, 806, Trastuzumab, Pertuzumab, MM-121, AMG 102, METMAB, SCH 900105, AVE1642, IMC-A12, MK-0646, R1507, CP 751871, KB004, IIIA4, Mapatumumab (HGS-ETR1), HGS-ETR2, CS-1008, Denosumab, Sibrotuzumab, F19, or 8106. The description in related paragraphs may be referred to for a description of the other antibodies, and hence it is not described again to avoid unnecessary repetition.

In step 102, an initial concentration of the antibody may be less than 20 mg/mL. For example, the initial concentration of the antibody may be in a range of about 1 to about 20 mg/mL. However, the initial concentration of the antibody is not limited thereto. The initial concentration of the antibody may be more than 20 mg/mL depending on the requirement.

In one embodiment, the reducing agent may be selected from a group consisting of tris(2-carboxyethyl)phosphine (TCEP), 2-aminoethanethiol, dithiothreitol (DTT), 2-mercaptoethylamine hydrochloride (2-MEA), and other appropriate reducing agents. In one embodiment, the buffer can be a borate buffer composed of 25 mM sodium borate, 25 mM NaCl, and 1 mM diethylenetriaminepentaacetic acid (DTPA)(pH 8), a PBS buffer composed of 2.67 mM KCl, 1.47 mM $KH_2PO_4$, 137.93 mM NaCl, and 8.06 mM $Na_2HPO_4$-$7H_2O$ (pH 7.4), or other buffers with appropriate pH values.

In step 102, the molar equivalent ratio of the reducing agent and the antibody may be adjusted according to actual need such as the desired number of free thiols and the desired properties of the antibody-drug conjugate such as DAR value.

Theoretically, the DAR value corresponds to the number of free thiols provided in the reduced antibody after the reduction. Also, the molar equivalent ratio of the reducing agent and the antibody may also be affected by the reducing ability of the reducing agent. Therefore, the reducing agent and reducing conditions are selected such that the inter-chain disulfide bonds present in the antibody are converted to a desired number of free thiols.

Theoretically, 1 molar equivalent of TCEP may produce 2 free thiols in the antibody. Therefore, to achieve a desired average DAR value of 3.5-4.0, 1.75-2 molar equivalent of TCEP may be used to produce an average number of free thiols of 3.5-4.0 in the antibody. However, it should be realized that the actual molar equivalent of TCEP used in the reaction may be more than the aforementioned theoretical value.

For example, to achieve an average DAR value of 26, theoretically, the molar equivalent ratio of TCEP and the antibody may be adjusted to 13 to produce an average number of free thiols of 26. However, the actual molar equivalent of TCEP used in the reaction may be more than 13 molar equivalent. Similarly, to achieve an average DAR value of 12, theoretically, the molar equivalent ratio of TCEP and the antibody may be adjusted to about 6 to produce an average number of free thiols of 12. However, the actual molar equivalent of TCEP used in the reaction may be more than 6 molar equivalent.

In one embodiment of the present disclosure, to achieve an average DAR value of 3.5~4.0, the molar equivalent ratio of TCEP and the antibody may be adjusted in a range of about 1.8~2.8 to produce an average number of free thiols of 3.5~4.0 in the antibody. In another embodiment, to achieve an average DAR value of 3.5~4.0, the molar equivalent ratio of TCEP and the antibody may be 2.1~2.5. In still another embodiment, to achieve an average DAR value of more than 4.0 such as 5.4, the molar equivalent ratio of TCEP and the antibody may be about 3.4

In step 102, the reaction may be conducted at room temperature (such as 15-25° C.) to 40° C. for about 1-3 hours. After the reaction, the antibody is reduced to produce free thiols.

Next, the method 100 proceeds to step 104 by preparing a linker-drug unit in organic phase or aqueous phase to form a second solution, wherein the linker unit has a glycopeptide. In one embodiment, the organic phase may include dimethyl sulfoxide (DMSO), acetonitrile (ACN), N, N-dimethylacetamide (DMA), propylene glycol (PG), and so on. The concentration of the organic solvent for preparing the linker-drug unit may be in a range of about 0% (v/v) to 100% (v/v), such as 0%, 10% (v/v), 20%, 30% (v/v), 50%, 75%, or 100% (v/v).

In some embodiments, the glycopeptide may include a monosaccharide, a disaccharide or a polysaccharide. In some embodiments, the linker-drug unit having a glycopeptide may be selected from the groups consisting of MHT-47, MHT-71, MHT-81a, MHT-93, MHT-98a, CCH-28, CCH-35, CCH-38, FCW-016, WHY-46 and CCH-41. In some embodiments, the linker-drug unit having a glycopeptide may be any of the appropriate linker-toxins described above. The description in related paragraphs may be referred to for a description of the other linker-drug units, and hence to avoid unnecessary repetition it is not described again herein.

Next, the method 100 proceeds to step 106 by performing a conjugation process by mixing the first solution and the second solution to form a mixture solution.

In some embodiments, the concentration of an organic solvent in the mixture solution is in a range of about 0% (v/v) to about 20% (v/v). For example, the concentration of an organic solvent in the mixture solution may be 0~2% (v/v), 2~5% (v/v), 5~7% (v/v), 7~10% (v/v), 10~15% (v/v), or 15~20% (v/v). In step 106, the reduced antibody of the first solution is conjugated with the linker-drug unit in a co-solvent system containing 0~20% (v/v) of organic solvent to form an ADC. In step 106, the conjugation process may be conducted for about 0.5~2 hour at 0~10° C. For example, in one embodiment, the conjugation process may be conducted for 0.5 hours at 4° C.

It should be noted that although previous studies have developed various ADCs, a co-solvent system containing a high content of organic solvent is required during the conjugation process. For example, in the conjugation process provided by Seattle Genetics, 2.75 molar equivalent of tris(2-carboxyethyl)phosphine (TCEP) is used as a reducing agent to reduce the inter-chain disulfide bond in a monoclonal antibody to free thiol groups. However, the reduced antibody is conjugated with maleimide of MC-Val-Cit-PAB in a co-solvent system containing 20% (v/v) of organic solvent. In this previous study, if the content of organic solvent is decreased in the co-solvent system, the linker-toxin cannot be completely dissolved and cannot be conjugated to the antibody in a homogeneous phase, thereby reducing the conjugation efficiency.

In contrast, the present disclosure uses novel linker-toxins with high aqueous solubility to form ADCs. Linkers are designed to have sugar amino acids to enhance the hydrophilicity of linker and increase the stability of the final ADC products. Therefore, the content of organic solvent used during the conjugation process of the ADC is effectively reduced and high conjugation efficiency of the ADC is achieved. In addition, due to the reduced content of organic solvent, the following purification and analysis become easier. Also, the improved hydrophilicity of linker-toxin also decreases aggregation of ADC, thereby enhancing the stability of ADC. There are significant benefits for sample storage and formulation design. The antibody-drug conjugate containing the linker unit having the glycopeptide has an increased stability compared to an antibody-drug conjugate containing a linker unit without a glycopeptide.

Compared to the MC-Val-Cit-PAB developed by Seattle Genetics which needs 20% of organic solvent, the present disclosure has demonstrated that the linker-toxins having sugar amino acids can significantly reduce the use of organic solvent during the conjugation process of ADC. Also, it has been demonstrated that the conjugation process using specific linker-toxins can be performed in a pure aqueous phase. ADCs conjugated in a pure aqueous phase have little aggregation. HMWS analyzed by SEC is less than 0.1% (referring to the following Examples 20, 21 and FIGS. 13B, 14B).

Moreover, so far, the commercial ADC drugs, Kadcyla® and Adcetris®, are conserved in a frozen crystal form, and must be used within one day after reconstitution. However, the ADC of the present disclosure has excellent stability, and can be preserved in liquid form at 4° C. for over four months (referring to the following Example 19 and FIG. 18).

In addition, in the present disclosure, the molar equivalent ratio of the antibody and the linker-drug unit is selected such that the antibody-drug conjugate may have an average DAR in a range of about 3.5 to about 4.0. It should be appreciated that the average DAR of ADC may be adjusted according to actual need. For example, in some embodiments, the average DAR of ADC may be more than 4.0.

Finally, the method 100 proceeds to step 108 by purifying the mixture solution. In some embodiments, a desalting column or tangential flow filtration (TFF) can be used to purify the mixture solution to remove unconjugated linker-toxins and obtain the purified ADCs. During the elution, the buffer can be changed to another appropriate buffer solution such as PBS buffer (2.67 mM KCl, 1.47 mM $KH_2PO_4$, 137.93 mM NaCl, 8.06 mM $Na_2HPO_4$-$7H_2O$, pH 7.4), or other formulation solution such as SGN (20 mM sodium citrate, 6.3% (w/v) trehalose, 0.2 mg/mL polysorbate 80, pH 6.0).

According to the hydrophobic interaction chromatography (HIC) analysis, the average DAR (drug-to-antibody ratio) of the resulting ADCs of the present disclosure is about 3.5 to about 4.0 and the conjugation efficiency is more than 90%, such as 92%, 93%, 94%, 95% or 96%. According to the size-exclusion chromatography (SEC) analysis, there is no significant high molecular weight species (HMWS) produced during the conjugation process. In addition, the resulting ADCs of the present disclosure have great thermal stability, storage stability and tumor growth inhibition ability.

The Preparation Examples and Examples are described below to illustrate the method for forming the linker-toxins and antibody-drug conjugates, and the properties of the antibody-drug conjugates.

PREPARATION EXAMPLES AND EXAMPLES

The disclosure will be described in detail by the following examples. Among them, MMAE (a well-known toxin) and auristatin F (AF, a well-known toxin) were purchased from Concortis Biotherapeutics. Z-Val-Cit-OH and various sugar amino acids were synthesized based on the literature. The structure of the above compounds is well known by those skilled in the art, and is not described herein for simplicity The abbreviations used in linker-toxin and their corresponding chemical structures are listed in Table 1.

TABLE 1

MHT-47

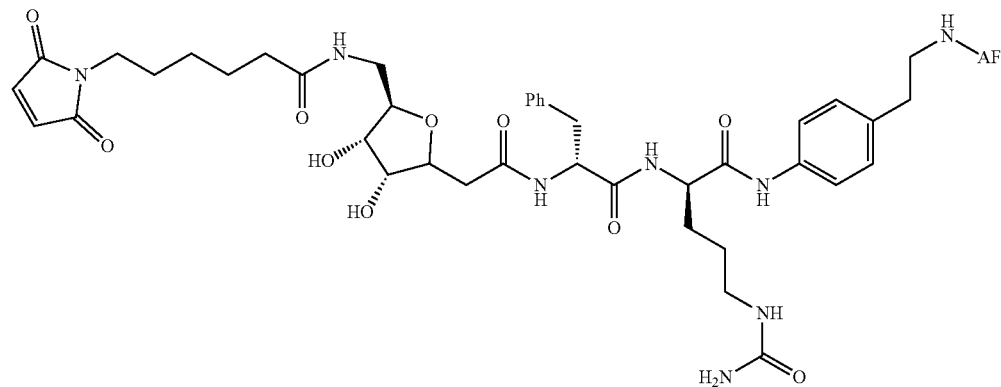

TABLE 1-continued
MHT-71
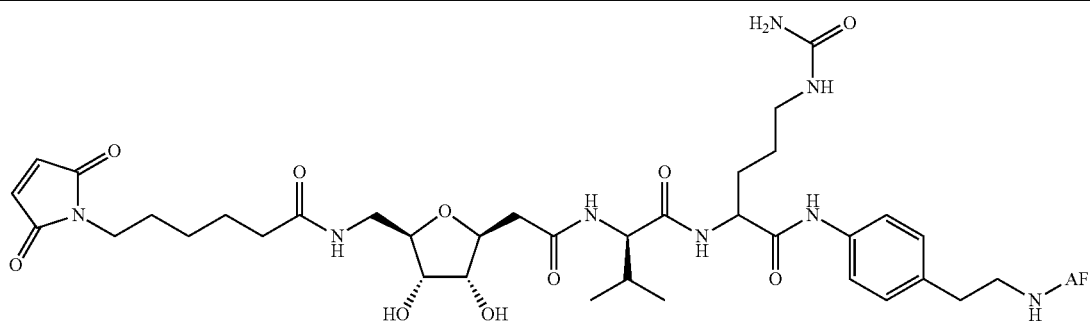
MHT-81a
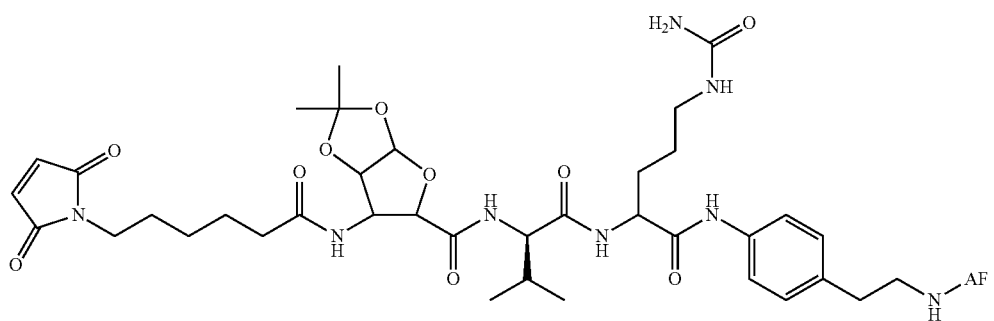
MHT-93
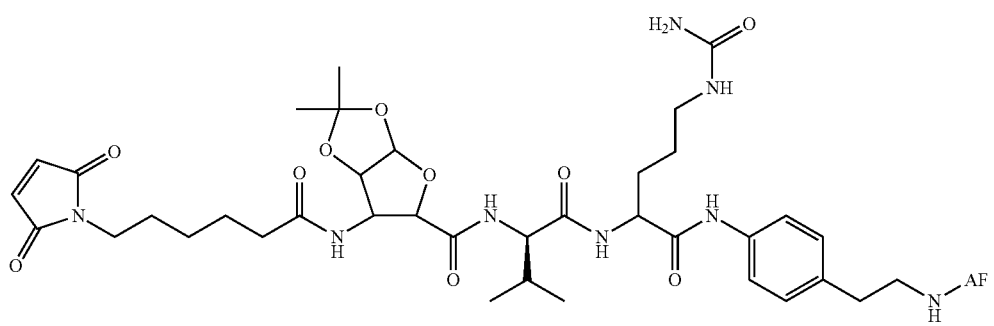
MHT-98a
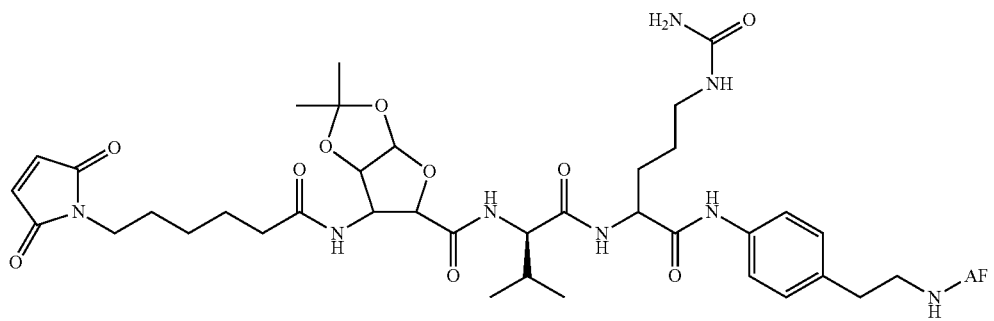
CCH-028
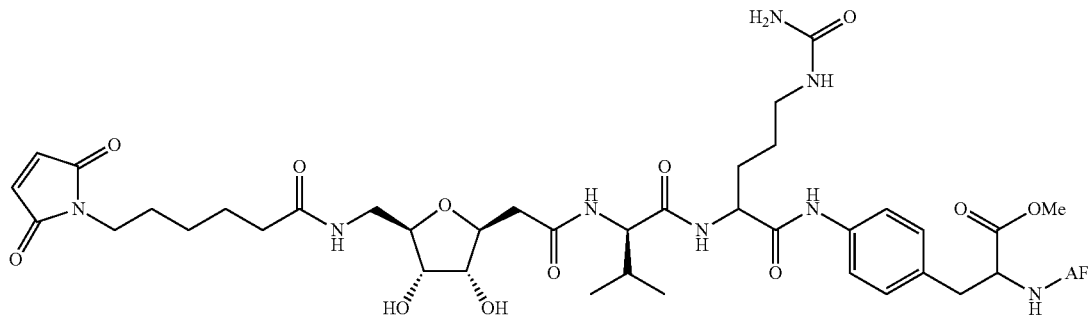

TABLE 1-continued
CCH-035
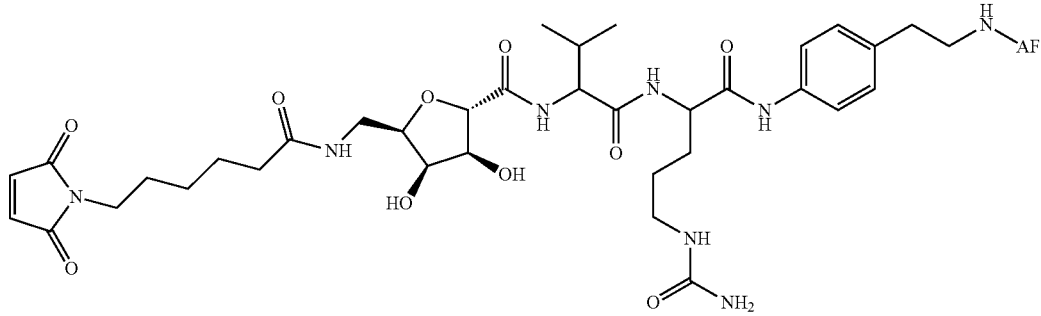
CCH-038
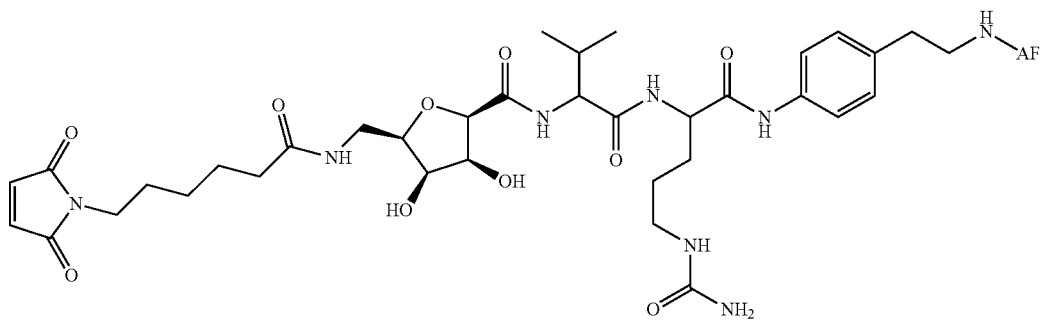
CCH-041
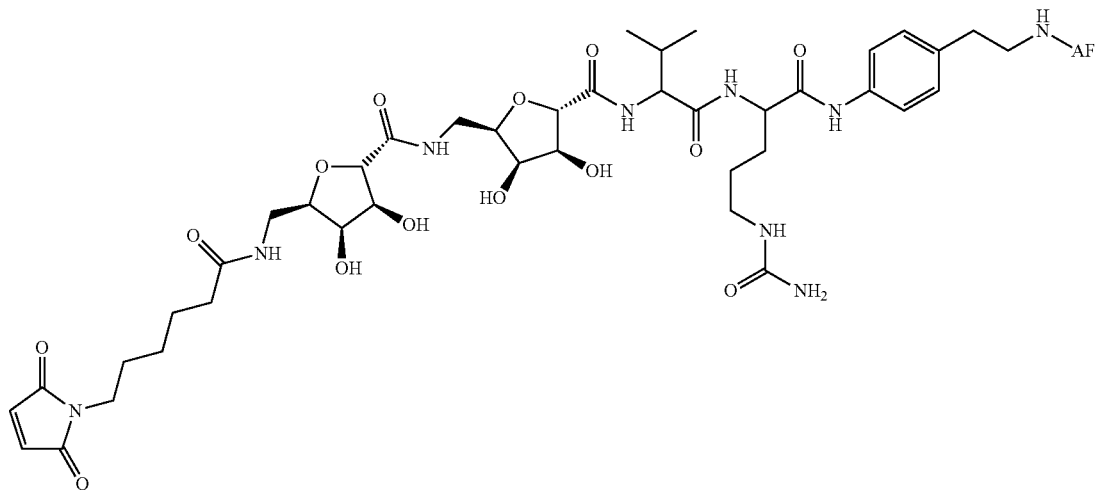
FCW-016
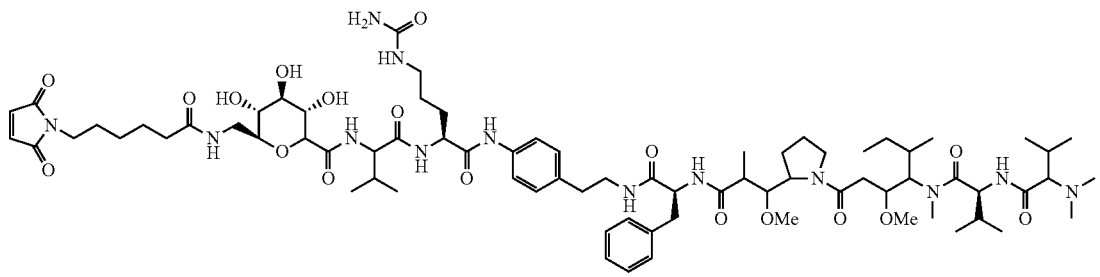 [SMILES: CCC(C)C(C(CC(=O)N1CCCC1C(OC)C(C)C(=O)N[C@@H](Cc1ccccc1)C(=O)NCCc1ccc(NC(=O)[C@H](CCCNC(N)=O)NC(=O)C(NC(=O)C2O[C@@H](CNC(=O)CCCCCN3C(=O)C=CC3=O)[C@H](O)[C@@H](O)[C@@H]2O)C(C)C)cc1)OC)N(C)C(=O)[C@@H](NC(=O)C(C(C)C)N(C)C)C(C)C]

TABLE 1-continued
WHY-46
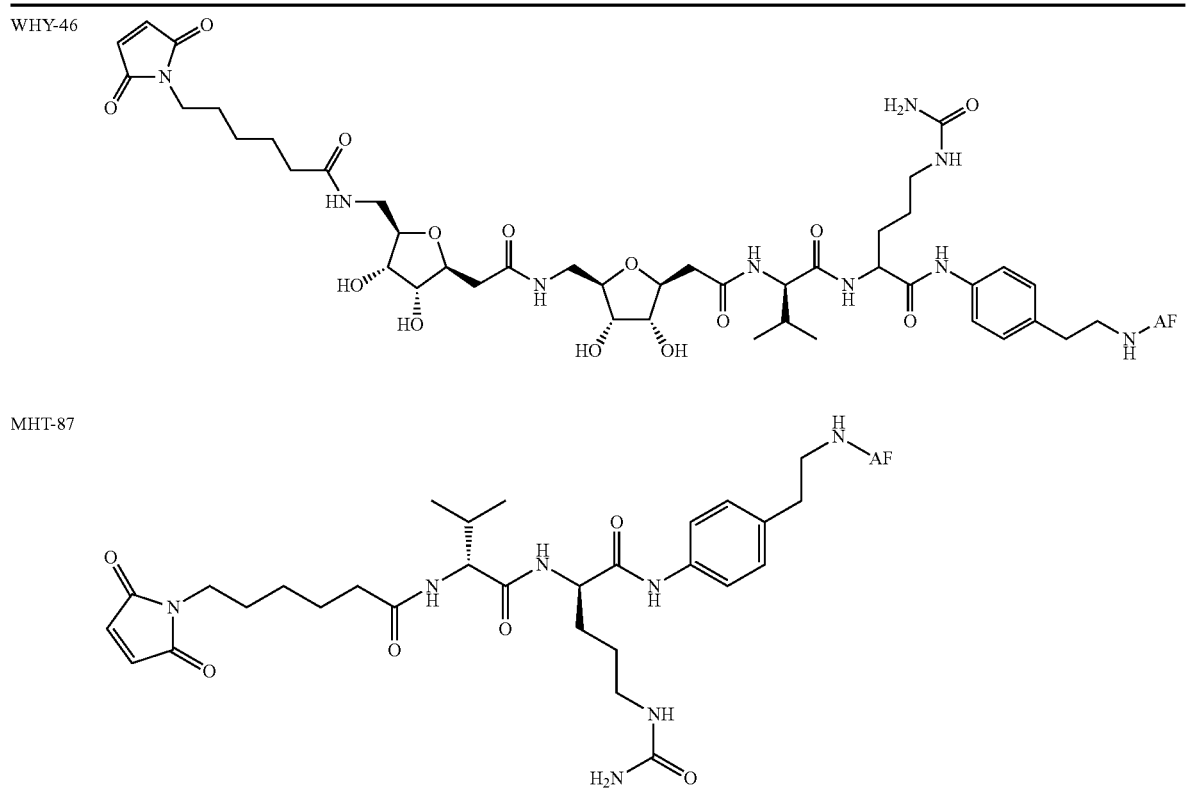
MHT-87
| TABLE 2 | |
|---|---|
| Antibody | Brand name |
| EG12014 | EirGenix |
| Human IgG1 | Sigma |
| Erbitux ® (Cetuximab) | Merck |
| Herceptin ® (trastuzumab) | Roch |
| HLX-07 | Henlix Inc. |
| Anti-EpCAM | Dr. Han-Chung Wu |
Linker-Toxin
Preparation Example 1
Synthesis of MHT-47
[MC-SAA1-Phe-Cit-APEA-AF]
The linker-toxin MHT-47 was synthesized according to the procedures shown in the following scheme.
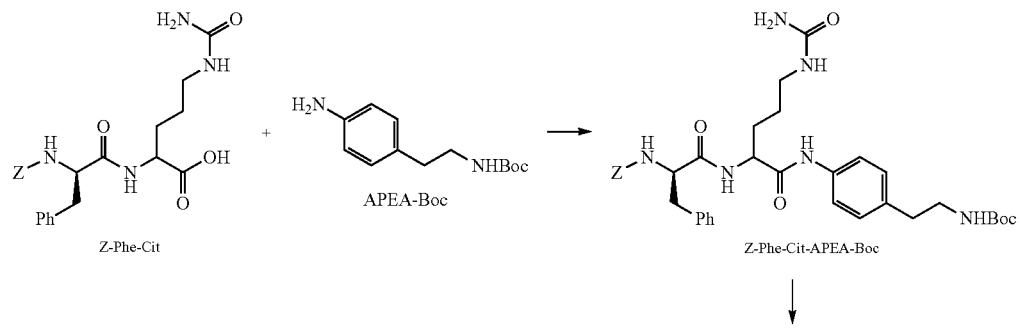

33    34
-continued
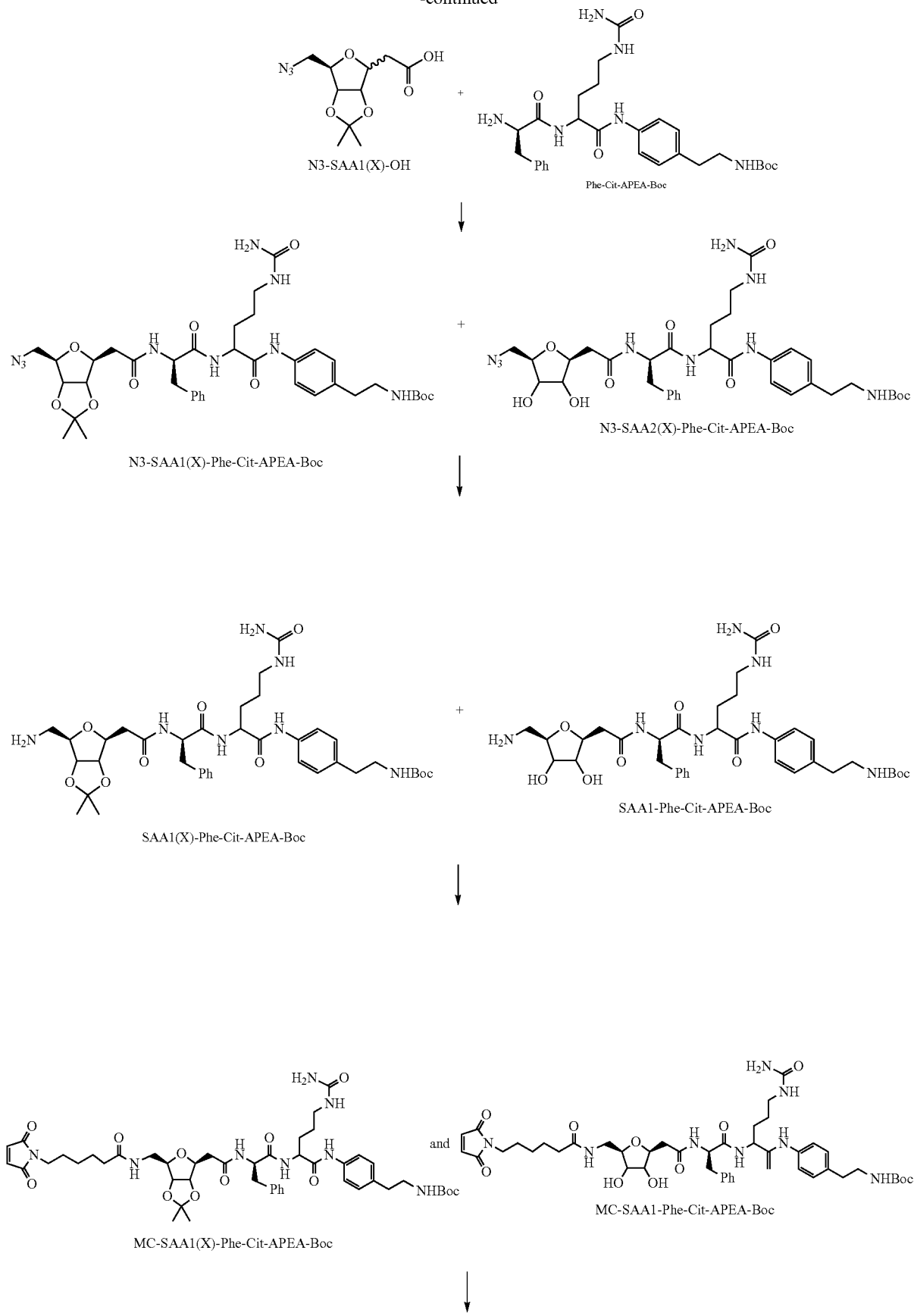

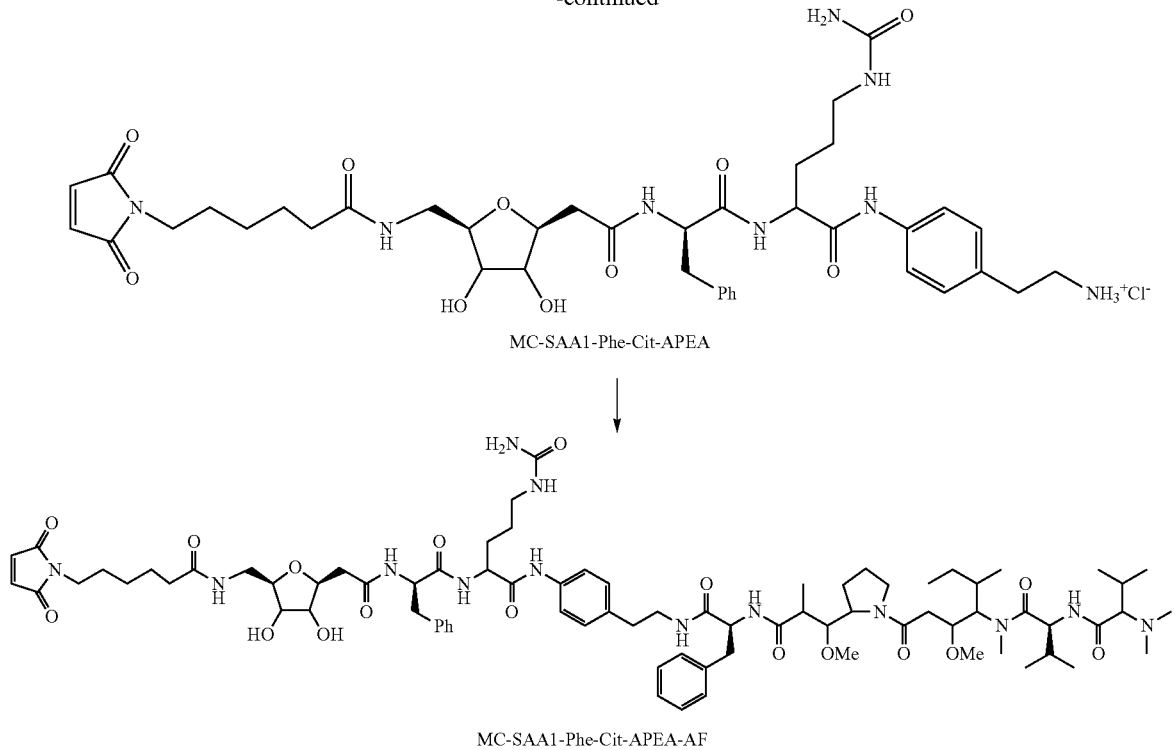

MC-SAA1-Phe-Cit-APEA

MC-SAA1-Phe-Cit-APEA-AF

Step 1

Z-Phe-Cit (9.13 g, 20 mmol) was charged into a mixture of dichloromethane (750 mL) and isopropanol (250 mL) and then stirred until the dipeptide was completely dissolved. Then, APEA-Boc (7.09 g, 30 mmol) and EEDQ (7.42 g, 30 mmol) were added and the mixture was stirred at room temperature for 3 days. The solvents were removed under reduced pressure and then diethyl ether (300 mL) was added to the residue. The mixture was filtered off and the crude product was re-suspended in diethyl ether (300 mL). This procedure was repeated 3 times. The collected solid product was finally dried under vacuum to afford Z-Phe-Cit-APEA-Boc (9.53 g, yield 70.6%). The product was characterized by PMR.

Step 2

Z-Phe-Cit-APEA-Boc (2.02 g, 3 mmol) was dissolved in a mixture of THF (250 mL) and methanol (50 mL). After a catalytic amount of Pd/C (10%) was added, the reaction mixture was applied a hydrogen balloon and stirred overnight. After the catalyst was filtered off through a pad of celite, the filtrate was evaporated under reduced pressure to afford Phe-Cit-APEA-Boc as white solid (1.61 g, 99%).

Step 3

To a solution of N3-SAA1(X)—OH (633 mg) and Phe-Cit-APEA-Boc (1.33 g) in a mixture of DCM and DMF (10:1, 110 mL) was added HBTU (1.118 g) and DIPEA (1.02 mL). After 17 hours, DCM was removed under reduced pressure. Water and diethyl ether were added to the remaining crude DMF solution and a beige solid was obtained after filtration. The solid was washed with concentrated aqueous citric acid solution several times to remove most of the HOBt and DMF. N3-SAA1(X)-Phe-Cit-APEA-Boc was finally purified by preparative HPLC (50% acetonitrile in water with 0.1% TFA; UV 210 nm; ODS-3 column 30×250 mm). Acetonitrile was evaporated under reduced pressure and the remaining aqueous solution was submitted to freeze-drying. A white solid was obtained (1 g) consisting of N3-SAA1(X)-Phe-Cit-APEA-Boc and N3-SAA1-Phe-Cit-APEA-Boc. LC-MS: N3-SAA1(X)-Phe-Cit-APEA-Boc ($C_{38}H_{53}N_9O_9$) required [MH$^+$]=780.9, found [MH$^+$]=781.8; N3-SAA1-Phe-Cit-APEA-Boc ($C_{35}H_{49}N_9O_9$) required [MH$^+$]=740.8, found [MH$^+$]=741.7.

Step 4

The mixture of N3-SAA1(X)-Phe-Cit-APEA-Boc and N3-SAA1-Phe-Cit-APEA-Boc (100 mg) was dissolved in methanol (50 mL). After a catalytic amount of Pd/C (10%) was added, the reaction mixture was applied a hydrogen balloon and stirred overnight. After the catalyst was filtered off through a pad of celite, the methanol was removed under reduced pressure and a white solid was obtained (78 mg) consisting of SAA1(X)-Phe-Cit-APEA-Boc and SAA1-Phe-Cit-APEA-Boc.

Step 5

To a solution of SAA1(X)-Phe-Cit-APEA-Boc and SAA1-Phe-Cit-APEA-Boc (210 mg) in MeOH (50 mL) was added MC-OPFP (103 mg) followed by the addition of DIPEA (0.047 mL). After 17 hours, the reaction mixture was concentrated. The crude product was purified by preparative HPLC (50% acetonitrile in water with 0.1% TFA; UV 210 nm; ODS-3 column 30×500 mm; flow rate 40 mL/min) to afford solution of MC-SAA1(X)-Phe-Cit-APEA-Boc and MC-SAA1-Phe-Cit-APEA-Boc.

Step 6

The solution of MC-SAA1(X)-Phe-Cit-APEA-Boc and MC-SAA1-Phe-Cit-APEA-Boc was treated with concentrated hydrochloric acid (10 eq.). The reaction was monitored by analytical HPLC until the hydrolysis was complete. Acetonitrile was removed under reduced pressure and solid MC-SAA1-Phe-Cit-APEA was obtained after freeze-drying of the aqueous solution. LC-MS: MC-SAA1-Phe-Cit-APEA ($C_{40}H_{54}N_8O_{10}$) required [MH$^+$]=807.4, found [MH$^+$]=809.1.

Step 7

MC-SAA1-Phe-Cit-APEA (110 mg) was dissolved in a mixture of DCM and DMF (10:1, 10 mL) and then auristatin F (93 mg), HBTU (55 mg), and DIPEA (0.077 mL) were added respectively. After 17 hours, DCM, DMF and DIPEA were removed under reduced pressure. The crude product was purified by preparative HPLC (35% acetonitrile in water with 0.1% TFA; UV 210 nm; ODS-3 column 30×250 mm; flow rate 40 mL/min). Acetonitrile in the target fraction was removed under reduced pressure and the remaining aqueous solution was submitted to freeze-drying to afford MHT-47 as white solid (20 mg). LC-MS: MC-SAA1-Phe-Cit-APEA-AF (MHT-47)($C_{80}H_{119}N_{13}O_{17}$) required [MH$^+$]=1534.9, found [MH$^+$]=1538.0.

Preparation Example 2

Synthesis of MHT-71
[MC-SAA1-Val-Cit-APEA-AF]

The linker-toxin MHT-71 was synthesized according to the procedures shown in the following scheme.

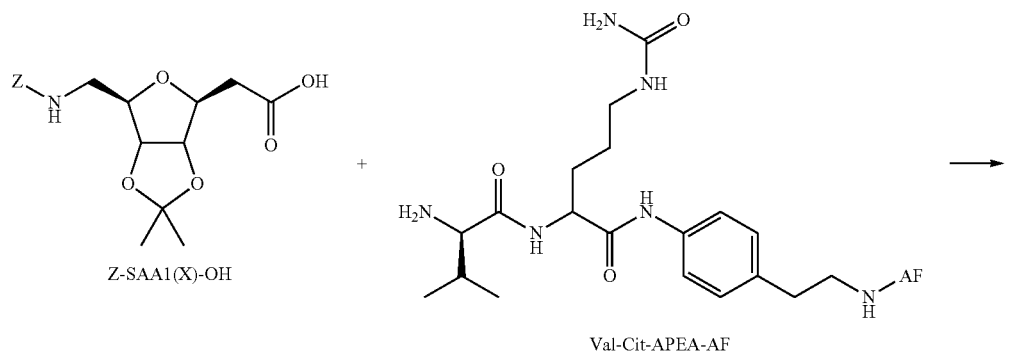

Z-SAA1(X)-OH + Val-Cit-APEA-AF

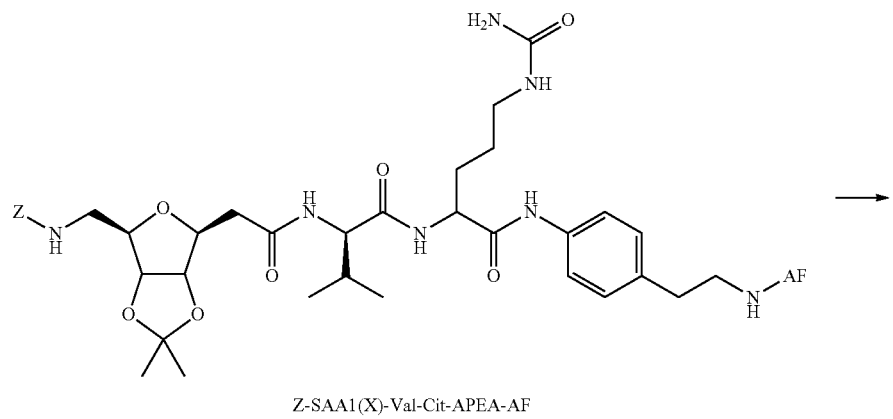

Z-SAA1(X)-Val-Cit-APEA-AF

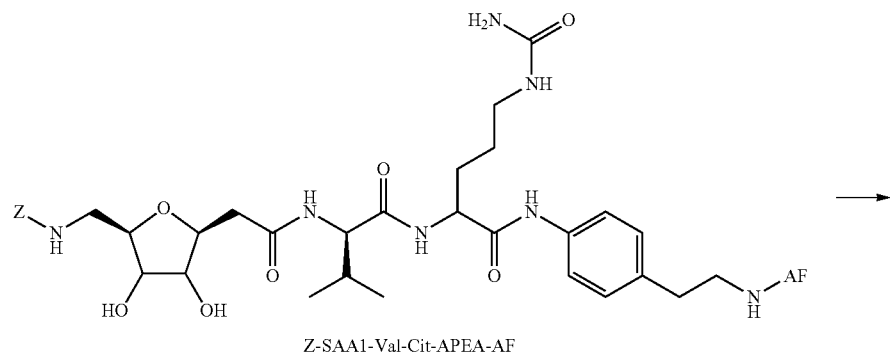

Z-SAA1-Val-Cit-APEA-AF

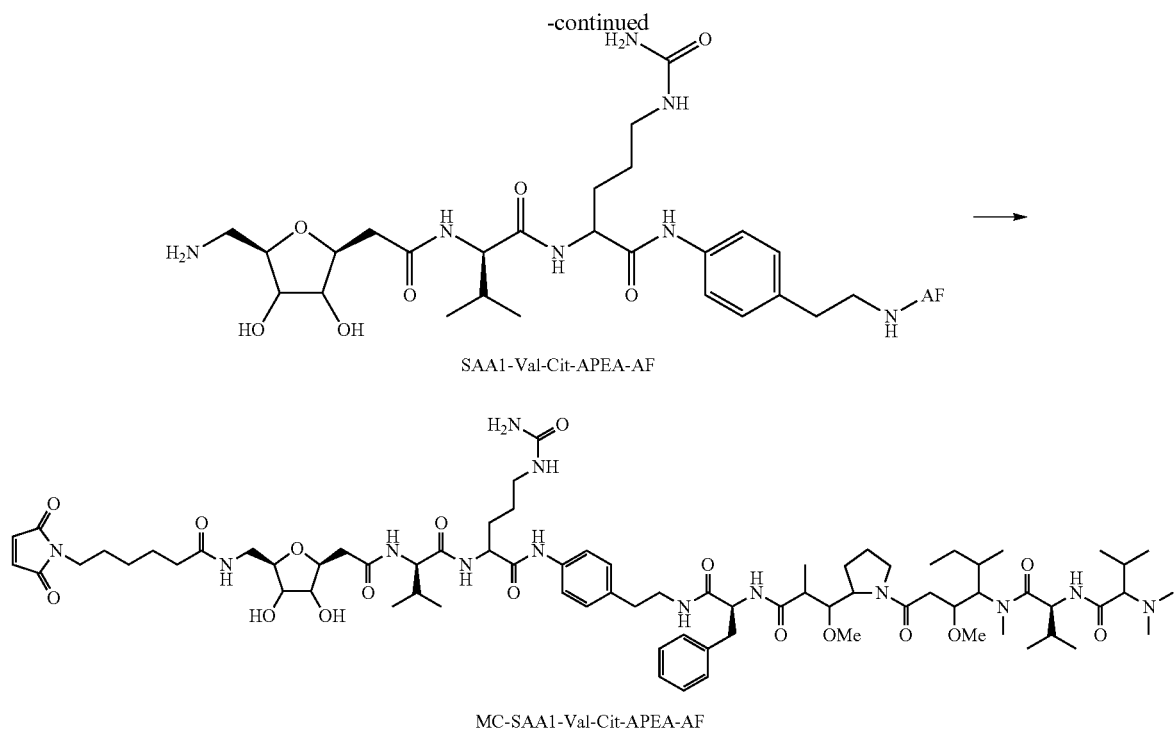

SAA1-Val-Cit-APEA-AF

MC-SAA1-Val-Cit-APEA-AF

Step 1

To a solution of Z-SAA1(X)—OH (26.1 mg) and Val-Cit-APEA-AF (80 mg) in a mixture of DCM and DMF (10:1, 4.4 mL) was added HBTU (32.5 mg) and DIPEA (0.029 mL) respectively. After 18 hours, the solvents were removed under reduced pressure and the crude product was purified by preparative HPLC (45% acetonitrile in water with 0.1% TFA; UV 210 nm; ODS-3 column 30×500 mm; flow rate 65 mL/min; RT 11 min). After the removal of acetonitrile, the aqueous solution was left in a fridge overnight until Z-SAA1(X)-Val-Cit-APEA-AF was completely transformed into Z-SAA1-Val-Cit-APEA-AF. The aqueous solution was then submitted to freeze-drying to afford Z-SAA1-Val-Cit-APEA-AF as white solid (63 mg, 63% yield over two steps).

Step 2

Z-SAA1-Val-Cit-APEA-AF (63 mg) was dissolved in methanol (5 mL) followed by adding Pd/C catalyst. The reaction mixture was then applied a hydrogen balloon and stirred for 3 hours. The Pd/C was filtered off through a pad of celite and then the filtrate was evaporated under reduced pressure to afford SAA1-Val-Cit-APEA-AF as white solid (52.5 mg).

Step 3

To a solution of SAA1-Val-Cit-APEA-AF (40 mg) and MC-OPFP (11.6 mg) in methanol (4 mL) was added DIPEA (0.0056 mL). The reaction was stirred overnight and then evaporated under reduced pressure. The crude product was purified by preparative HPLC (35% acetonitrile in water with 0.1% TFA; UV 210 nm; ODS-3 column 30×500 mm; flow rate 70 mL/min; RT 18 min) to afford MC-SAA1-Val-Cit-APEA-AF (MHT-71) as white solid (27 mg; 47%). LC-MS: MC-SAA1-Val-Cit-APEA-AF (MHT-71) ($C_{76}H_{120}N_{13}O_{17}$) required [MH$^+$]=1486.9, found [MH$^+$]=1487.2.

Preparation Example 3

Synthesis of MHT-81a
[MC-SAA6-Val-Cit-APEA-AF]

The linker-toxin MHT-81a was synthesized according to the procedures shown in the following scheme.

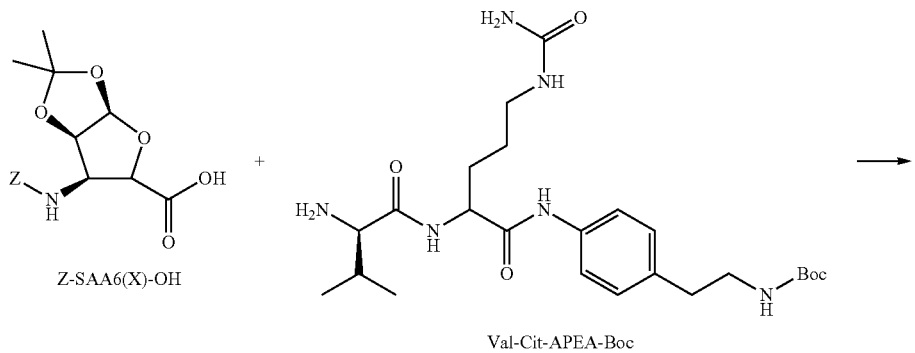

Z-SAA6(X)-OH

Val-Cit-APEA-Boc

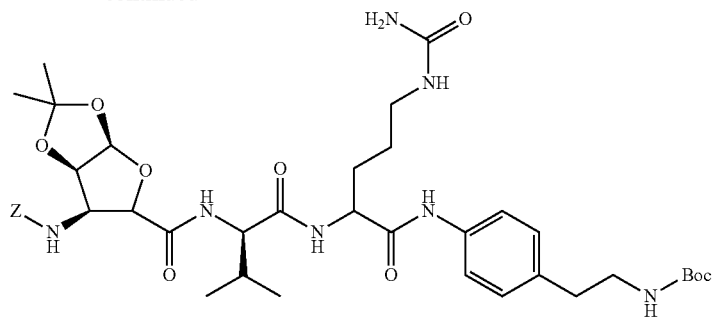
Z-SAA6(X)-Val-Cit-APEA-Boc
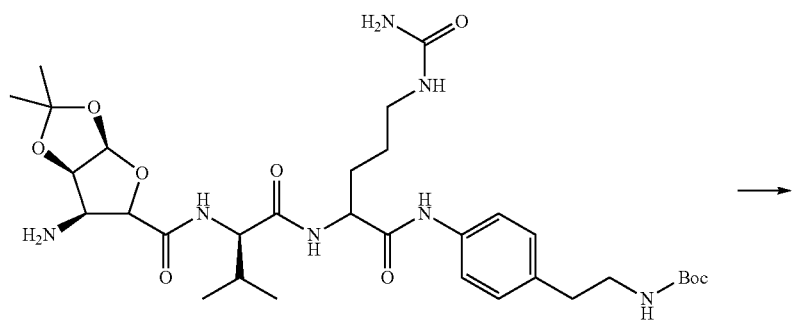
SAA6(X)-Val-Cit-APEA-Boc
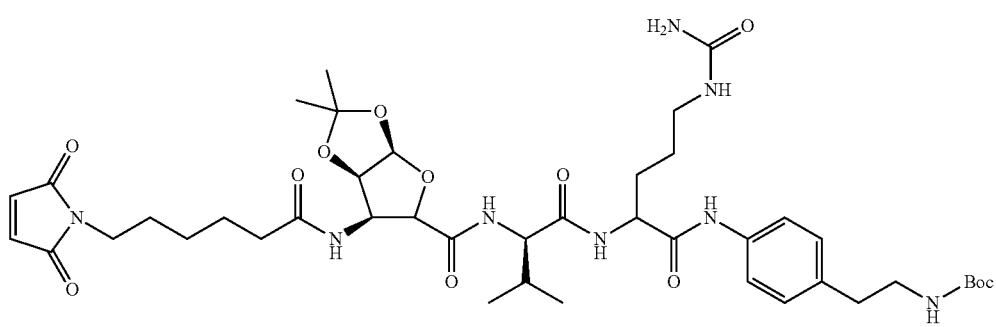
MC-SAA6(X)-Val-Cit-APEA-Boc
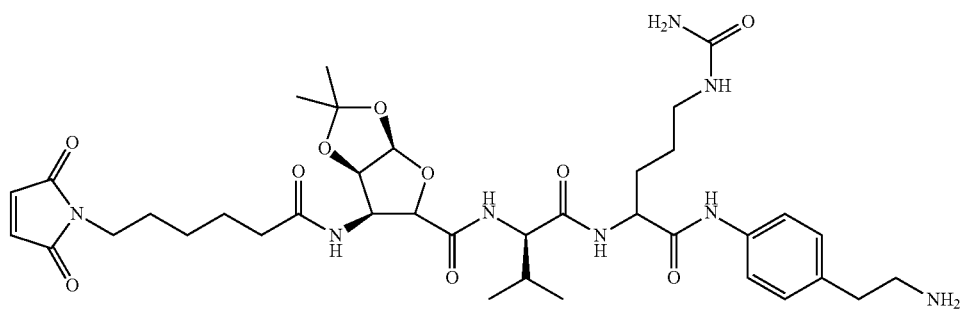
MC-SAA6(X)-Val-Cit-APEA

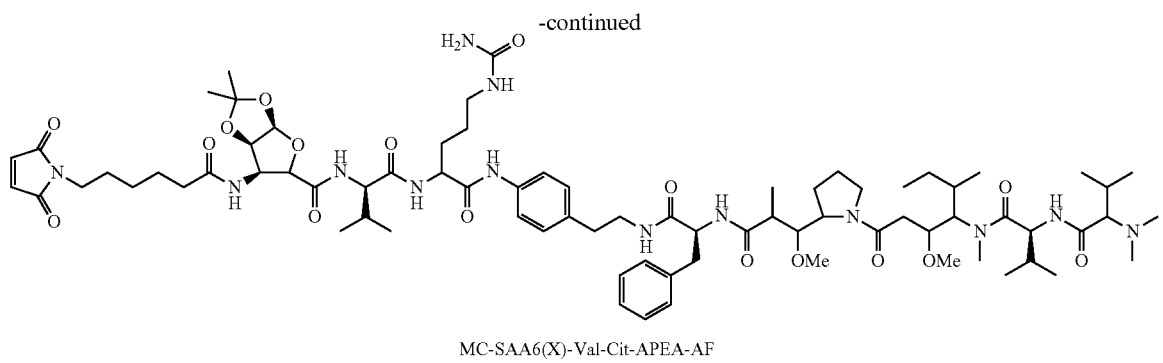

MC-SAA6(X)-Val-Cit-APEA-AF

Step 1

To a solution of Z-SAA6(X)—OH (100 mg) in dichloromethane (10 mL) was added proton sponge (63 mg) and HBTU (170 mg). The solution of Val-Cit-APEA-Boc (150 mg) in DMF (1 mL) was then added and left overnight. After removal of solvents, the crude product was purified by preparative HPLC (50% acetonitrile in water with 0.1% TFA; UV 210 nm; ODS-3 column 30*500 mm; flow rate 70 mL/min; RT 15 min) to afford Z-SAA6(X)-Val-Cit-APEA-Boc as white solid (122.1 mg). LC-MS: Z-SAA6(X)-Val-Cit-APEA-Boc ($C_{40}H_{57}N_7O_{11}$) required [MH$^+$]=812.42, found [MH$^+$]=813.2.

Step 2

Z-SAA6(X)-Val-Cit-APEA-Boc (50 mg) was dissolved in methanol (2 mL) followed by addition catalyst Pd/C. The reaction mixture was then applied a hydrogen balloon and left for 17 hours. The catalyst Pd/C was filtered off through a pad of celite, and the methanol was evaporated under reduced pressure to afford SAA6(X)-Val-Cit-APEA-Boc as white solid (37.4 mg).

Step 3

SAA6(X)-Val-Cit-APEA-Boc (47 mg) and MC-OPFP (28 mg) were dissolved in DMF (4 mL). DIPEA (0.0141 mL) was added to the reaction mixture. After 5 hours, DMF and DIPEA were removed under reduced pressure. The crude product was purified by preparative HPLC (50% acetonitrile in water with 0.1% TFA; UV 210 nm; ODS-3 column 30*500 mm; flow rate 45-50 mL/min; RT 10.8 min) to afford MC-SAA6(X)-Val-Cit-APEA-Boc as white solid (42.5 mg). LC-MS: MC-SAA6(X)-Val-Cit-APEA-Boc ($C_{42}H_{62}N_8O_{12}$) required [MH$^+$]=871.46, found [MH$^+$]=871.5.

Step 4

MC-SAA6(X)-Val-Cit-APEA-Boc (42.5 mg) in DCM (10 mL) was treated with TFA (0.1 mL) at room temperature. After 17 hours, the DCM and TFA were removed under reduced pressure and a light yellow solid MC-SAA6(X)-Val-Cit-APEA was obtained (40 mg). LC-MS: MC-SAA6(X)-Val-Cit-APEA ($C_{37}H_{54}N_8O_{10}$) required [MH$^+$]=771.40, found [MH$^+$]=771.9.

Step 5

MC-SAA6(X)-Val-Cit-APEA (32 mg) and auristatin F (27 mg) were dissolved in a mixture of DCM and DMF (10:1, 12 mL). Then, HBTU (20.5 mg) and DIPEA (0.022 mL) were added respectively. After 17 hours, DCM and DMF were removed under reduced pressure. The crude product was purified by preparative HPLC (40% acetonitrile in water with 0.1% TFA; UV 210 nm; ODS-3 column 30*500 mm; flow rate 30 mL/min) to afford MC-SAA6(X)-Val-Cit-APEA-AF as white solid (15 mg). LC-MS: MC-SAA6(X)-Val-Cit-APEA-AF ($C_{77}H_{119}N_{13}O_{17}$) required [MH$^+$]=1498.89, found [MH$^+$]=1500.7.

Preparation Example 4

Synthesis of MHT-93
[MC-SAA7-Val-Cit-APEA-AF]

The linker-toxin MHT-93 was synthesized according to the procedures shown in the following scheme.

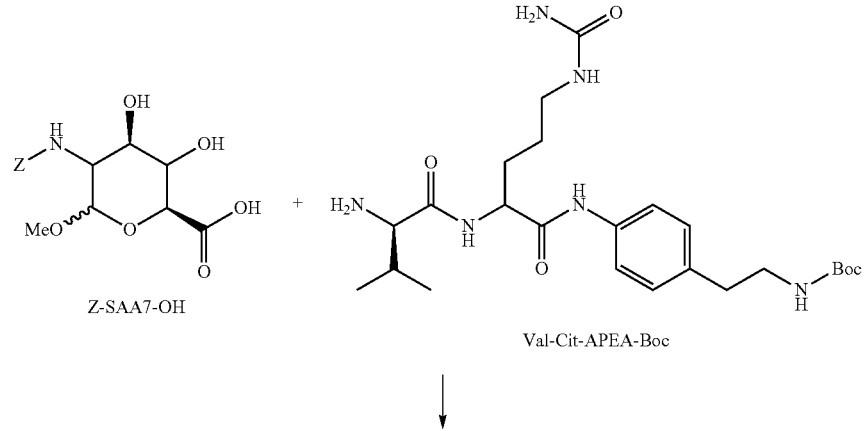

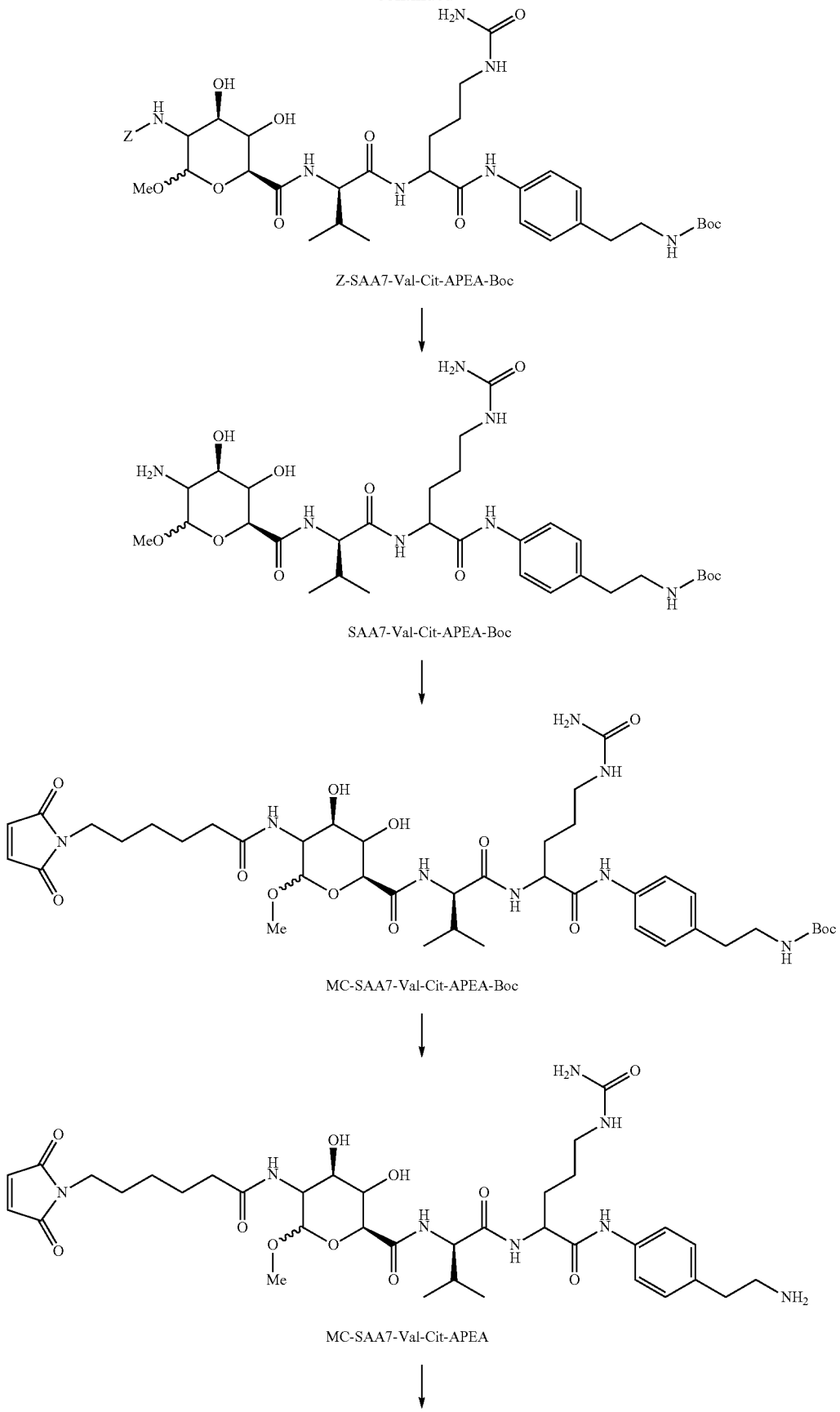

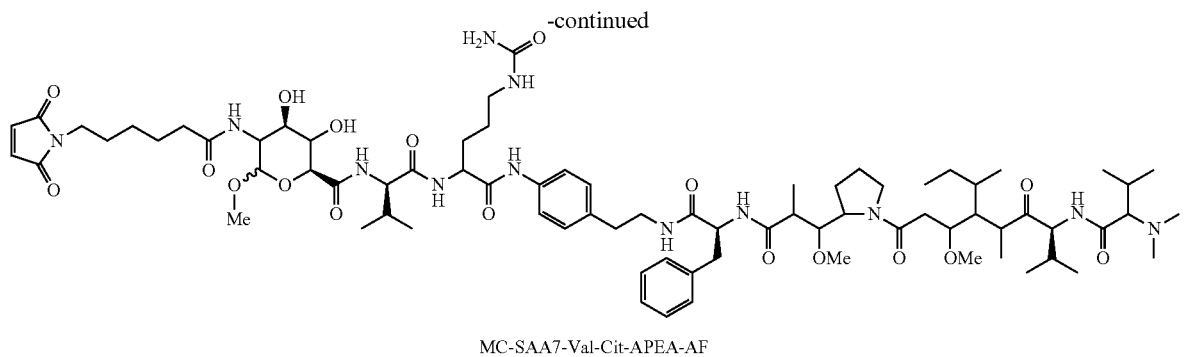

MC-SAA7-Val-Cit-APEA-AF

Step 1

Val-Cit-APEA-Boc (2.46 g, 5 mmol) and Z-SAA7-OH (1.71 g, 5 mmol) were dissolved in DMF (100 mL). Then, DIPEA (646.2 mg, 5 mmol) and HATU (1.90 g, 5 mmol) were added to the reaction mixture. After the mixture was stirred at room temperature for 16 hours, the solvent was evaporated under reduced pressure. The residue was stirred with ethyl acetate (200 mL) for several hours until a fine white powder formed. The solid product was filtered off. The white powder was boiled in water (200 mL) for 15 minutes and then filtered while hot. The product was washed with hot water (50 mL, 2 times) and finally dried under vacuum to afford Z-SAA7-Val-Cit-APEA-Boc.

Step 2

Z-SAA7-Val-Cit-APEA-Boc (200 mg) was dissolved in methanol (50 mL) followed by addition of catalyst Pd/C. The reaction was then applied a hydrogen balloon and left for 17 hours. The catalyst was filtered off through a pad of celite. The methanol was evaporated under reduced pressure to afford SAA7-Val-Cit-APEA-Boc was obtained as white solid (148 mg).

Step 3

SAA7-Val-Cit-APEA-Boc (240 mg), MC-OPFP (144 mg) and DIPEA (0.072 mL) were dissolved in DMF (20 mL). After 5 hours, DMF and DIPEA were removed under reduced pressure. The residue was mixed with 45% acetonitrile in H$_2$O (20 mL) and then centrifuged. After the removal of the liquid part, MC-SAA7-Val-Cit-APEA-Boc was obtained as white solid (200 mg). LC-MS: MC-SAA7-Val-Cit-APEA-Boc (C$_{41}$H$_{62}$N$_8$O$_{13}$) required [MH$^+$]=875.45, found [MH$^+$]=875.8.

Step 4

MC-SAA7-Val-Cit-APEA-Boc (200 mg) in DCM (30 mL) was treated with TFA (0.5 mL) at room temperature. After 17 hours, DCM and TFA were removed under reduced pressure and a light yellow solid MC-SAA7-Val-Cit-APEA was obtained (180 mg). LC-MS: MC-SAA7-Val-Cit-APEA (C$_{36}$H$_{54}$N$_8$O$_{11}$) required [MH$^+$]=775.4, found [MH$^+$]=776.0.

Step 5

MC-SAA7-Val-Cit-APEA (80 mg) and auristatin F (77 mg) were dissolved in a mixture of DCM and DMF (10:1, 16.6 mL). Then, HBTU (64 mg) and DIPEA (0.064 mL) were added respectively. After 17 hours, DCM and DMF were removed under reduced pressure. The crude product was purified by preparative HPLC (40% acetonitrile in water with 0.1% TFA; UV 210 nm; ODS-3 column 30*250 mm; flow rate 25 mL/min; RT 10.42 min) to afford MC-SAA7-Val-Cit-APEA-AF (MHT-93) as white solid (50.9 mg). LC-MS: MC-SAA7-Val-Cit-APEA-AF (MHT-93) (C$_{77}$H$_{120}$N$_{12}$O$_{18}$) required [MH$^+$]=1503.0, found [MH$^+$]=1504.1.

Preparation Example 5

Synthesis of MHT-98a
[MC-SAA8-Val-Cit-APEA-AF]

The linker-toxin MHT-98a was synthesized according to the procedures shown in the following scheme.

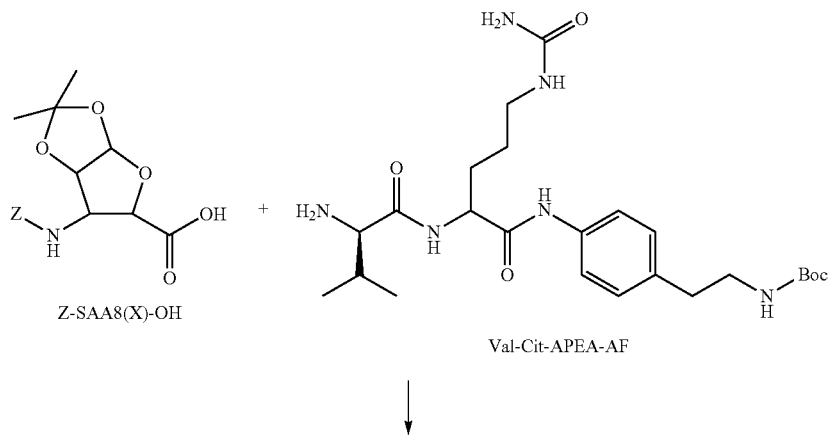

Z-SAA8(X)-OH         Val-Cit-APEA-AF

-continued
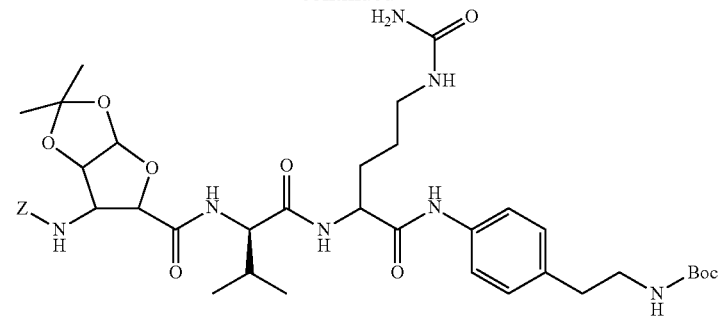
Z-SAA8-Val-Cit-APEA-AF
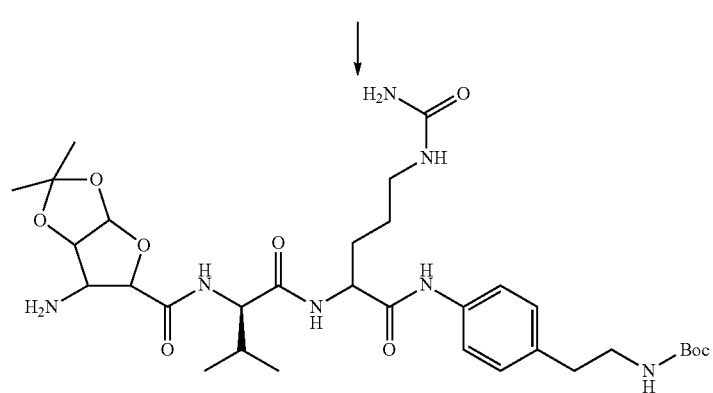
SAA8-Val-Cit-APEA-Boc
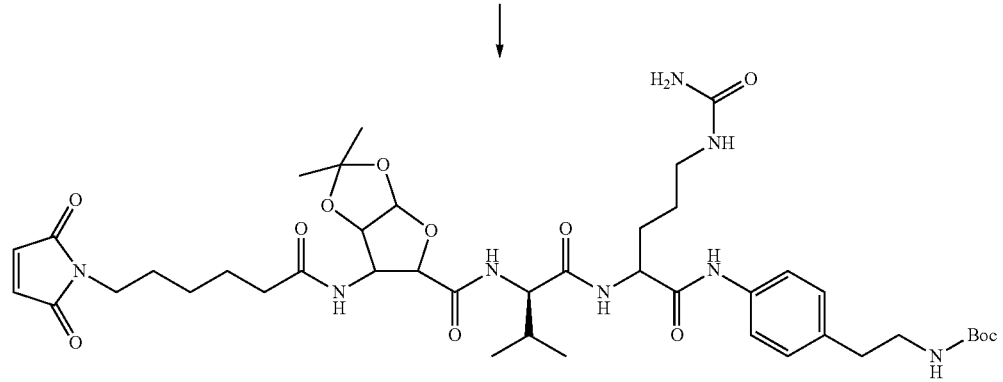
MC-SAA8-Val-Cit-APEA-Boc
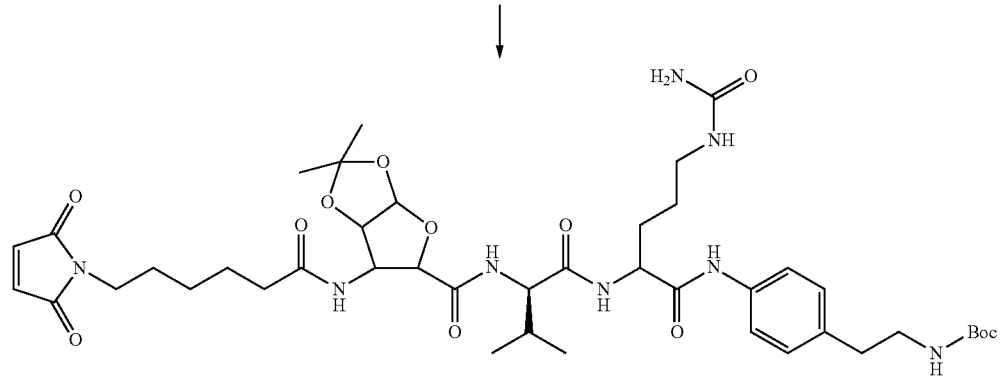
MC-SAA8-Val-Cit-APEA-Boc

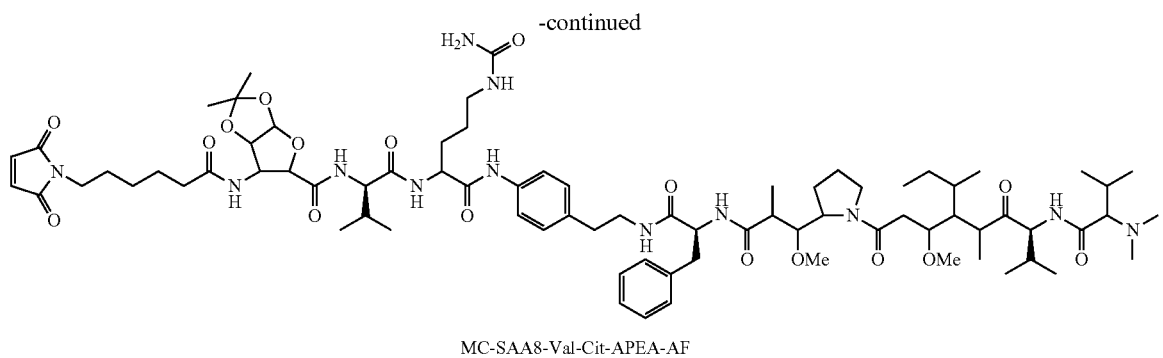

MC-SAA8-Val-Cit-APEA-AF

Step 1

To a solution of Z-SAA8(X)—OH (100 mg) in DCM (10 mL) was added proton sponge (63 mg) and HBTU (170 mg). The solution of Val-Cit-APEA-Boc (150 mg) in DMF (1 mL) was then added and the reaction mixture was left overnight. After removal of solvents, the residue was purified by preparative HPLC (55% acetonitrile in water with 0.1% TFA; UV 210 nm; ODS-3 column 30*500 mm; flow rate 60 mL/min; RT 13 min) to afford Z-SAA8(X)-Val-Cit-APEA-Boc as white solid (144.6 mg). LC-MS: Z-SAA8(X)-Val-Cit-APEA-Boc ($C_{40}H_{57}N_7O_{11}$) required [$MH^+$]=812.4, found [$MH^+$]=813.4.

Step 2

Z-SAA8(X)-Val-Cit-APEA-Boc (70 mg) was dissolved in MeOH (10 mL) followed by addition of the catalyst Pd/C. The reaction was then applied a hydrogen balloon and left for 17 hours. Then, the catalyst was filtered through a pad of celite. The filtrate was evaporated under reduced pressure to afford SAA8(X)-Val-Cit-APEA-Boc as white solid (54 mg).

Step 3

SAA8(X)-Val-Cit-APEA-Boc (44 mg) and MC-OPFP (24.2 mg) were dissolved in DMF (4 mL) and then DIPEA (0.0141 mL) was added. After 5 hours, DMF and DIPEA were removed under reduced pressure and the residue was purified by preparative HPLC (45% acetonitrile in water with 0.1% TFA; UV 210 nm; ODS-3 column 30*250 mm; flow rate 35-40 mL/min; RT 13 min) to afford MC-SAA8 (X)-Val-Cit-APEA-Boc as white solid (40 mg). LC-MS: MC-SAA8(X)-Val-Cit-APEA-Boc ($C_{42}H_{62}N_8O_{12}$) required [$MH^+$]=871.5, found [$MH^+$]=872.0.

Step 4

MC-SAA8(X)-Val-Cit-APEA-Boc (40 mg) in DCM (2 mL) was treated with TFA (0.1 mL) at room temperature. After 17 hours, DCM and TFA were removed under reduced pressure and a light yellow solid MC-SAA8(X)-Val-Cit-APEA was obtained (40 mg). LC-MS: MC-SAA8(X)-Val-Cit-APEA ($C_{37}H_{54}N_8O_{10}$) required [$MH^+$]=771.4, found [$MH^+$]=771.9.

Step 5

MC-SAA8(X)-Val-Cit-APEA (25.6 mg) and auristatin F (24.5 mg) were dissolved in a mixture of DCM and DMF (10:1, 5.5 mL). Then, HBTU (20.5 mg) and DIPEA (0.022 mL) were added respectively. After 17 hours, DCM and DMF were removed under reduced pressure. The residue was purified by preparative HPLC (40% acetonitrile in water with 0.1% TFA; UV 210 nm; ODS-3 column 30*250 mm; flow rate 35-40 mL/min) to afford compound MC-SAA8 (X)-Val-Cit-APEA-AF (MHT-98a) as white solid (3.3 mg). LC-MS: MC-SAA8(X)-Val-Cit-APEA-AF (MHT-98a) ($C_{78}H_{120}N_{12}O_{17}$) required [$MH^+$]=1497.9, found [$MH^+$]=1500.5.

Preparation Example 6

Synthesis of CCH-028
[MC-SAA1-Val-Cit-APEA(COOMe)-AF]

The linker-toxin CCH-028 was synthesized according to the procedures shown in the following scheme.

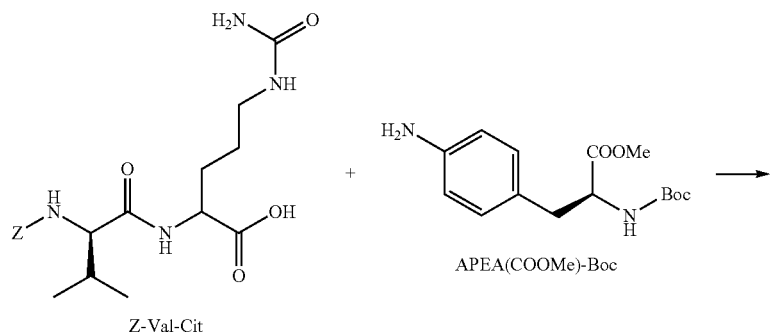

-continued
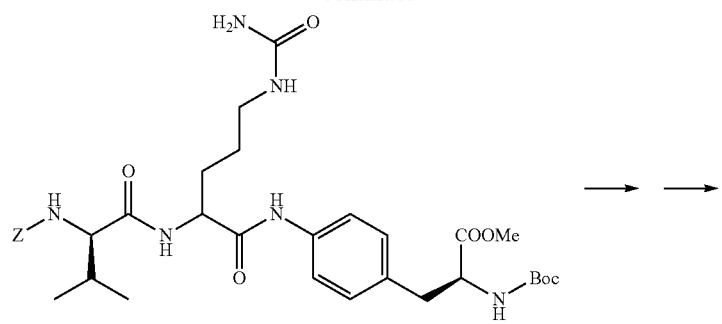
Z-Val-Cit-APEA(COOMe)-Boc
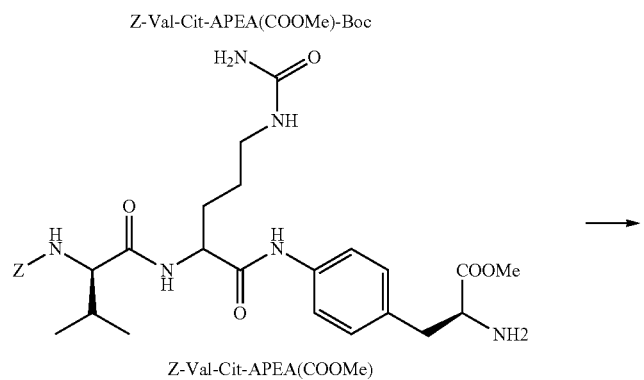
Z-Val-Cit-APEA(COOMe)
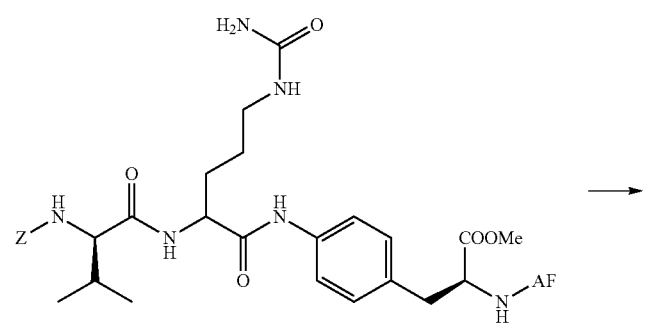
Z-Val-Cit-APEA(COOMe)-AF
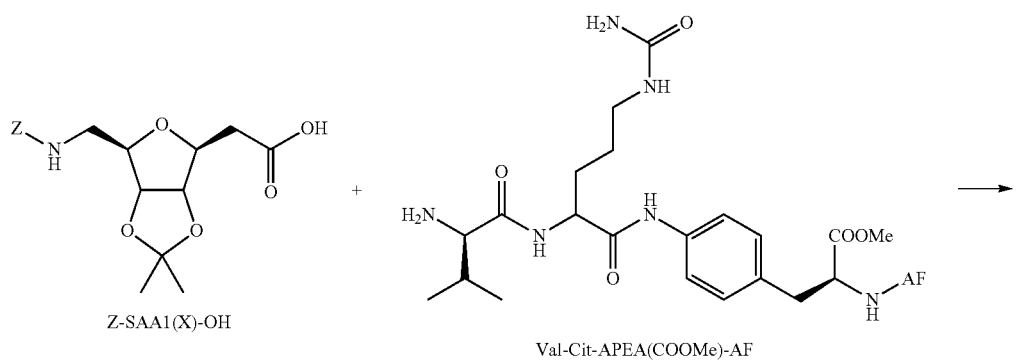

-continued

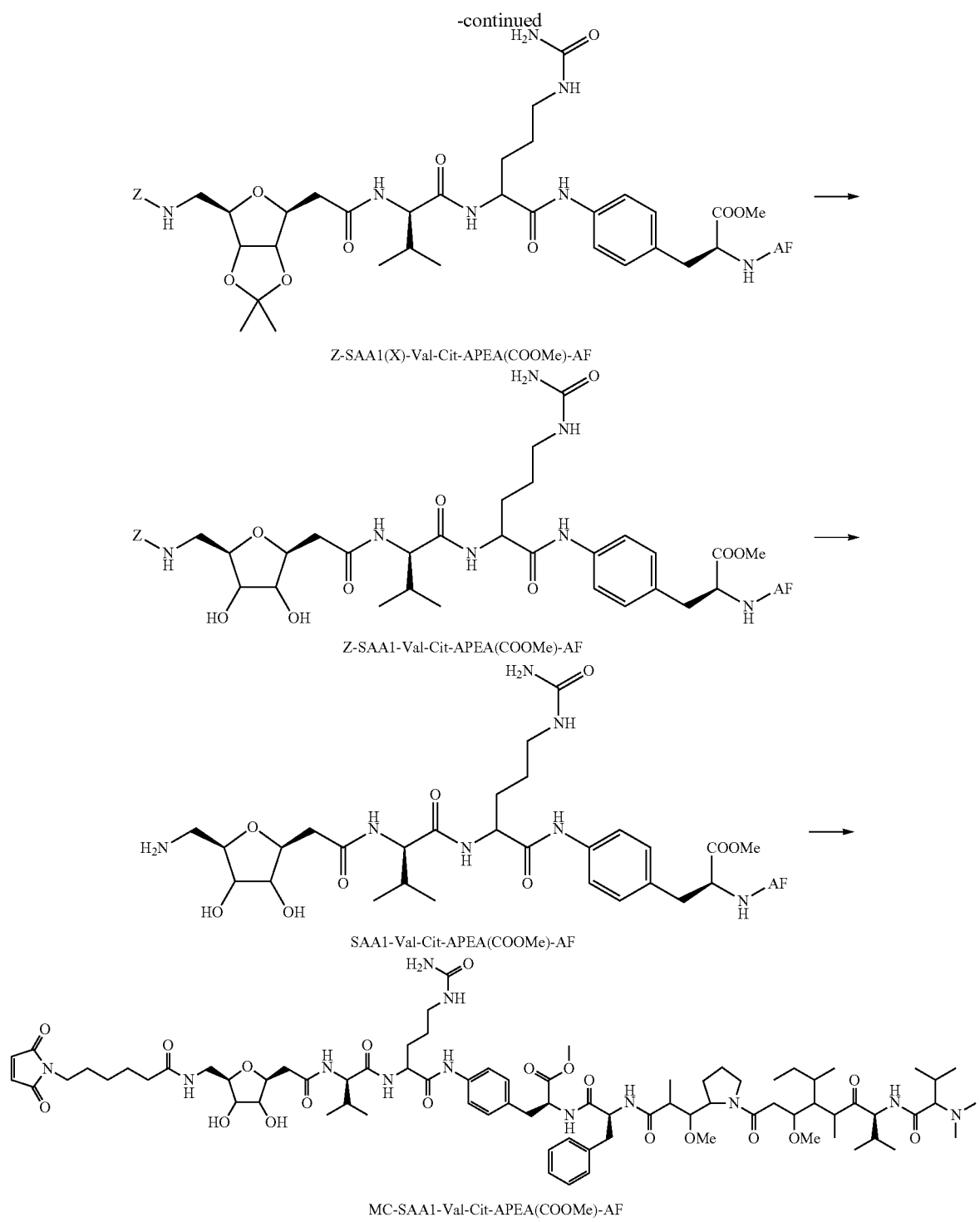

Z-SAA1(X)-Val-Cit-APEA(COOMe)-AF

Z-SAA1-Val-Cit-APEA(COOMe)-AF

SAA1-Val-Cit-APEA(COOMe)-AF

MC-SAA1-Val-Cit-APEA(COOMe)-AF

Step 1

Z-Val-Cit-OH (3.24 g, 7.93 mmol) was added into a mixture of dichloromethane and methanol (3:1, 80 mL). After APEA(COOMe)-Boc (2.8 g, 9.52 mmol) was added, the coupling reagent EEDQ (2.47 g, 9.52 mmol) was charged. The turbid solution was stirred at room temperature. The undissolved Z-Val-Cit was gradually disappeared and the solution gradually became clear. After 48 hours, the reaction was complete when checked with HPLC. The reaction mixture was evaporated under reduced pressure until a thick paste formed. The mixture was filtered off, washed with n-hexane (50 mL, 2 times), water (50 mL, 2 times) and diethyl ether (50 mL, 2 times). The solid product was finally dried under vacuum to afford Z-Val-Cit-APEA (COOMe)-Boc as brown powder (75.0 mg, 1.4%).

Step 2

Z-Val-Cit-APEA(COOMe)-Boc (75.0 mg, 0.11 mmol) was added into dichloromethane (8 mL) and then treated with trifluoroacetic acid (0.09 mL) at room temperature. After 4 hours, the solvent was evaporated under reduced pressure. The residue was mixed with water (10 mL) and submitted to freeze-drying to afford Z-Val-Cit-APEA (COOMe) as white powder (96.0 mg).

Step 3

Auristatin F (80.0 mg, 0.102 mmol) was dissolved in small amount of DMF (1 mL) and then diluted with DCM (10 mL). The solution was immersed in an ice-bath and then Z-Val-Cit-APEA(COOMe) (71.4 mg, 0.102 mmol) and HATU (43.0 mg, 0.113 mmol) were charged. After DIPEA (0.071 mL) was added, the ice-bath was removed. After the mixture was stirred at room temperature for 4 hours, the solvents were evaporated under reduced pressure and the residue was purified by preparative HPLC (43% acetonitrile in water with 0.1% TFA; UV 210 nm; ODS-3 column 30*250 mm; flow rate 24 mL/min) to afford Z-Val-Cit-APEA(COOMe)-AF as white solid (82.0 mg, 61%).

Step 4

Z-Val-Cit-APEA(COOMe)-AF (82.0 mg, 0.062 mmol) was dissolved in ethanol (10 mL) containing hydrochloric acid (0.24 mmol). After Pd/C (10%, 10 mg) was charged, the reaction mixture was applied a hydrogen balloon and stirred overnight. The catalyst Pd/C was filtered off through a pad of celite and then the filtrate was evaporated under reduced pressure. The residue was mixed with water (10 mL) and submitted to freeze-drying to afford Val-Cit-APEA (COOMe)-AF as white powder (72.8 mg, 96%). LC-MS: Val-Cit-APEA(COOMe)-AF ($C_{61}H_{99}N_{11}O_{12}$) required [MH$^+$]=1178.8, found [MH$^+$]=1179.7.

Step 5

Z-SAA1(X)—OH (22.0 mg, 0.06 mmol) was dissolved in dichloromethane (10 mL). After HATU (25.3 mg, 0.066 mmol) was added, the reaction mixture was immersed in an ice-bath followed by adding DIPEA (0.032 mL, 0.06 mmol). After 10 minutes, the ice-bath was removed and a solution of Val-Cit-APEA(COOMe)-AF (72.8 mg, 0.06 mmol) in DMF (3 mL) was added to the reaction mixture at room temperature. After 3 hours, the solvents were evaporated under reduced pressure and the crude product was purified by preparative HPLC (45% acetonitrile in water with 0.1% TFA; UV 210 nm; ODS-3 column 30×250 mm; flow rate 24 mL/min). After the removal of acetonitrile, the aqueous solution was left at room temperature overnight to allow the Z-SAA1(X)-Val-Cit-APEA(COOMe)-AF completely hydrolyzed. The aqueous solution was then submitted to freeze-drying to afford Z-SAA1-Val-Cit-APEA(COOMe)-AF as white solid (43.5 mg, 49% yield over two steps). LC-MS: Z-SAA1-Val-Cit-APEA(COOMe)-AF ($C_{79}H_{120}N_{12}O_{18}$) required [MH$^+$]=1525.9, found [MH$^+$]=1526.8.

Step 6

Z-SAA1-Val-Cit-APEA(COOMe)-AF (43.5 mg, 0.029 mmol) was dissolved in ethanol (5 mL) containing hydrochloric acid (0.06 mmol). After Pd/C (10%, 4.7 mg) was charged, the reaction mixture was applied a hydrogen balloon and stirred overnight. The catalyst Pd/C was filtered off through a pad of celite and then the filtrate was evaporated under reduced pressure. The residue was mixed with water (5 mL) and submitted to freeze-drying to afford SAA1-Val-Cit-APEA(COOMe)-AF as white powder (38.4 mg, 94%).

Step 7

To a solution of SAA1-Val-Cit-APEA(COOMe)-AF (15.0 mg, 0.011 mmol) and MC-OPFP (4.5 mg, 0.012 mmol) in DMF (4 mL) was added DIPEA (0.004 mL). The mixture was stirred at room temperature for 1 hour and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA1-Val-Cit-APEA (COOMe)-AF as white solid (10.0 mg; 60%). LC-MS: MC-SAA1-Val-Cit-APEA(COOMe)-AF ($C_{78}H_{121}N_{13}O_{19}$) required [MH$^+$]=1544.9, found [MH$^+$]=1545.8.

Preparation Example 7

Synthesis of CCH-035
[MC-SAA3-Val-Cit-APEA-AF]

The linker-toxin CCH-035 was synthesized according to the procedures shown in the following scheme.

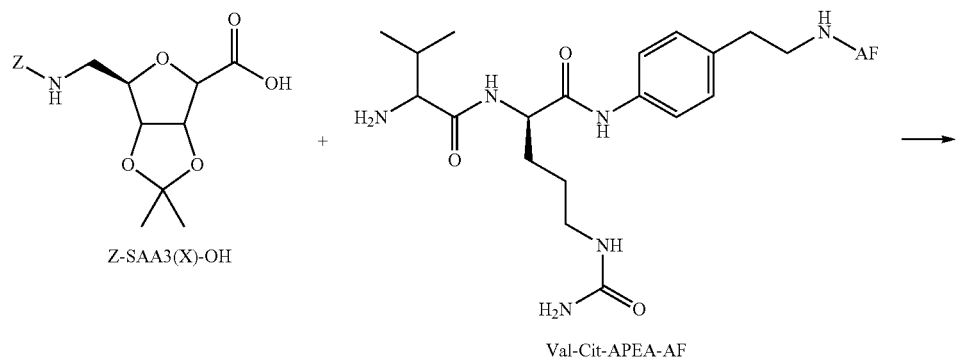

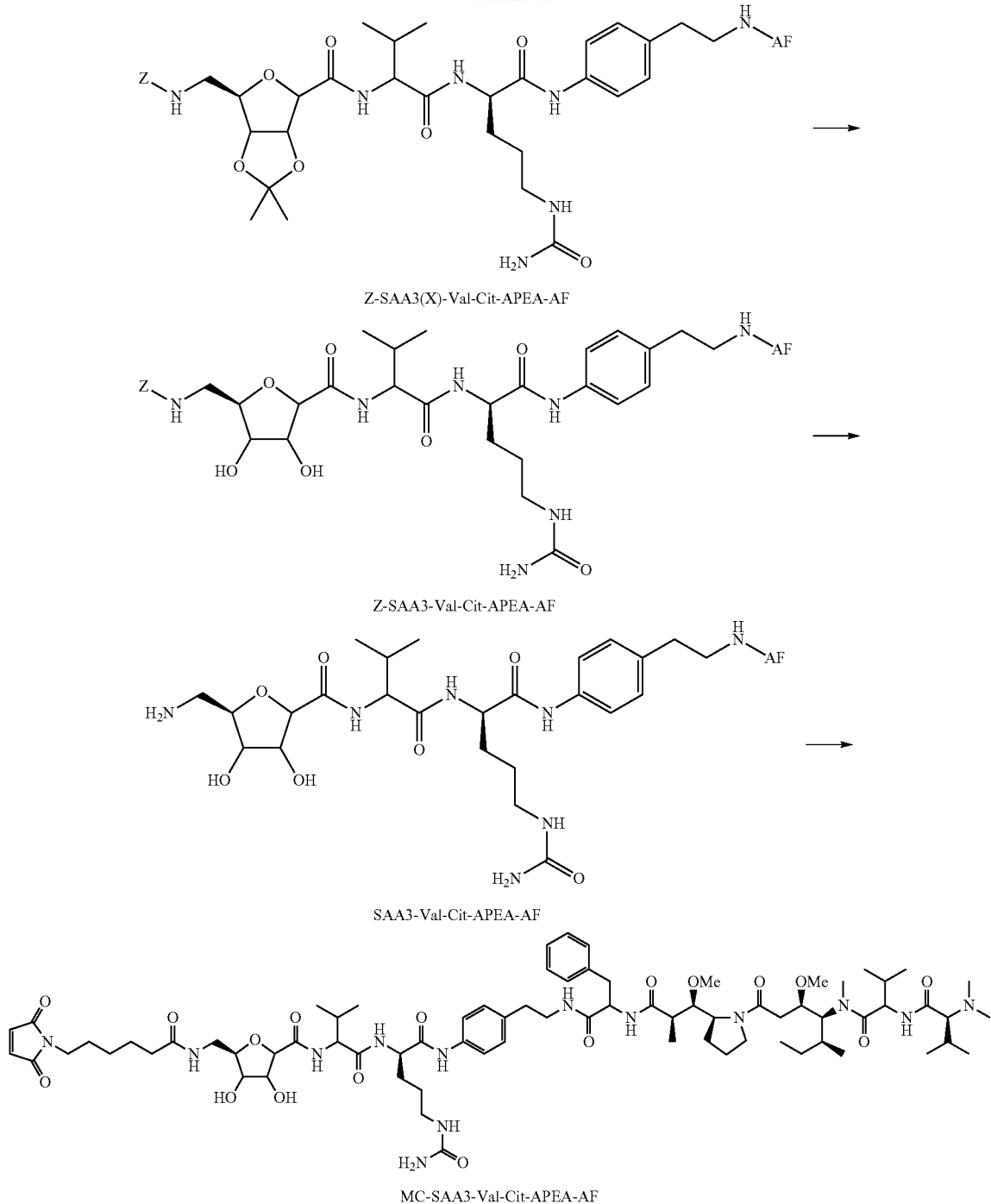

Z-SAA3(X)-Val-Cit-APEA-AF

Z-SAA3-Val-Cit-APEA-AF

SAA3-Val-Cit-APEA-AF

MC-SAA3-Val-Cit-APEA-AF

Step 1

To a solution of Z-SAA3(X)—OH (18.2 mg, 0.052 mmol) and Val-Cit-APEA-AF (60.0 mg, 0.052 mmol) in a mixture of DCM and DMF (10:1, 6 mL) was added HATU (22.0 mg, 0.0572 mmol) and DIPEA (0.027 mL, 0.156 mmol) respectively. After 18 hours, the solvents were removed under reduced pressure and the crude product was purified by preparative HPLC (43% acetonitrile in water with 0.1% TFA; UV 210 nm; ODS-3 column 30×250 mm; flow rate 24 mL/min). After the removal of acetonitrile, the aqueous solution was stood at room temperature overnight until the acetonide group was completely deprotected removed. The aqueous solution was subjected to freeze-drying to afford Z-SAA3-Val-Cit-APEA-AF as white solid (48.0 mg, 65% yield over two steps).

Step 2

Z-SAA3-Val-Cit-APEA-AF (48.0 mg, 0.034 mmol) was dissolved in ethanol (5 mL) containing hydrochloric acid (0.014 mL). After Pd/C (10%, 4.7 mg) was charged, the reaction mixture was applied a hydrogen balloon and stirred for 5 hours. The catalyst Pd/C was filtered off through a pad of celite and then the filtrate was evaporated under reduced pressure. The product was mixed with water (5 mL) and submitted to freeze-drying to afford SAA3-Val-Cit-APEA-AF as white solid (42.0 mg, 94%).

Step 3

To a solution of SAA3-Val-Cit-APEA-AF (20.0 mg, 0.015 mmol) and MC-OPFP (6.3 mg, 0.0165 mmol) in DMF (4 mL) was added DIPEA (0.006 mL). The reaction was stirred at room temperature for 1 hour and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA3-Val-Cit-APEA-AF as white solid (12.2 mg; 55%). LC-MS: MC-SAA3-Val-Cit-APEA-AF ($C_{75}H_{117}N_{13}O_{17}$) required [MH$^+$]=1473.8, found [MH$^+$]= 1473.6.

Preparation Example 8

Synthesis of CCH-038
[MC-SAA4-Val-Cit-APEA-AF]

The linker-toxin CCH-038 was synthesized according to the procedures shown in the following scheme.

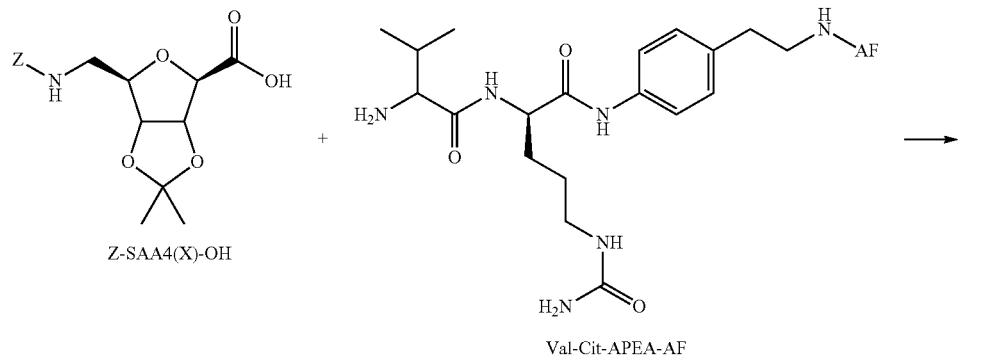

Z-SAA4(X)-OH + Val-Cit-APEA-AF

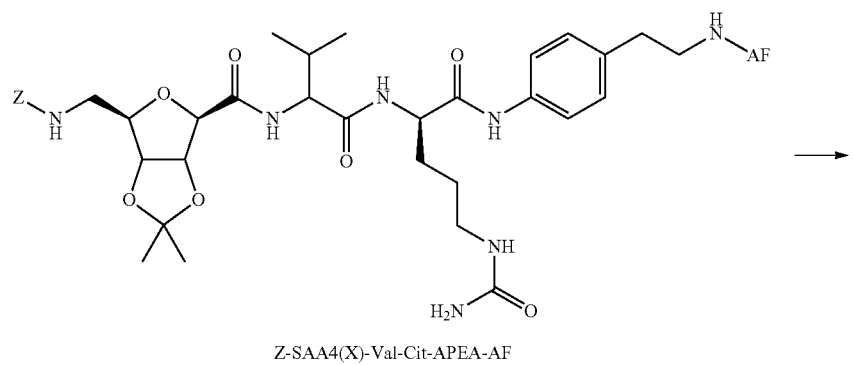

Z-SAA4(X)-Val-Cit-APEA-AF

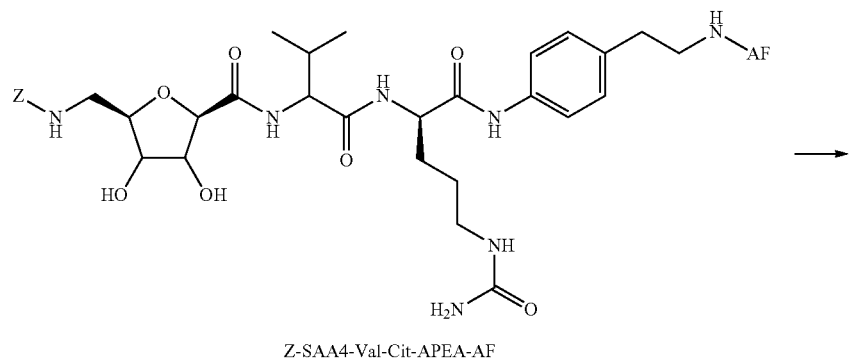

Z-SAA4-Val-Cit-APEA-AF

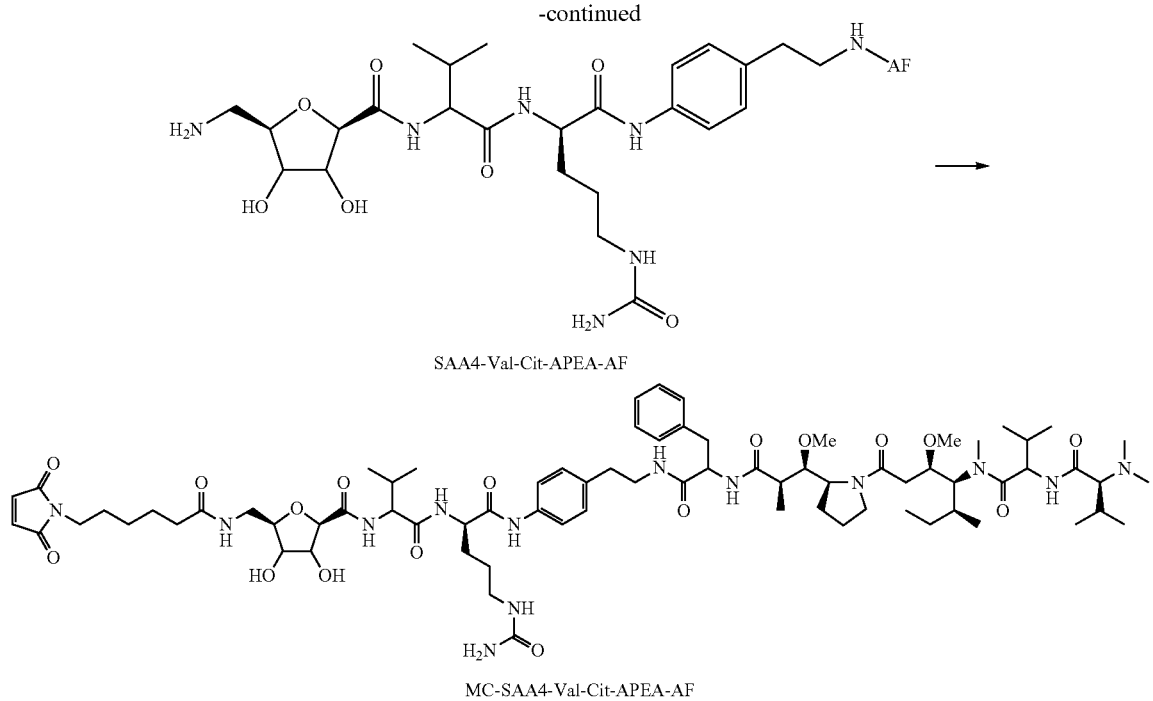

SAA4-Val-Cit-APEA-AF

MC-SAA4-Val-Cit-APEA-AF

Step 1

To a solution of Z-SAA4(X)—OH (15.2 mg, 0.043 mmol) and Val-Cit-APEA-AF (50.0 mg, 0.043 mmol) in a mixture of DCM and DMF (10:1, 6 mL) was added HATU (18.1 mg, 0.0473 mmol) and DIPEA (0.023 mL, 0.129 mmol) respectively. After 18 hours, the solvents were removed under reduced pressure and the crude product was purified by preparative HPLC (43% acetonitrile in water with 0.1% TFA; UV 210 nm; ODS-3 column 30×250 mm; flow rate 24 mL/min). After the removal of acetonitrile, the aqueous solution was stood at room temperature overnight until the removal of acetonide was complete. The aqueous solution was submitted to freeze-drying to afford Z-SAA3-Val-Cit-APEA-AF as white solid (32.4 mg, 53% yield over two steps).

Step 2

Z-SAA3-Val-Cit-APEA-AF (32.4 mg, 0.0229 mmol) was dissolved in ethanol (5 mL) containing hydrochloric acid (0.09 mmol). After Pd/C (10%, 4.0 mg) was charged, the reaction mixture was applied a hydrogen balloon and stirred for 5 hours. The catalyst Pd/C was filtered off through a pad of celite and then the filtrate was evaporated under reduced pressure. The product was mixed with water (5 mL) and submitted to freeze-drying to afford SAA4-Val-Cit-APEA-AF as white solid (30.0 mg, 98%).

Step 3

To a solution of SAA4-Val-Cit-APEA-AF (20.0 mg, 0.015 mmol) and MC-OPFP (6.3 mg, 0.0165 mmol) in DMF (4 mL) was added DIPEA (0.006 mL). The reaction was stirred at room temperature for 1 hour and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA4-Val-Cit-APEA-AF as white solid (15.6 mg; 70%). LC-MS: MC-SAA4-Val-Cit-APEA-AF (CCH-038) ($C_{75}H_{117}N_{13}O_{17}$) required [MH$^+$]=1473.8, found [MH$^+$]=1473.6.

Preparation Example 9

Synthesis of CCH-041
[MC-SAA3-SAA3-Val-Cit-APEA-AF]

The linker-toxin CCH-041 was synthesized according to the procedures shown in the following scheme.

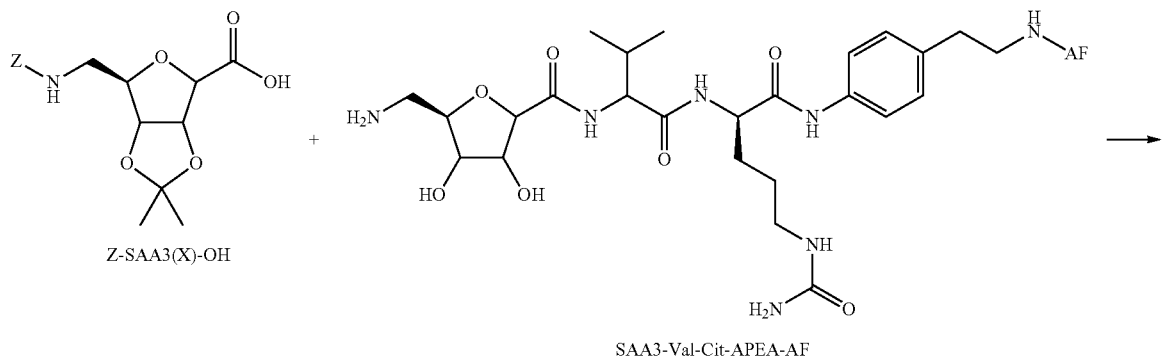

Z-SAA3(X)-OH

SAA3-Val-Cit-APEA-AF

-continued

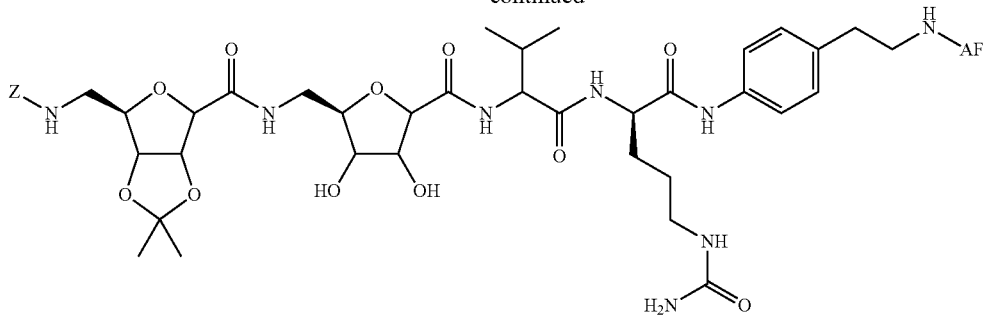

Z-SAA3(X)-Val-Cit-APEA-AF

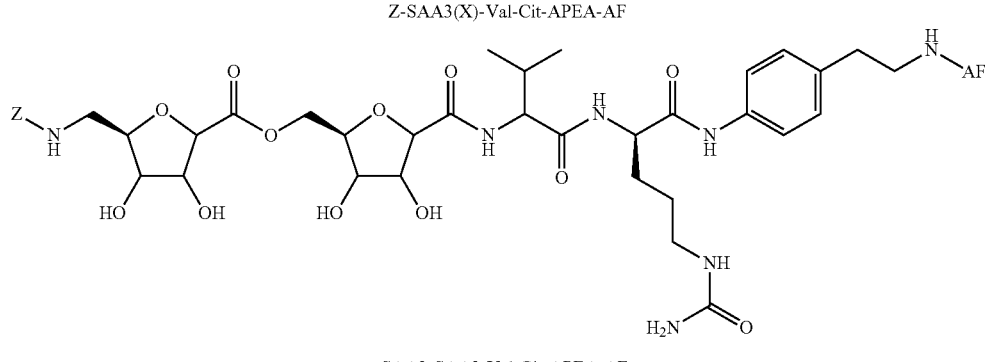

SAA3-SAA3-Val-Cit-APEA-AF

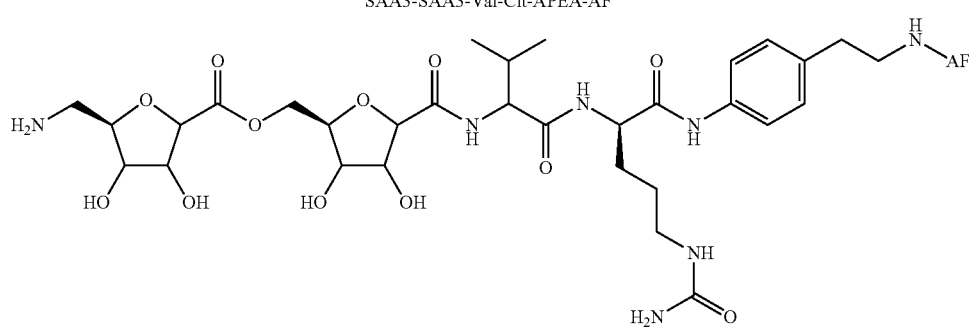

SAA3-SAA3-Val-Cit-APEA-AF

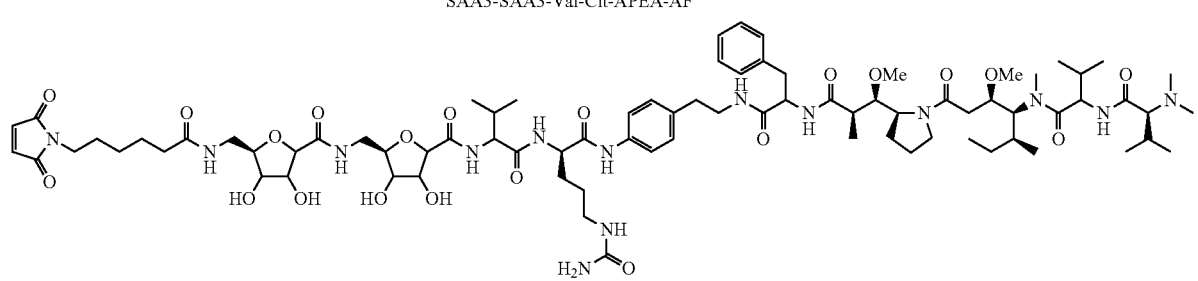

MC-SAA3-SAA3-Val-Cit-APEA-AF

Step 1

To a solution of Z-SAA3(X)—OH (14.5 mg, 0.041 mmol) and SAA3-Val-Cit-APEA-AF (54.5 mg, 0.041 mmol) in a mixture of DCM and DMF (10:1, 6 mL) was added HATU (17.3 mg, 0.045 mmol) and DIPEA (0.02 mL, 0.123 mmol) respectively. After 18 hours, the solvents were evaporated under reduced pressure and the crude product was purified by preparative HPLC (41% acetonitrile in water with 0.1% TFA; UV 210 nm; ODS-3 column 30×250 mm; flow rate 24 mL/min). After the removal of acetonitrile, the aqueous solution was stood at room temperature overnight until the ketal group was completely hydrolyzed. The aqueous solution was submitted to freeze-drying to afford Z-SAA3-SAA3-Val-Cit-APEA-AF as white solid (21.3 mg, 33% yield over two steps).

Step 2

Z-SAA3-SAA3-Val-Cit-APEA-AF (21.3 mg, 0.0135 mmol) was dissolved in ethanol (5 mL) containing hydrochloric acid (0.052 mmol). After Pd/C (10%, 2.5 mg) was charged, the reaction mixture was applied a hydrogen balloon and stirred for 5 hours. The catalyst Pd/C was filtered off through a pad of celite and then the filtrate was evaporated under reduced pressure. The product was mixed with water (5 mL) and submitted to freeze-drying to afford SAA3-SAA3-Val-Cit-APEA-AF as white solid (16.1 mg, 81%).

Step 3

To a solution of SAA3-SAA3-Val-Cit-APEA-AF (16.1 mg, 0.0109 mmol) and MC-OPFP (4.5 mg, 0.012 mmol) in DMF (5 mL) was added DIPEA (0.004 mL). The reaction mixture was stirred at room temperature for 1 hour and then evaporated under reduced pressure. The crude product was purified by preparative HPLC (33% acetonitrile in water with 0.1% TFA; UV 210 nm; ODS-3 column 30×250 mm; flow rate 24 mL/min) to afford MC-SAA3-SAA3-Val-Cit-APEA-AF (CCH-041) as white solid (9.2 mg; 52%). LC-MS: MC-SAA3-SAA3-Val-Cit-APEA-AF (CCH-041) ($C_{81}H_{126}N_{14}O_{21}$) required [MH$^+$]=1633.0, found [MH$^+$]= 1633.2.

Preparation Example 10

Synthesis of FCW-016
[MC-SAA5-Val-Cit-APEA-AF]

The linker-toxin FCW-016 was synthesized according to the procedures shown in the following scheme.

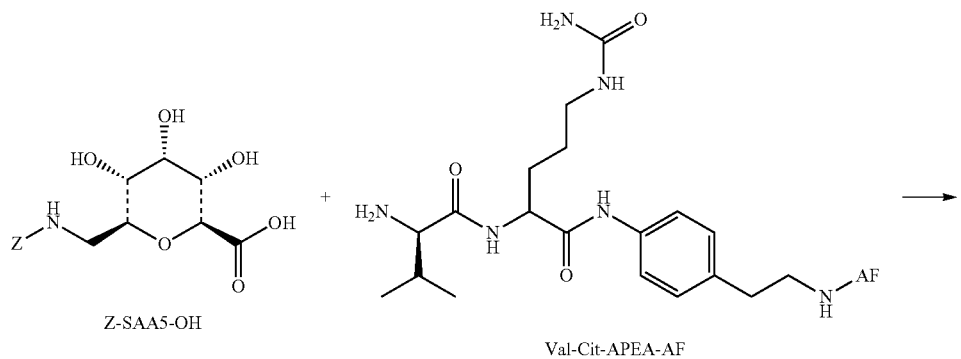

Z-SAA5-OH + Val-Cit-APEA-AF

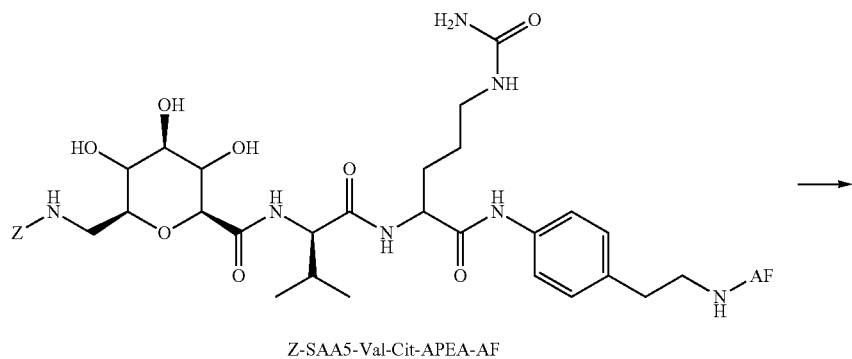

Z-SAA5-Val-Cit-APEA-AF

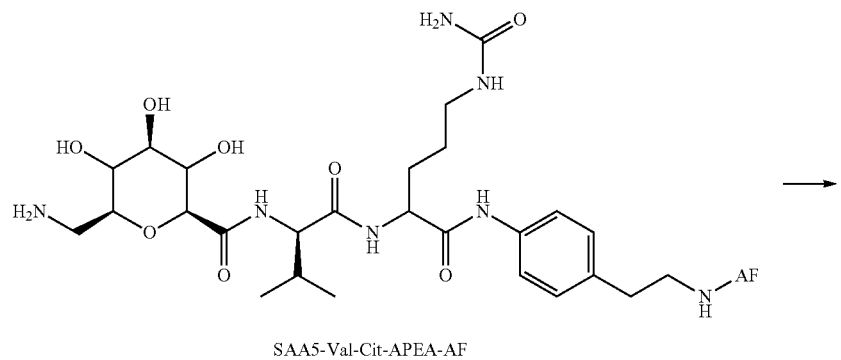

SAA5-Val-Cit-APEA-AF

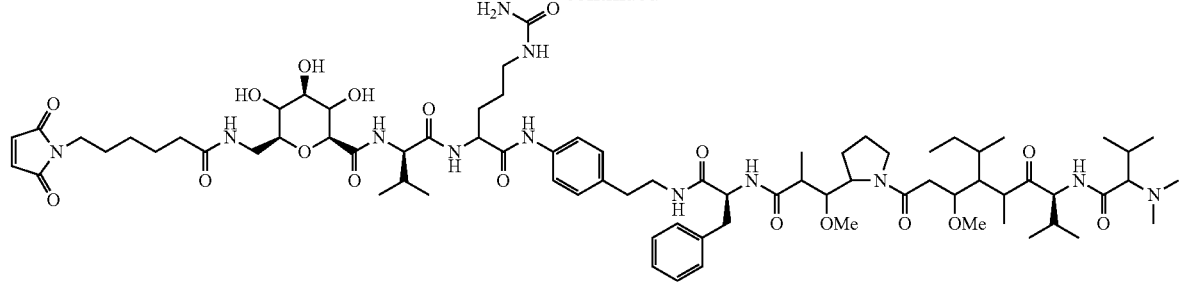

MC-SAA5-Val-Cit-APEA-AF

Step 1

HATU (40 mg, 0.1060 mmol) was added to a stirred solution of Val-Cit-APEA-AF (99 mg, 0.0884 mmol), Z-SAA5-OH (36 mg, 0.1060 mmol) and DIPEA (0.046 mL, 0.2651 mmol) in a mixture of DMF (2 mL) and dichloromethane (20 mL). After stirring at room temperature for 12 hours, the solvents were evaporated, and the residue was purified by preparative HPLC (43% acetonitrile in water with 0.1% TFA; UV 210 nm; ODS-3 column 30×250 mm; flow rate 24 mL/min) to afford Z-SAA5-Val-Cit-APEA-AF as white powder (33 mg, 26%). LC-MS: Z-SAA5-Val-Cit-APEA-AF ($C_{75}H_{115}N_{11}O_{17}$) required [M+2H]2+=721.9, found [M+2H]2+=723.6.

Step 2

Z-SAA5-Val-Cit-APEA-AF (35.0 mg, 0.024 mmol) was dissolved in ethanol (8 mL) containing HCl (0.048 mmol). After Pd/C (10%, 2.6 mg) was charged, the reaction mixture was applied a hydrogen balloon and stirred for 16 hours. The catalyst Pd/C was filtered off through a pad of celite and then the filtrate was evaporated under reduced pressure. The product was mixed with water (10 mL) and submitted to freeze-drying to afford SAA5-Val-Cit-APEA-AF as white solid (30.0 mg, 95%). LC-MS: SAA5-Val-Cit-APEA-AF ($C_{67}H_{109}N_{11}O_{15}$) required [M+2H]2+=654.9, found [M+2H]2+=656.6.

Step 3

To a solution of SAA5-Val-Cit-APEA-AF (16.5 mg, 0.0126 mmol) and MC-OPFP (5.7 mg, 0.0151 mmol) in DMF (3 mL) was added DIPEA (0.0066 mL, 0.0378 mmol). The reaction was stirred at room temperature for 3 hours and then evaporated under reduced pressure. The crude product was purified by preparative HPLC (36% acetonitrile in water with 0.1% TFA; UV 210 nm; ODS-3 column 30×250 mm; flow rate 24 mL/min) to afford MC-SAA5-Val-Cit-APEA-AF (FCW-016) as white solid (12.0 mg; 63%). LC-MS: MC-SAA5-Val-Cit-APEA-AF (FCW-016) ($C_{77}H_{120}N_{12}O_{18}$) required [M+2H]2+=751.4, found [M+2H]2+=753.1.

Preparation Example 11

Synthesis of WHY-46
[MC-SAA1-SAA1-Val-Cit-APEA-AF]

The linker-toxin WHY-46 containing two sugar units was synthesized according to the procedures shown in the following scheme.

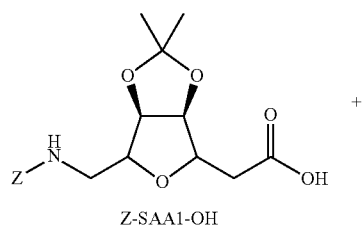

Z-SAA1-OH

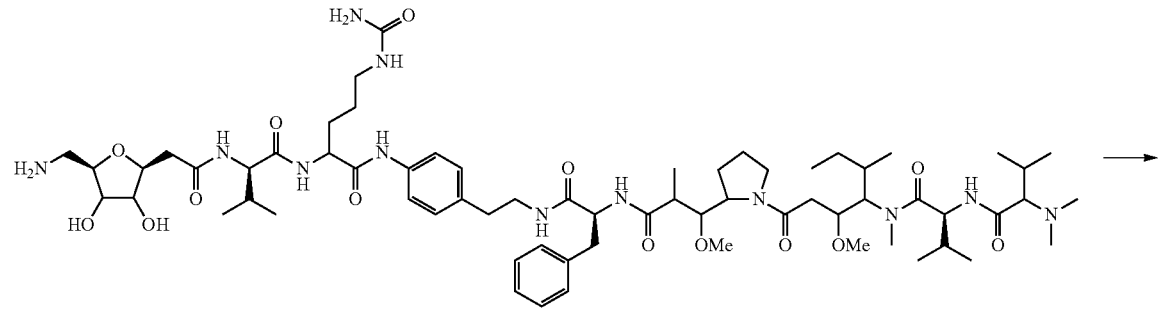

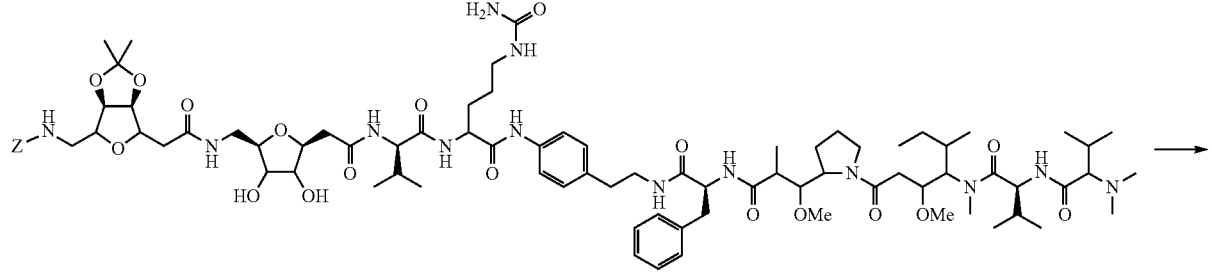

Z-SAA1(X)-SAA1-Val-Cit-APEA-AF [WHY-43]

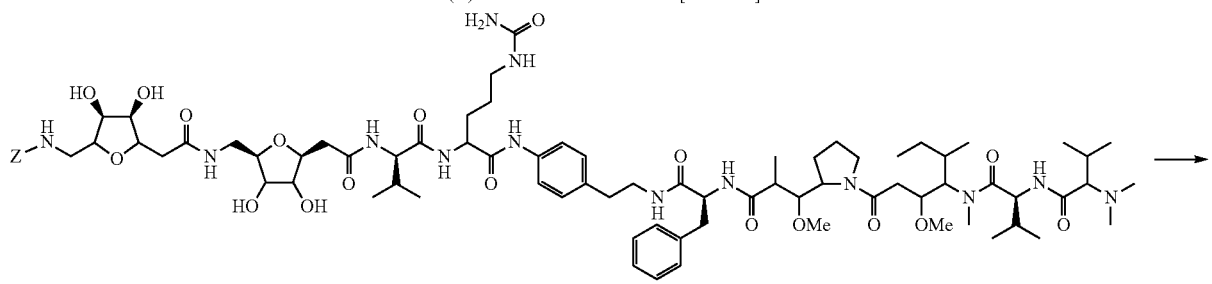

Z-SAA1-SAA1-Val-Cit-APEA-AF [WHY-43-OH]

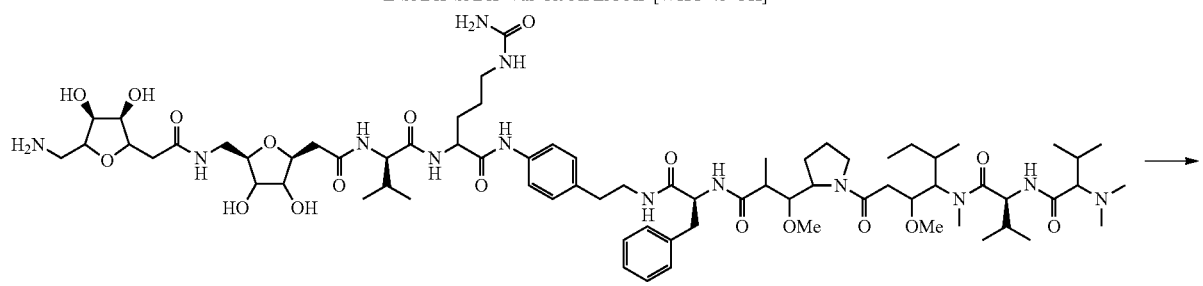

SAA1-SAA1-Val-Cit-APEA-AF [WHY-44]

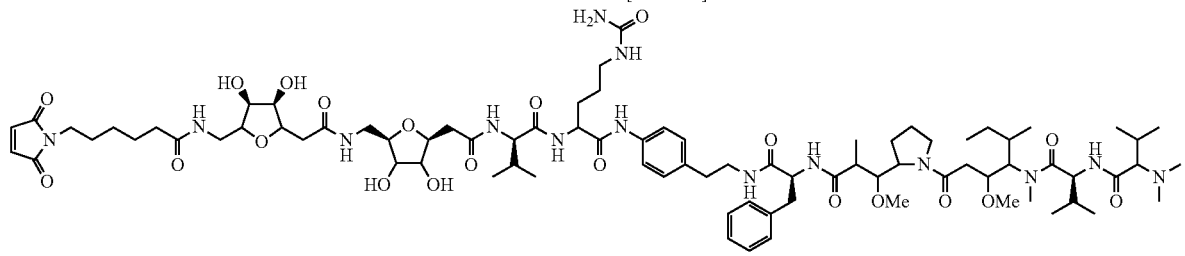

MC-SAA1-SAA1-Val-Cit-APEA-AF [WHY-46]

Step 1

Z-SAA1(X)—OH (28.0 mg, 0.076 mmol) was dissolved in dichloromethane (1 mL). After HATU (23.4 mg, 0.0.061 mmol) was added, the reaction mixture was immersed in an ice-bath followed by adding DIPEA (7.9 mg, 0.061 mmol). After 10 minutes, the ice-bath was removed and a solution of SAA1-Val-Cit-APEA-AF (70.0 mg, 0.051 mmol) in DMF (3 mL) was added to the reaction mixture at room temperature. After 1 hour, the solvents were evaporated under reduced pressure and the crude product was purified by preparative HPLC (39% acetonitrile in water with 0.1% TFA; UV 210 nm; ODS-3 column 30×250 mm; flow rate 25 mL/min). After the removal of acetonitrile, the aqueous solution was left at room temperature overnight to allow the Z-SAA1(X)-SAA1-Val-Cit-APEA-AF to completely hydrolyzed. The aqueous solution was then submitted to freeze-drying to afford Z-SAA1-SAA1-Val-Cit-APEA-AF as white solid (64 mg, 78% yield over two steps). LC-MS: Z-SAA1-SAA1-Val-Cit-APEA-AF ($C_{81}H_{125}N_{13}O_{20}$) required [MH$^+$]= 1602.0, found [MH$^+$]=1601.5.

Step 2

Z-SAA1-SAA1-Val-Cit-APEA-AF (64.0 mg, 0.042 mmol) was dissolved in ethanol (20 mL) containing hydrochloric acid (0.136 mmol). After Pd/C (10%, 6.5 mg) was charged, the reaction mixture was applied a hydrogen balloon and stirred overnight. The catalyst Pd/C was filtered off through a pad of celite and then the filtrate was evaporated under reduced pressure. The product was mixed with water (10 mL) and submitted to freeze-drying to afford SAA1-SAA1-Val-Cit-APEA-AF as white solid (60.0 mg, 97%). LC-MS: SAA1-SAA1-Val-Cit-APEA-AF ($C_{73}H_{119}N_{13}O_{18}$) required [MH$^+$]=1466.9, found [MH$^+$]=1467.5.

Step 3

SAA1-SAA1-Val-Cit-APEA-AF (30.0 mg, 0.019 mmol) and DIPEA (7.4 mg, 0.057 mmol) were dissolved in DMF (2 mL). After the reaction mixture was immersed in an ice-bath, MC-OPFP (9.0 mg, 0.023 mmol) was added. After 10 minutes, the ice-bath was removed and the mixture was stirred at room temperature for 1 hour. The solvent was evaporated under reduced pressure and the crude product was purified by preparative HPLC (33% acetonitrile in water with 0.1% TFA; UV 210 nm; ODS-3 column 30×250 mm; flow rate 25 mL/min) to afford MC-SAA1-SAA1-Val-Cit-APEA-AF as white solid (18.5 mg, 53%). LC-MS: MC-SAA1-SAA1-Val-Cit-APEA-AF (WHY-46) ($C_{83}H_{130}N_{14}O_{21}$) required [MH$^+$]=1660.0, found [MH$^+$]=1660.7.

Comparative Preparation Example 12

Synthesis of MHT-87 [MC-Val-Cit-APEA-AF]

The linker-toxin MHT-87 was synthesized according to the procedures shown in the following scheme.

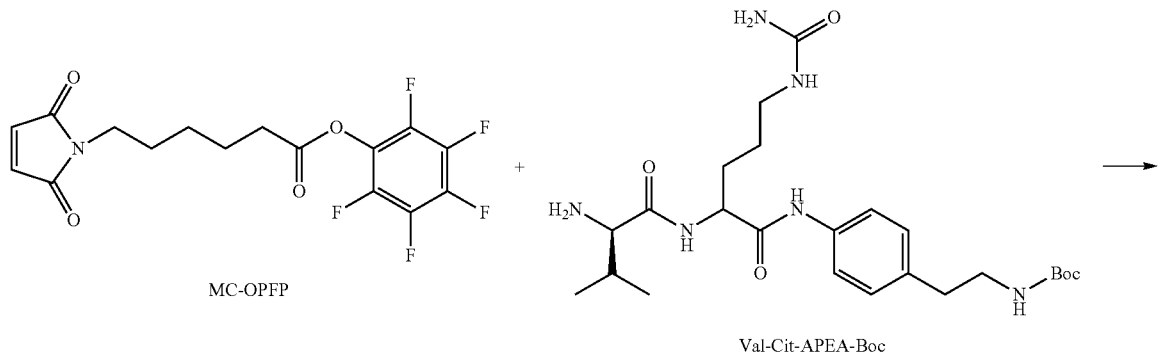

MC-OPFP + Val-Cit-APEA-Boc

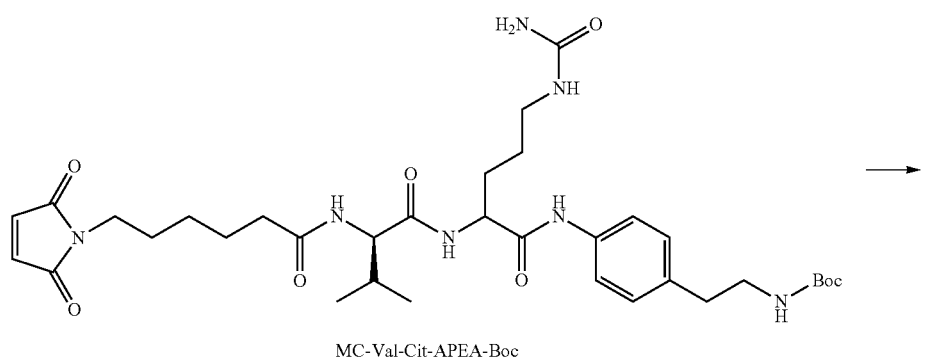

MC-Val-Cit-APEA-Boc

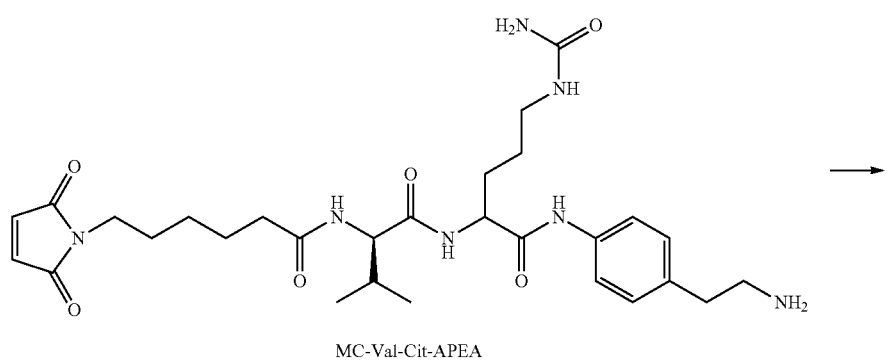

MC-Val-Cit-APEA

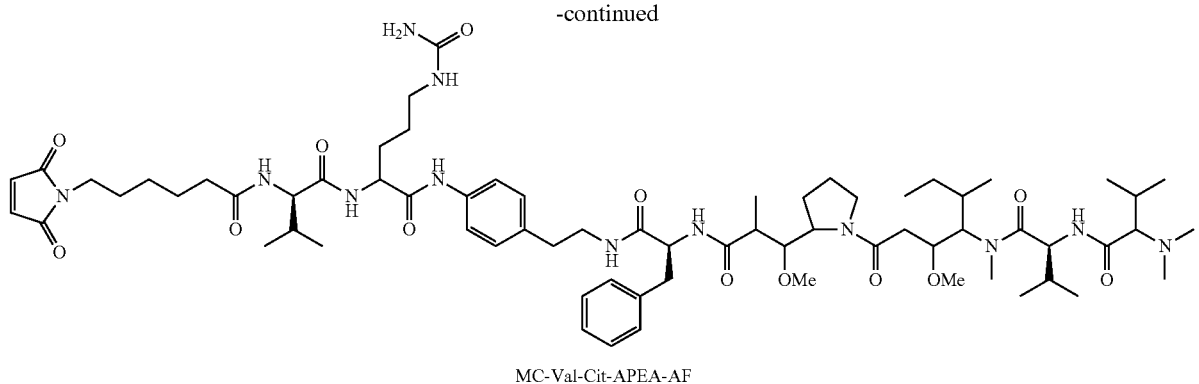

MC-Val-Cit-APEA-AF

Step 1

Val-Cit-APEA-Boc (65 mg) and MC-OPFP (50 mg) were dissolved in DMF (5 mL) and then DIPEA (0.023 mL) was added. After 5 hours, DMF and DIPEA were removed under reduced pressure. The crude product was then purified by preparative HPLC (50% acetonitrile in water with 0.1% TFA; UV 210 nm; ODS-3 column 50×500 mm; flow rate 80 mL/min; RT 13.60 min) to afford MC-Val-Cit-APEA-Boc as white solid (40 mg). LC-MS: 88 ($C_{34}H_{51}N_7O_8$) required [$MH^+$]=686.4, found [$MH^+$]=687.3.

Step 2

MC-Val-Cit-APEA-Boc (40 mg) in DCM (5 mL) was treated with TFA (300 L) at room temperature. After 17 hours, DCM and TFA were removed under reduced pressure to afford MC-Val-Cit-APEA as light yellow solid (46 mg). LC-MS: MC-Val-Cit-APEA ($C_{29}H_{43}N_7O_6$) required [$MH^+$]= 586.3, found [$MH^+$]=586.7.

Step 3

MC-Val-Cit-APEA (37 mg) and auristatin F (47 mg) were dissolved in a mixture of DCM and DMF (10:1, 3.7 mL). Then, HBTU (37 mg) and DIPEA (0.037 mL) were added. After 17 hours, DCM and DMF were removed under reduced pressure and the crude product was purified by preparative HPLC (40% acetonitrile in water with 0.1% TFA; UV 210 nm; ODS-3 column 30*250 mm; flow rate 25 mL/min; RT 14 min) to afford MC-Val-Cit-APEA-AF (MHT-87) as white solid (9 mg). LC-MS: MC-Val-Cit-APEA-AF (MHT-87) ($C_{70}H_{109}N_{11}O_{13}$) required [$MH^+$]= 1312.8, found [$MH^+$]=1315.2.

Antibody-Drug Conjugate (ADC)

Antibody-Linker-Toxin

Example 1

Conjugation of EG12014-MHT-71 in Co-Solvent System Containing 6.7% of Organic Solvent 12 mL of EG12014 (produced by EirGenix Inc.)(initial concentration: 12.5 mg/mL) was treated with 269 µL of 10 mM TCEP (2.5 molar equivalent) in borate buffer for 2 hours at 37° C. Next, 3.55 mL of 3 mM linker-toxin MHT-71 (9.9 molar equivalent) prepared in 30% (v/v) DMSO was added to the above-mentioned antibody solution for 30 minutes at 4° C. (final concentration of organic solvent in the mixture solution was about 6.7%). 1.5 mL of 0.1 M cysteine was added to stop the reaction. A desalting column (ThermoFisher Scientific, MWCO: 40K) was used to purify EG12014-MHT-71. During elution, the buffer was changed to PBS buffer (2.67 mM KCl, 1.47 mM $KH_2PO_4$, 137.93 mM NaCl, 8.06 mM $Na_2HPO_4$-$7H_2O$). Hydrophobic interaction chromatography (HIC) (described below) and size-exclusion chromatography (SEC) (described below) were used to determine the average drug-to-antibody ratio (DAR) and high molecular weight species (HMWS).

HIC (Hydrophobic Interaction Chromatography) Analysis

An Agilent HPLC with the Butyl NPR (4.6×35 mm) TOSOH column was used to analyze the drug-to-antibody ratio (DAR) profile. The mobile phase A consisted of 25 mM sodium phosphate, 1.5 M ammonium sulfate, pH 6.95, and mobile phase B consisted of 25 mM sodium phosphate, 25% isopropanol, pH 6.95. 15 µL of samples were injected into the column at a flow rate of 0.8 mL/min and separated under gradient mode: 0-100% mobile phase B in 12 minutes. Absorbance was detected at 280 nm.

SEC (Size-Exclusion Chromatography) Analysis

A Waters PDA 996 HPLC with the Yarra 3 µm SEC-3000 (300×7.8 mm) column was used to separate antibody monomer and aggregation products by size. The mobile phase consisted of 0.020 M potassium phosphate, 0.025 M potassium chloride, and isopropanol 5% (v/v), pH 6.95. 30 µL of samples were injected into the column at a flow rate of 0.5 mL/min and separated under isocratic conditions. Absorbance was detected at 280 nm. All species eluting prior to the main peak were integrated together and are reported as high molecular weight species (HMWS).

Figure 2:
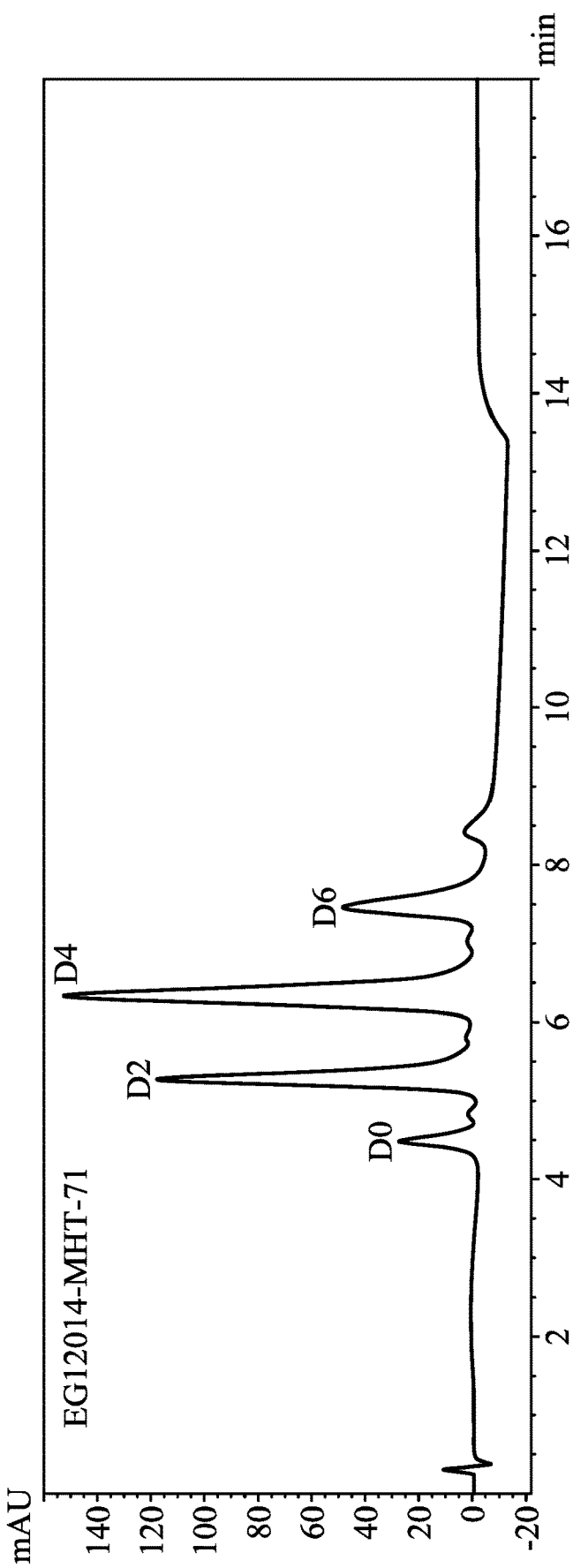
FIG. 2 shows a HIC profile of EG12014-MHT-71 in accordance with one embodiment of the present disclosure.

FIG. 2 shows that the DAR of the ADC mainly distributes at 2 and 4. The average DAR of the EG12014-MHT-71 is about 3.7. The conjugation efficiency is about 95%.

Example 2

Conjugation of EG12014-MHT-71 in Aqueous Phase 0.14 mL of EG12014 (produced by EirGenix Inc.) (initial concentration: 7.5 mg/mL) was treated with 3.4 µL of 5 mM TCEP (2.4 molar equivalent) in borate buffer for 2 hours at 37° C. Next, 13.9 µL of 5 mM linker-toxin MHT-71 (9.9 molar equivalent) prepared in $ddH_2O$ was added to the above-mentioned antibody solution for 30 minutes at 4° C. (pure aqueous phase). 15 µL of 0.2 M cysteine was added to stop the reaction. A desalting column (ThermoFisher Scientific, MWCO: 40K) was used to purify EG12014-MHT-71. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 3A:
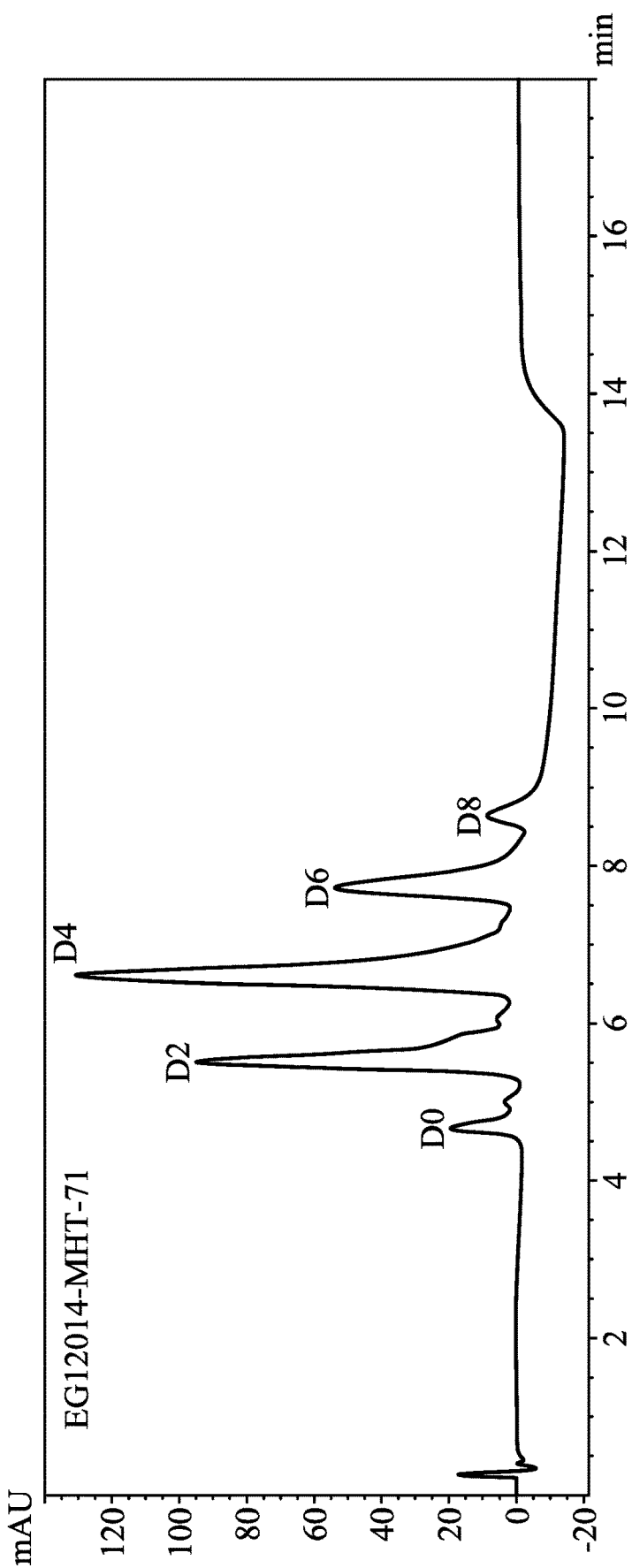
FIG. 3A shows a HIC profile of EG12014-MHT-71 in accordance with one embodiment of the present disclosure.

FIG. 3A shows that the DAR of the ADC mainly distributes at 2 and 4. The average DAR of the EG12014-MHT-71 is about 3.9. The conjugation efficiency is about 96%.

Example 3

Conjugation of EG12014-MHT-71 in Aqueous Phase 0.14 mL of EG12014 (produced by EirGenix Inc.) (initial concentration: 7.5 mg/mL) was treated with 4.8 µL of 5 mM TCEP (3.4 molar equivalent) in borate buffer for 2 hours at 37° C. Next, 13.9 µL of 5 mM linker-toxin MHT-71 (9.9 molar equivalent) prepared in ddH$_2$O was added to the above-mentioned antibody solution for 30 minutes at 4° C. (pure aqueous phase). 15 µL of 0.2 M cysteine was added to stop the reaction. A desalting column (ThermoFisher Scientific, MWCO: 40K) was used to purify EG12014-MHT-71. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 3B:
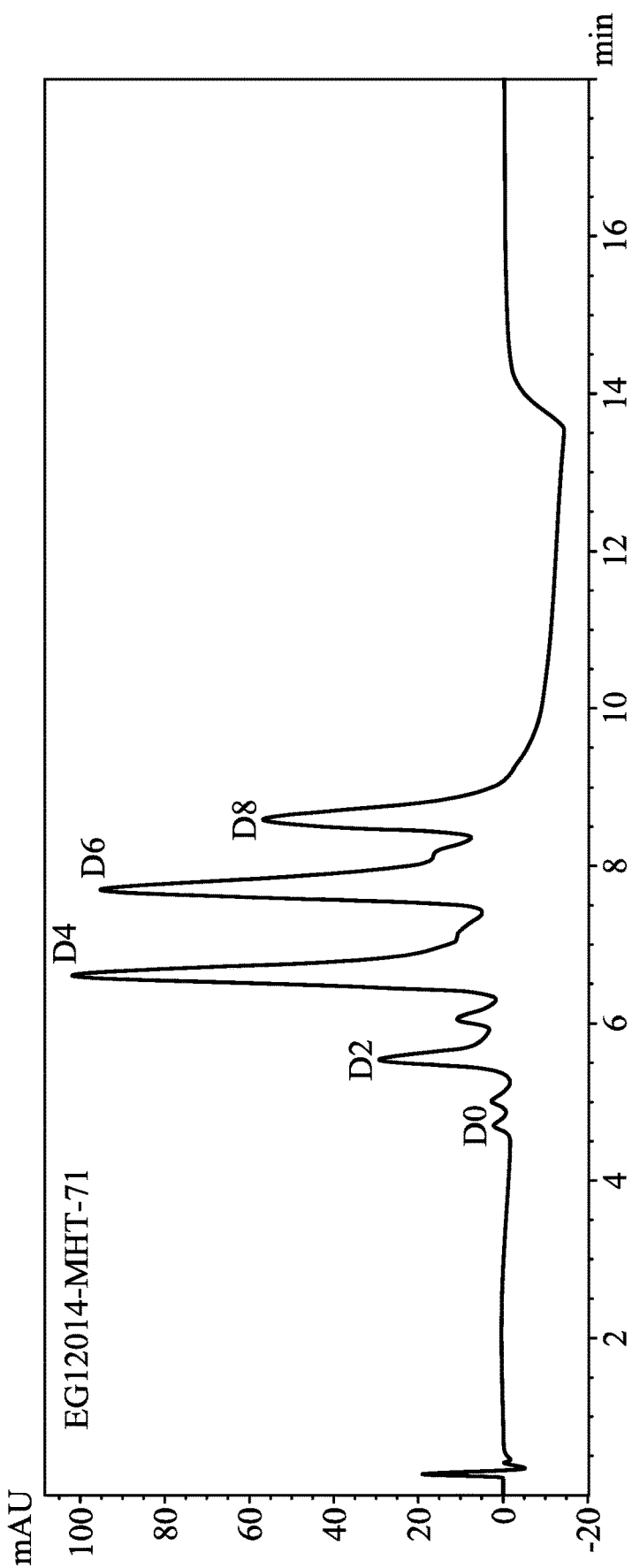
FIG. 3B shows a HIC profile of EG12014-MHT-71 in accordance with one embodiment of the present disclosure.

FIG. 3B shows that the DAR of the ADC mainly distributes at 4 and 6. The average DAR of the EG12014-MHT-71 is about 5.4. The conjugation efficiency is about 99%.

Example 4

Conjugation of IgG1-MHT-47 in Co-Solvent System Containing 16.7% of Organic Solvent 0.1 mL of human IgG1 (Sigma)(initial concentration: 2.6 mg/mL) was treated with 1.6 µL of 2.5 mM TCEP (2.4 molar equivalent) in borate buffer for 2 hours at 37° C. Next, 29.0 µL of 363 µM linker-toxin MHT-47 (9.9 molar equivalent) prepared in 75% (v/v) DMSO was added to the above-mentioned antibody solution for 30 minutes at 4° C. (final concentration of organic solvent in the mixture solution was about 16.7%). 5 µL of 0.1 M cysteine was added to stop the reaction. A desalting column (ThermoFisher Scientific, MWCO: 40K) was used to purify IgG1-MHT-47. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 4:
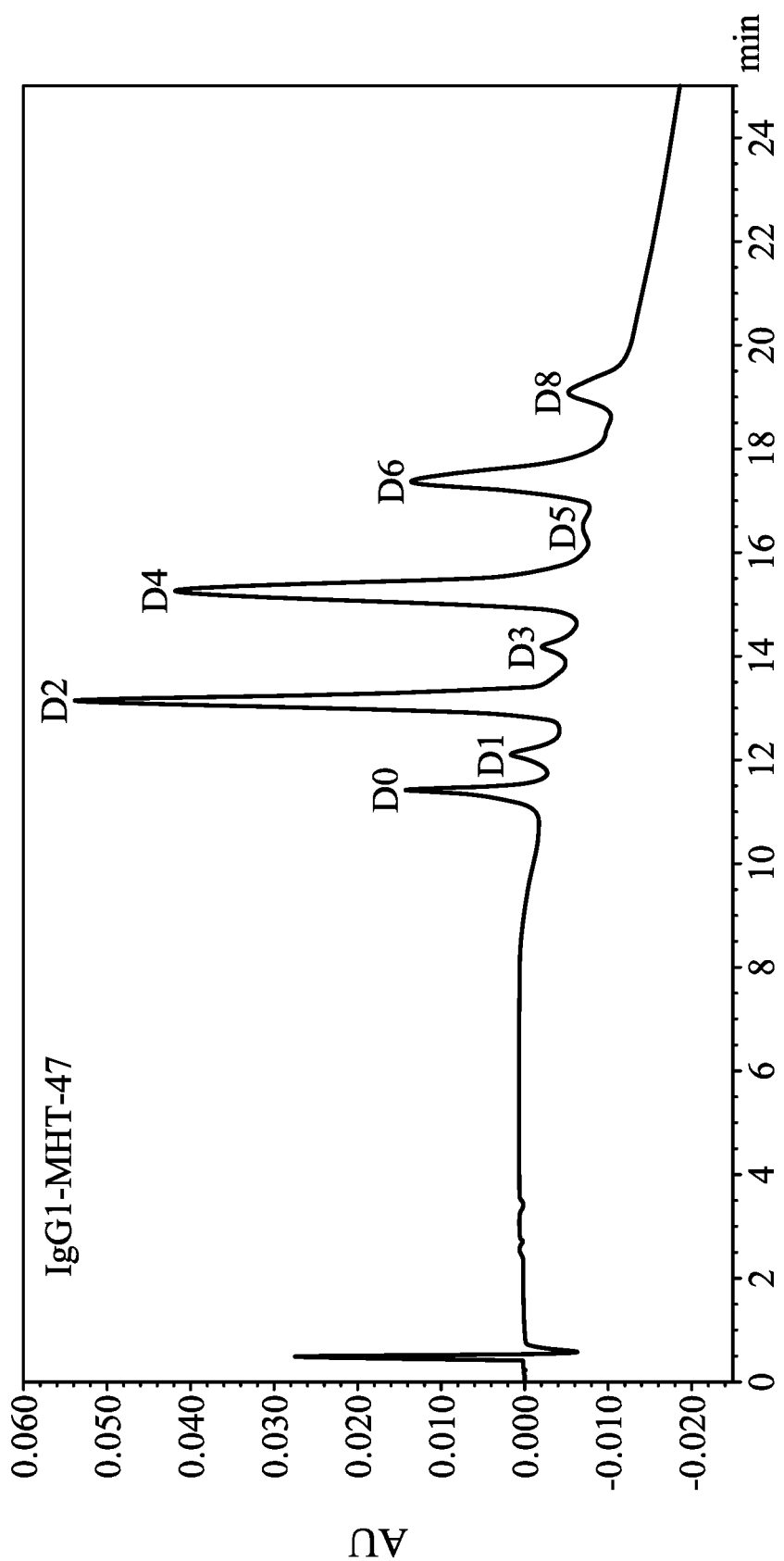
FIG. 4 shows a HIC profile of IgG1-MHT-47 in accordance with one embodiment of the present disclosure.

FIG. 4 shows that the DAR of the ADC mainly distributes at 2 and 4. The average DAR of the IgG1-MHT-47 is about 3.7. The conjugation efficiency is about 93%.

Example 5

Conjugation of IgG1-MHT-47 in Co-Solvent System Containing 2% of Organic Solvent 60 µL of human IgG1 (sigma) (initial concentration: 5.7 mg/mL) was treated with 1.2 µL of 10 mM TCEP (2.2 molar equivalent) in borate buffer for 2 hours at 37° C. Next, 4.6 µL of 3 mM linker-toxin MHT-47 (6 molar equivalent) prepared in 30% (v/v) DMSO was added to the above-mentioned antibody solution for 30 minutes at 4° C. (final concentration of organic solvent in the mixture solution was about 2%). 0.5 µL of 0.2 M cysteine was added to stop the reaction. A desalting column (ThermoFisher Scientific, MWCO: 40K) was used to purify IgG1-MHT-47. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 5:
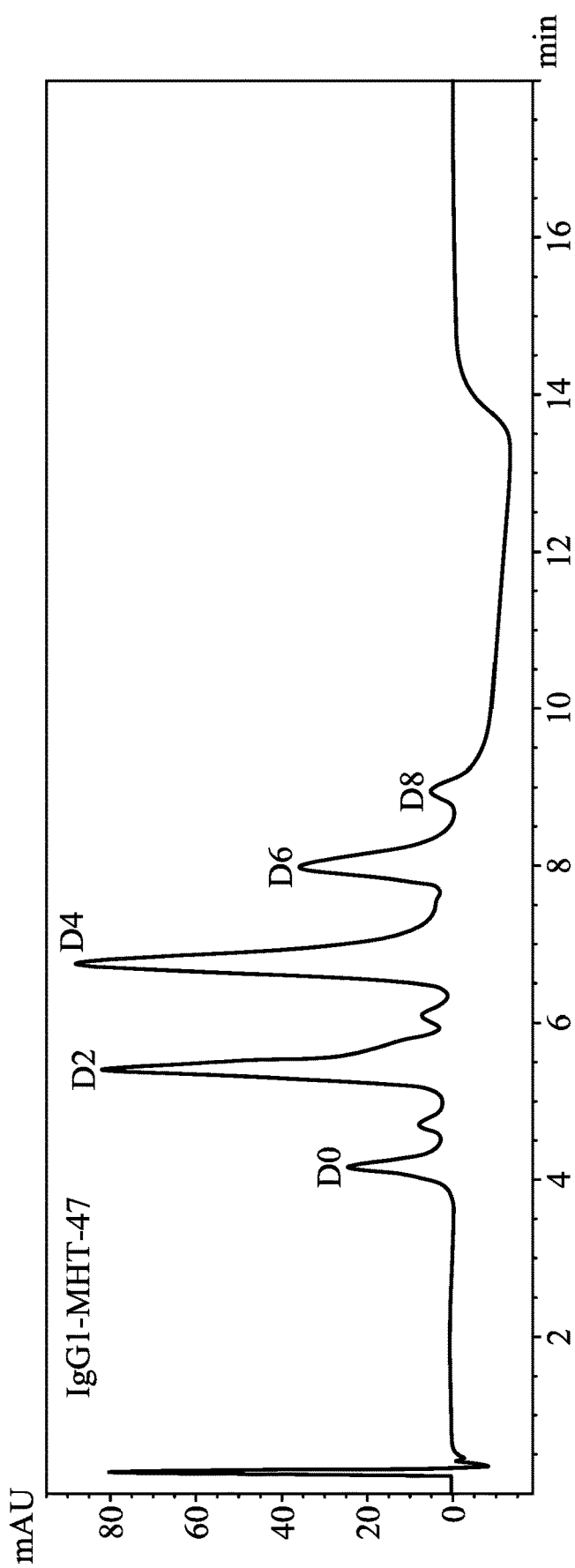
FIG. 5 shows a HIC profile of IgG1-MHT-47 in accordance with one embodiment of the present disclosure.

FIG. 5 shows that the DAR of the ADC mainly distributes at 2 and 4. The average DAR of the IgG1-MHT-47 is about 3.7. The conjugation efficiency is about 93%.

Example 6

Conjugation of Herceptin®-MHT-47 in Co-Solvent System Containing 5.5% of Organic Solvent 0.3 mL of Herceptin® (trastuzumab)(Roche) (initial concentration: 10.3 mg/mL) was treated with 5.2 µL of 10 mM TCEP (2.5 molar equivalent) in borate buffer for 2 hours at 37° C. Next, 69.1 µL of 3 mM linker-toxin MHT-47 (9.9 molar equivalent) prepared in 30% (v/v) DMSO was added to the above-mentioned antibody solution for 30 minutes at 4° C. (final concentration of organic solvent in the mixture solution was about 5.5%). 20 µL of 0.1 M cysteine was added to stop the reaction. A desalting column (ThermoFisher Scientific, MWCO: 40K) was used to purify Herceptin®-MHT-47. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 6:
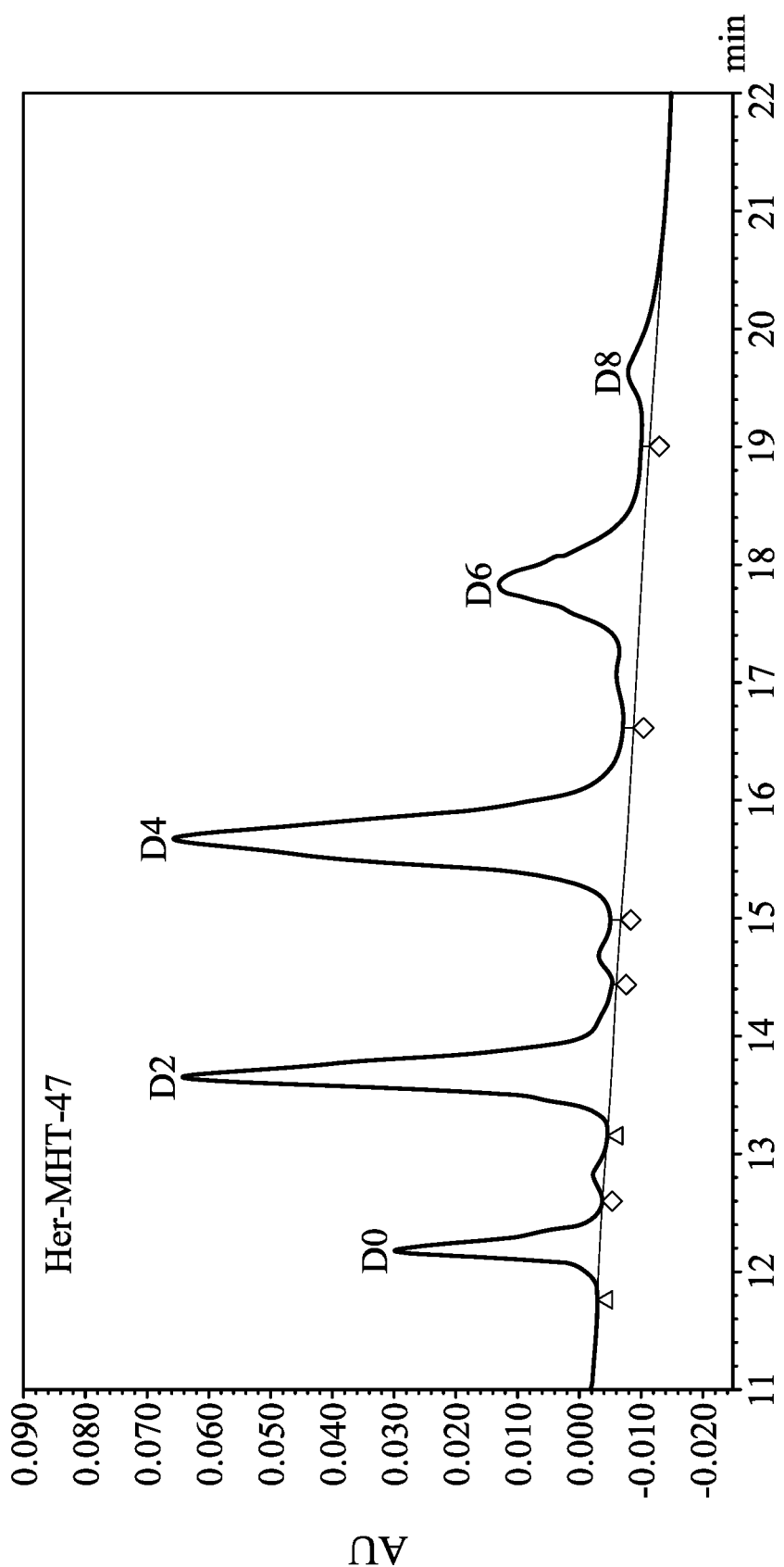
FIG. 6 shows a HIC profile of Herceptin®-MHT-47 in accordance with one embodiment of the present disclosure.

FIG. 6 shows that the DAR of the ADC mainly distributes at 2 and 4. The average DAR of the Herceptin®-MHT-47 is about 3.7. The conjugation efficiency is about 92%.

Example 7

Conjugation of Herceptin®-CCH-038 in Aqueous Phase 0.22 mL of Herceptin® (Trastuzumab)(Roche) (initial concentration: 11.3 mg/mL) was treated with 4.2 µL of 10 mM TCEP (2.5 molar equivalent) in borate buffer for 2 hours at 37° C. Next, 55.4 µL of 3 mM linker-toxin CCH-038 (9.9 molar equivalent) prepared in ddH$_2$O was added to the above-mentioned antibody solution for 30 minutes at 4° C. (pure aqueous phase). 2 µL of 0.2 M cysteine was added to stop the reaction. A desalting column (ThermoFisher Scientific, MWCO: 40K) was used to purify Herceptin®-CCH-038. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 7:
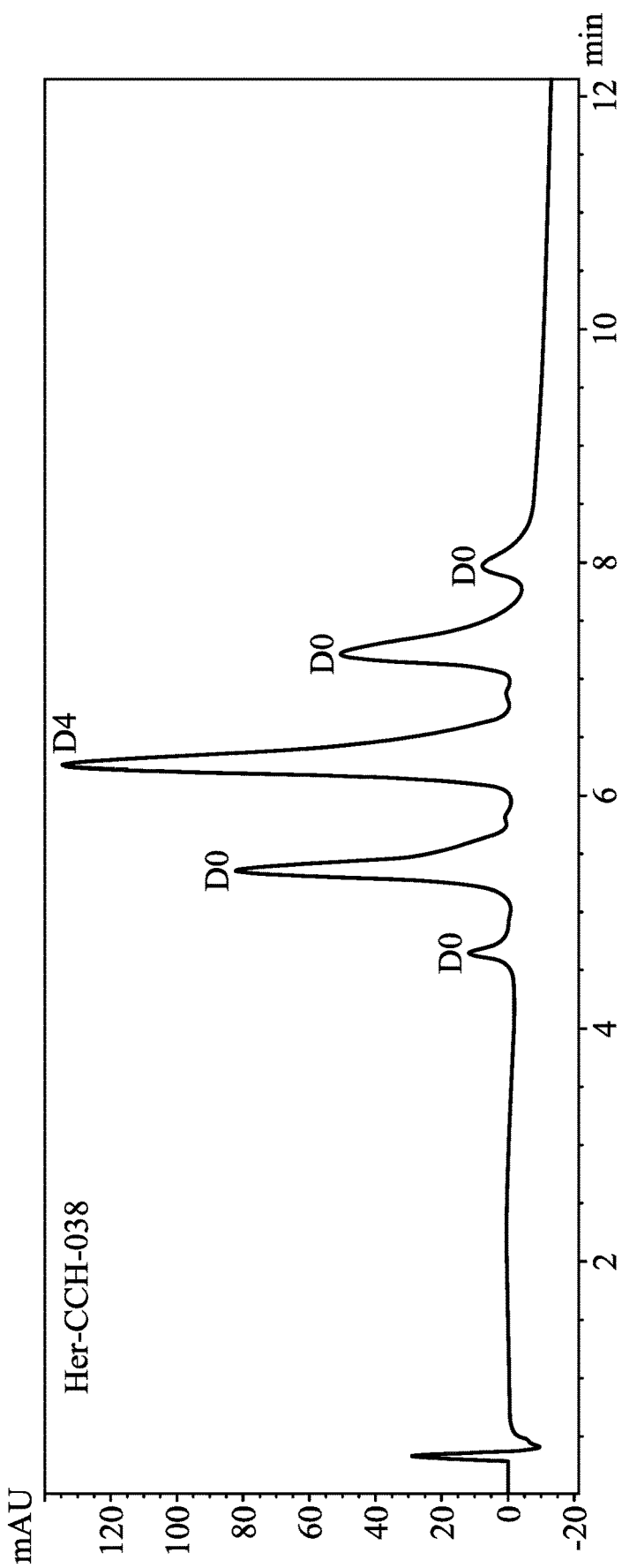
FIG. 7 shows a HIC profile of Herceptin®-CCH-038 in accordance with one embodiment of the present disclosure.

FIG. 7 shows that the DAR of the ADC mainly distributes at 2 and 4. The average DAR of the Herceptin®-CCH-038 is about 4.0. The conjugation efficiency is about 97%.

Example 8

Conjugation of Erbitux®-CCH-028 in Co-Solvent System Containing 1.6% of Organic Solvent 0.6 mL of Erbitux® (Cetuximab)(Merck) (initial concentration: 4.2 mg/mL) was treated with 3.8 µL of 10 mM TCEP (2.2 molar equivalent) in borate buffer for 2 hours at 37° C. Next, 34.2 µL of 3 mM linker-toxin CCH-028 (6 molar equivalent) prepared in 30% (v/v) DMSO was added to the above-mentioned antibody solution for 30 minutes at 4° C. (final concentration of organic solvent in the mixture solution was about 1.6%). 100 µL of 0.1 M cysteine was added to stop the reaction. A desalting column (ThermoFisher Scientific, MWCO: 40K) was used to purify Erbitux®-CCH-028. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 8:
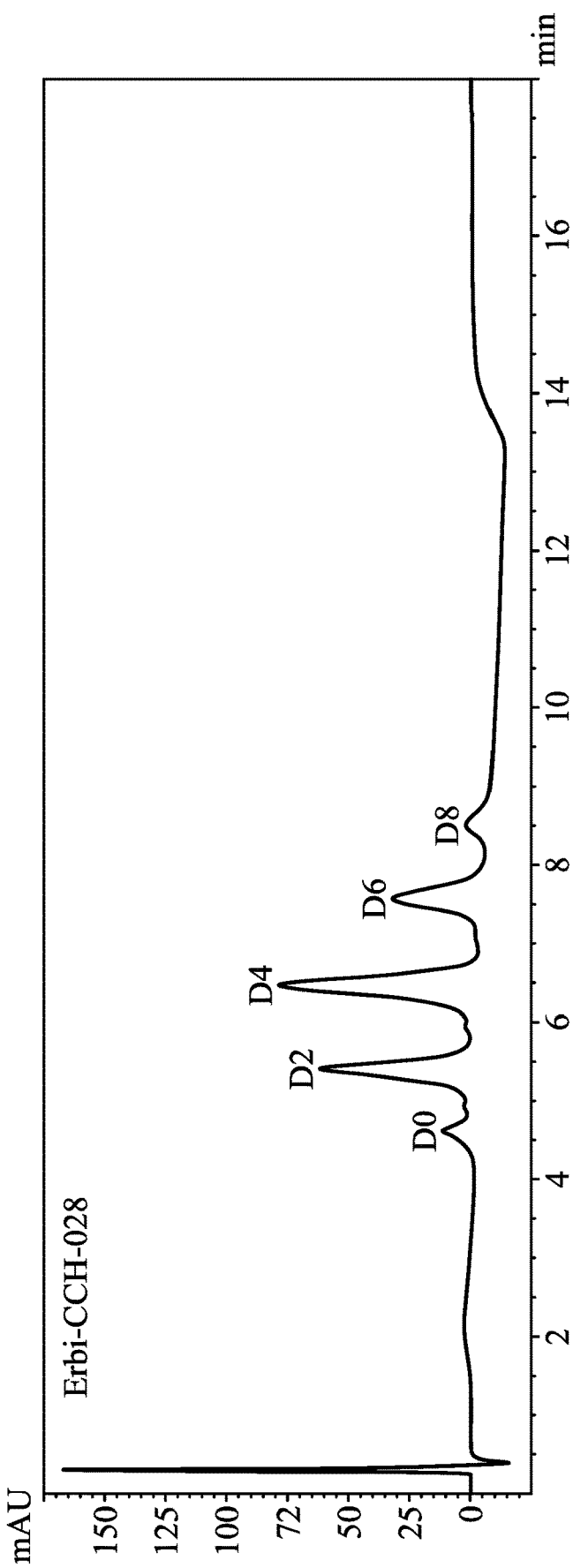
FIG. 8 shows a HIC profile of Erbitux-CCH-028 in accordance with one embodiment of the present disclosure.

FIG. 8 shows that the DAR of the ADC mainly distributes at 2 and 4. The average DAR of the Erbitux®-CCH-028 is about 3.8. The conjugation efficiency is about 95%.

Example 9

Conjugation of Erbitux®-CCH-035 in Co-Solvent System Containing 1.7% of Organic Solvent 0.6 mL of Erbitux® (Cetuximab)(Merck) (initial concentration: 4.3 mg/mL) was treated with 3.9 µL of 10 mM TCEP (2.2 molar equivalent) in borate buffer for 2 hours at 37° C. Next, 35.2 µL mL of 3 mM linker-toxin CCH-035 (6 molar equivalent) prepared in 30% (v/v) DMSO was added to the above-mentioned antibody solution for 30 minutes at 4° C. (final concentration of organic solvent in the mixture solution was about 1.7%). 50 µL of 0.2 M cysteine was added to stop the reaction. A desalting column (ThermoFisher Scientific, MWCO: 40K) was used to purify Erbitux®-CCH-035. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 9:
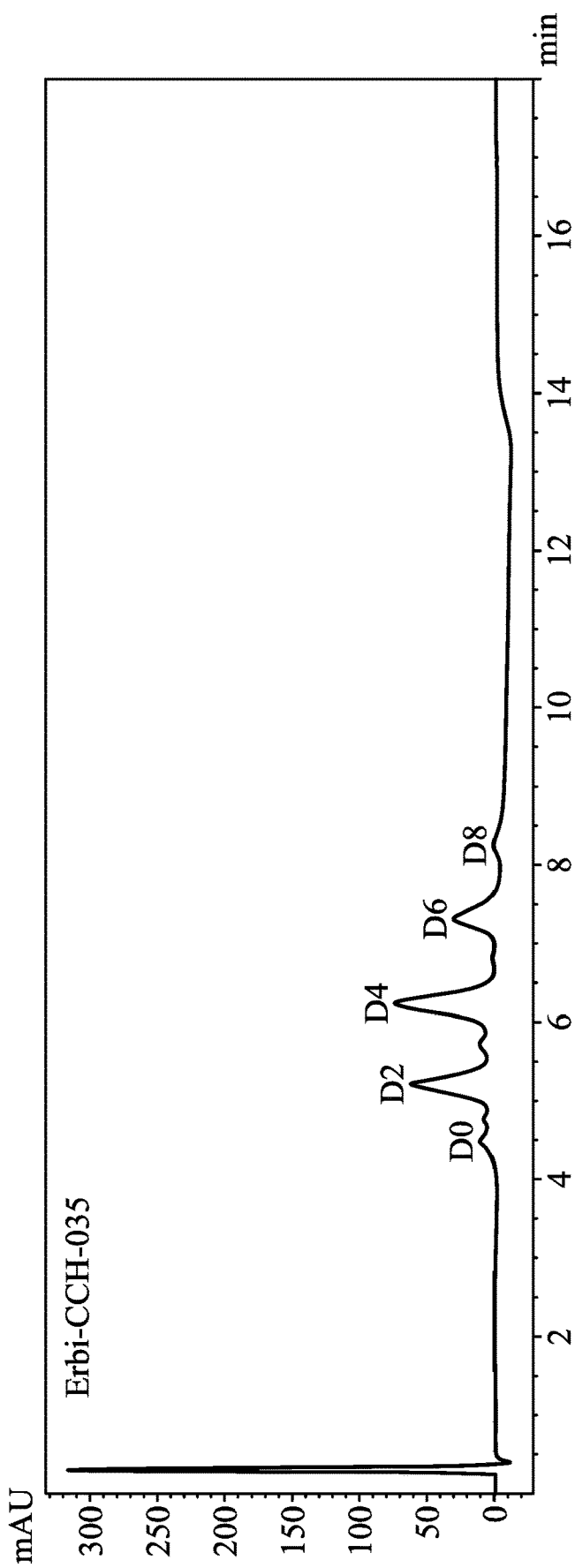
FIG. 9 shows a HIC profile of Erbitux-CCH-035 in accordance with one embodiment of the present disclosure.

FIG. 9 shows that the DAR of the ADC mainly distributes at 2 and 4. The average DAR of the Erbitux®-CCH-035 is about 3.6. The conjugation efficiency is about 94%.

Example 10

Conjugation of Erbitux®-CCH-041 in Co-Solvent System Containing 1.5% of Organic Solvent 0.85 mL of Erbitux® (Cetuximab)(Merck) (initial concentration: 3.8 mg/mL) was treated with 4.9 µL of 10 mM TCEP (2.2 molar equivalent) in borate buffer for 2 hours at 37° C. Next, 44.5 µL of 3 mM linker-toxin CCH-041 (6 molar equivalent) prepared in 30% (v/v) DMSO was added to the above-mentioned antibody solution for 30 minutes at 4° C. (final concentration of organic solvent in the mixture solution was about 1.5%). 80 µL of 0.2 M cysteine was added to stop the reaction. A desalting column (ThermoFisher Scientific, MWCO: 40K) was used to purify Erbitux®-CCH-041. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 10:
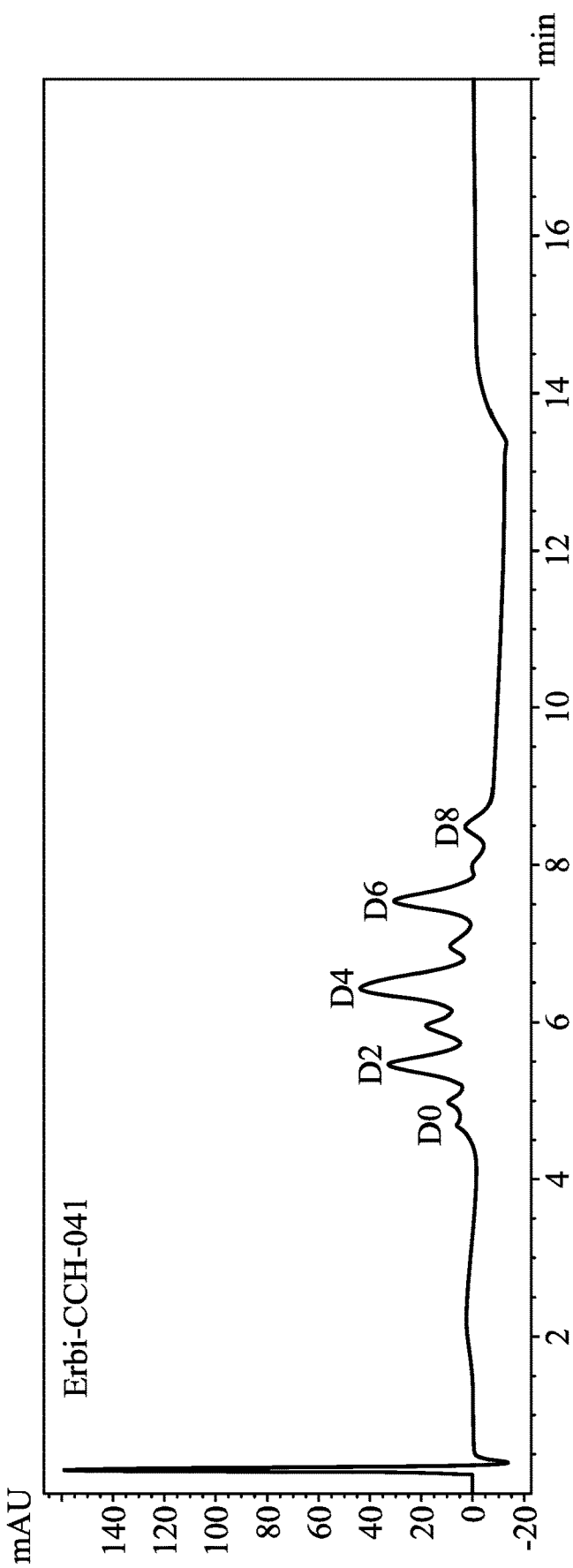
FIG. 10 shows a HIC profile of Erbitux-CCH-041 in accordance with one embodiment of the present disclosure.

FIG. 10 shows that the DAR of the ADC mainly distributes at 2 and 4. The average DAR of the Erbitux®-CCH-041 is about 3.9. The conjugation efficiency is about 96%.

Example 11

Conjugation of Erbitux®-FCW-016 in Co-Solvent System Containing 1.4% of Organic Solvent 0.4 mL of Erbitux® (Cetuximab)(Merck) (initial concentration: 3.5 mg/mL) was treated with 4.0 µL of 5 mM TCEP (2.1 molar equivalent) in borate buffer for 2 hours at 37° C. Next, 5.70 µL of 10 mM linker-toxin FCW-016 (6 molar equivalent) prepared in 100% (v/v) DMSO was added to the above-mentioned antibody solution for 30 minutes at 4° C. (final concentration of organic solvent in the mixture solution was about 1.4%). 15 µL of 0.1 M cysteine was added to stop the reaction. A desalting column (ThermoFisher Scientific, MWCO: 40K) was used to purify Erbitux®-FCW-016. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 11:
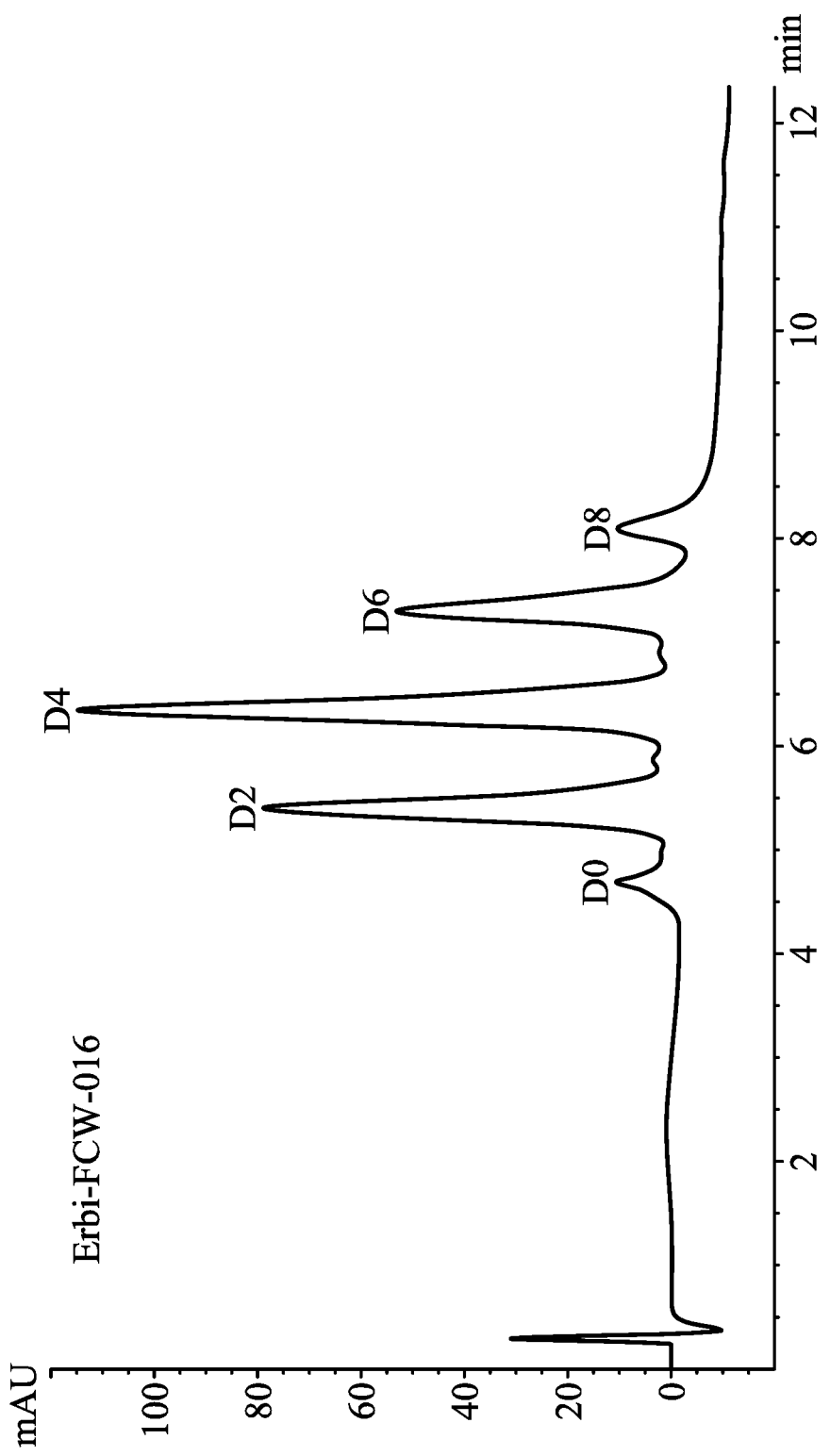
FIG. 11 shows a HIC profile of Erbitux-FCW-016 in accordance with one embodiment of the present disclosure.

FIG. 11 shows that the DAR of the ADC mainly distributes at 2 and 4. The average DAR of the Erbitux®-FCW-016 is about 4.0. The conjugation efficiency is about 96%.

Example 12

Conjugation of Erbitux®-CCH-038 in Aqueous Phase 2.0 mL of Erbitux® (Cetuximab)(Merck) (initial concentration: 4.5 mg/mL) was treated with 13.6 µL of 10 mM TCEP (2.1 molar equivalent) in borate buffer for 2 hours at 37° C. Next, 123.2 µL of 3 mM linker-toxin CCH-038 (6 molar equivalent) prepared in ddH$_2$O was added to the above-mentioned antibody solution for 30 minutes at 4° C. (pure aqueous phase). 20 µL of 0.2 M cysteine was added to stop the reaction. A desalting column (ThermoFisher Scientific, MWCO: 40K) was used to purify Erbitux®-CCH-038. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 12:
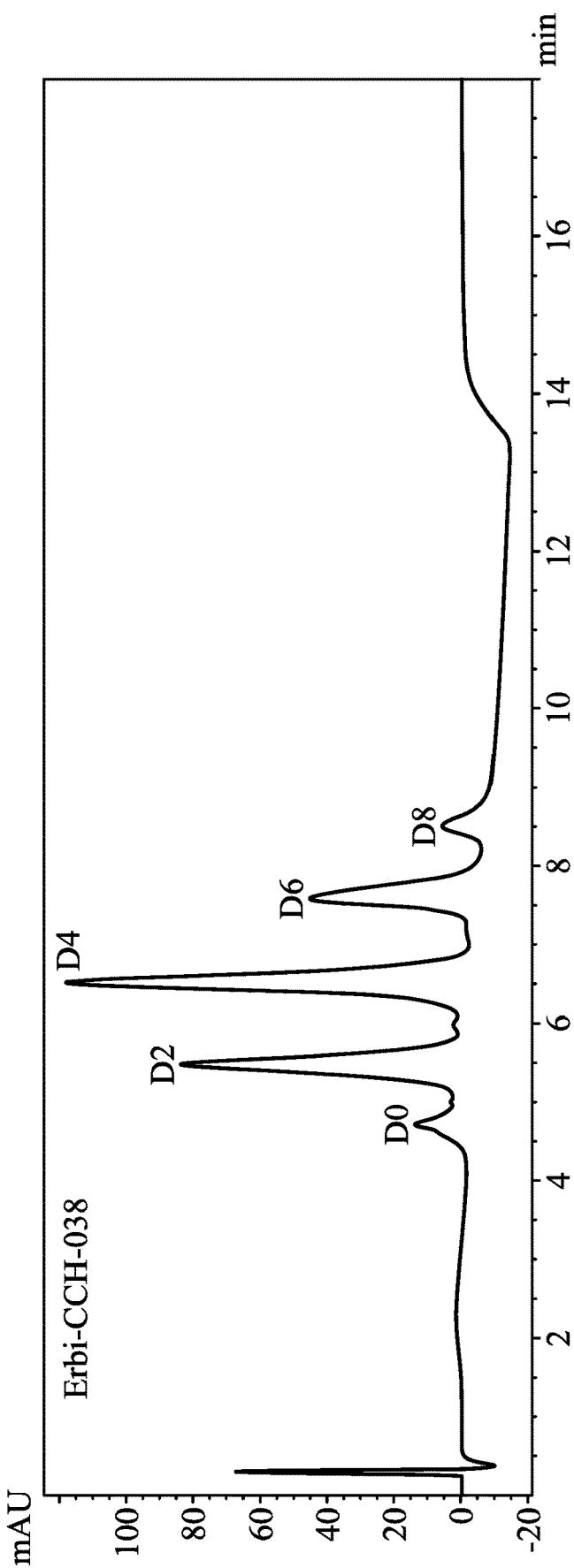
FIG. 12 shows a HIC profile of Erbitux-CCH-038 in accordance with one embodiment of the present disclosure.

FIG. 12 shows that the DAR of the ADC mainly distributes at 2 and 4. The average DAR of the Erbitux®-CCH-038 is about 3.8. The conjugation efficiency is about 95%.

Example 13

Conjugation of Erbitux®-WHY-46 in Aqueous Phase 2.3 mL of Erbitux® (Cetuximab)(Merck) (initial concentration: 4.3 mg/mL) was treated with 14.5 µL of 10 mM TCEP (2.2 molar equivalent) in borate buffer for 2 hours at 37° C. Next, 131.5 µL of 3 mM linker-toxin WHY-46 (6 molar equivalent) prepared in ddH$_2$O was added to the above-mentioned antibody solution for 30 minutes at 4° C. (pure aqueous phase). 250 µL of 0.2 M cysteine was added to stop the reaction. A desalting column (ThermoFisher Scientific, MWCO: 40K) was used to purify Erbitux®-WHY-46. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O). HIC and SEC were used to determine the average DAR and HMWS.

Figure 13A:
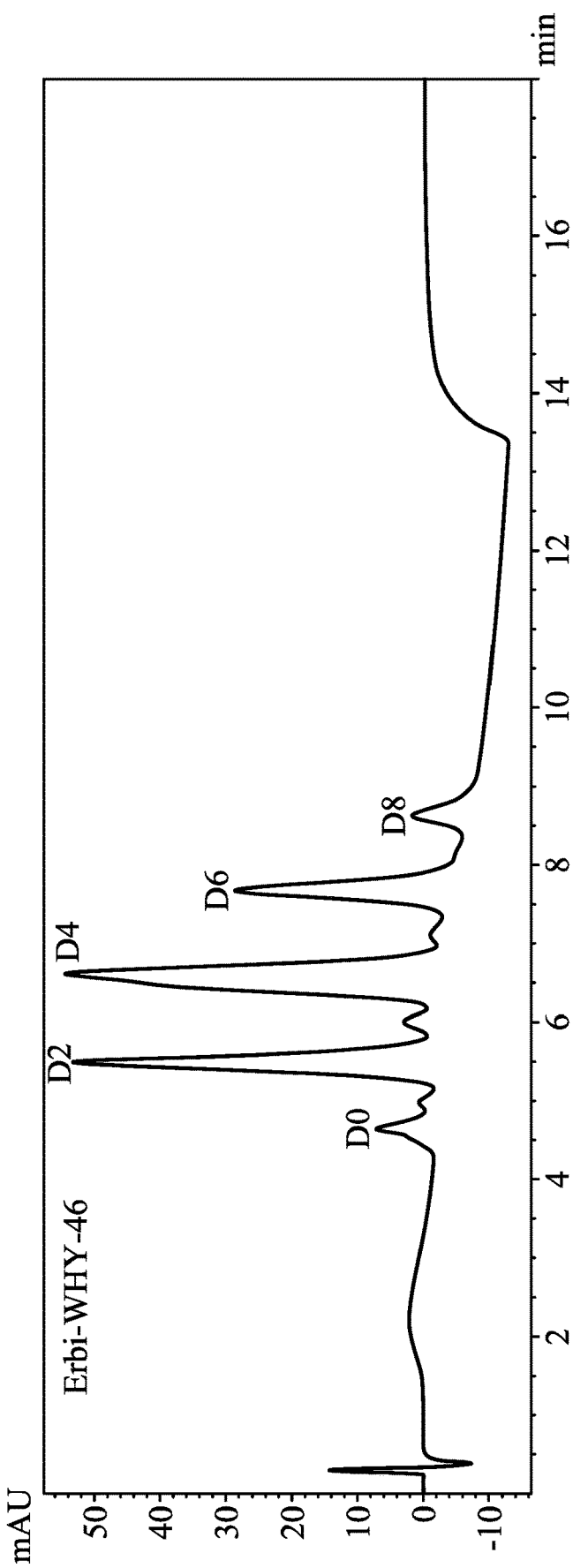
FIG. 13A shows a HIC profile of Erbitux-WHY-46 in accordance with one embodiment of the present disclosure.
Figure 13:
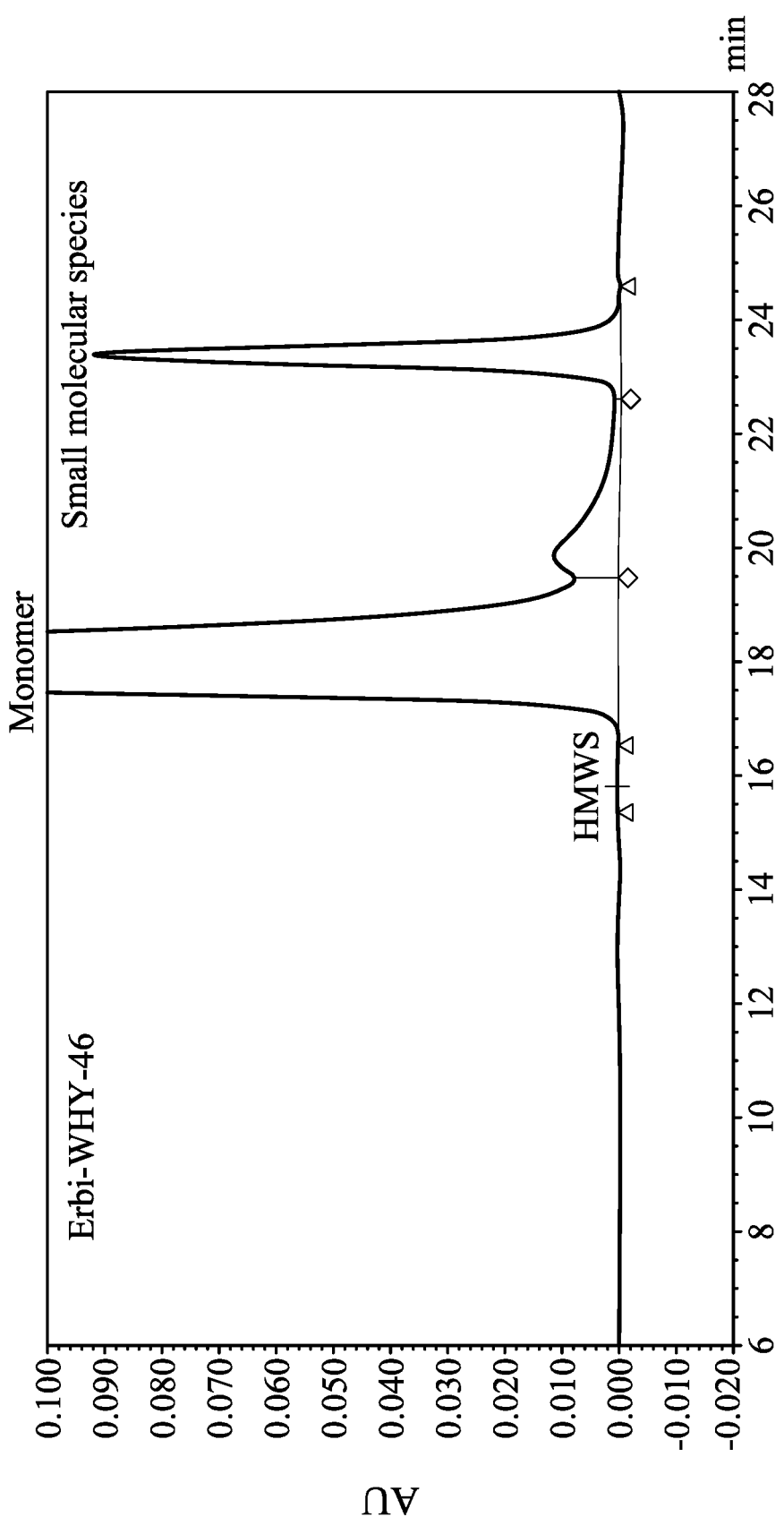
FIG. 13B shows a SEC profile of Erbitux-WHY-46 in accordance with one embodiment of the present disclosure.

FIG. 13A shows that the DAR of the ADC mainly distributes at 2 and 4. The average DAR of the Erbitux®-WHY-46 is about 3.9. The conjugation efficiency is about 96%. FIG. 13B shows that only 0.1% of HMWS was produced.

Example 14

Conjugation of Erbitux®-MHT-71 in Aqueous Phase 23.5 mL of Erbitux® (Cetuximab)(Merck) (initial concentration: 4.7 mg/mL) was treated with 159 µL of 10 mM TCEP (2.1 molar equivalent) in borate buffer for 2 hours at 37° C. Next, 1.52 mL of 3 mM linker-toxin MHT-71 (6 molar equivalent) prepared in ddH$_2$O was added to the above-mentioned antibody solution for 30 minutes at 4° C. (pure aqueous phase). 127 µL of 0.2 M cysteine was added to stop the reaction. A desalting column (ThermoFisher Scientific, MWCO: 40K) was used to purify Erbitux®-MHT-71. During elution, the buffer was changed to PBS buffer (2.67 mM KCl, 1.47 mM $KH_2PO_4$, 137.93 mM NaCl, 8.06 mM $Na_2HPO_4$-$7H_2O$). HIC and SEC were used to determine the average DAR and HMWS.

Figure 14A:
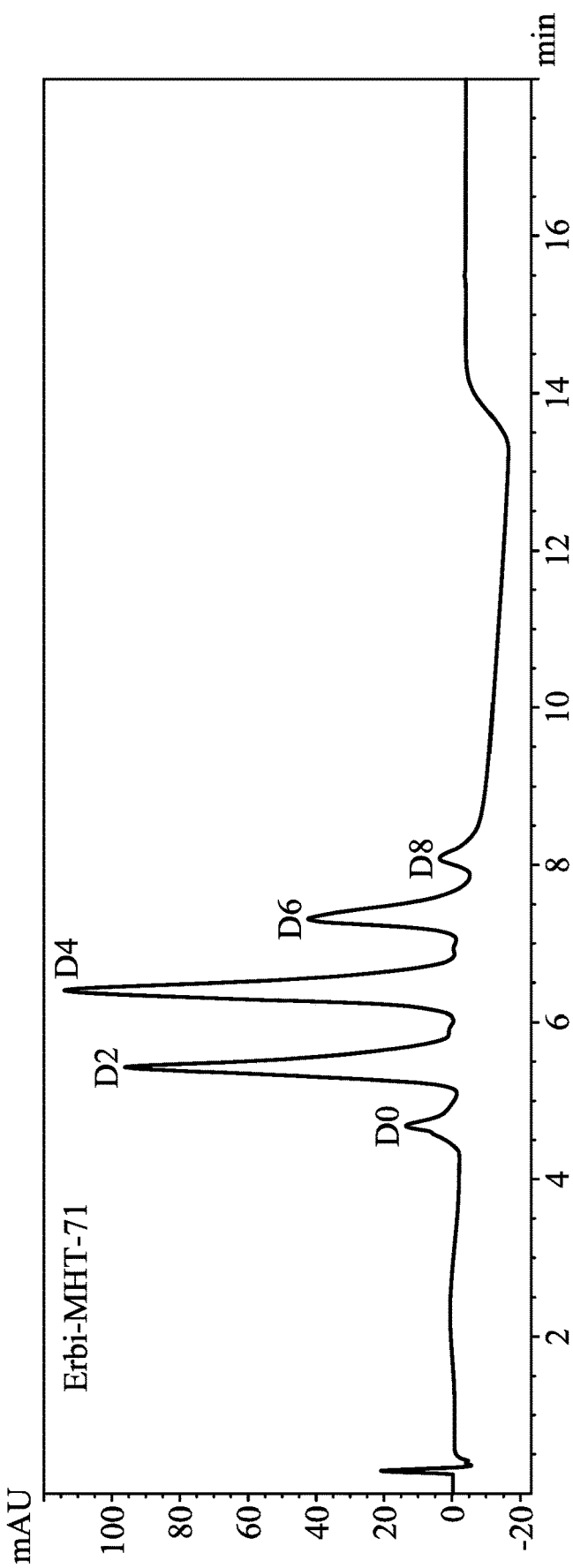
FIG. 14A shows a HIC profile of Erbitux-MHT-71 in accordance with one embodiment of the present disclosure.
Figure 14:
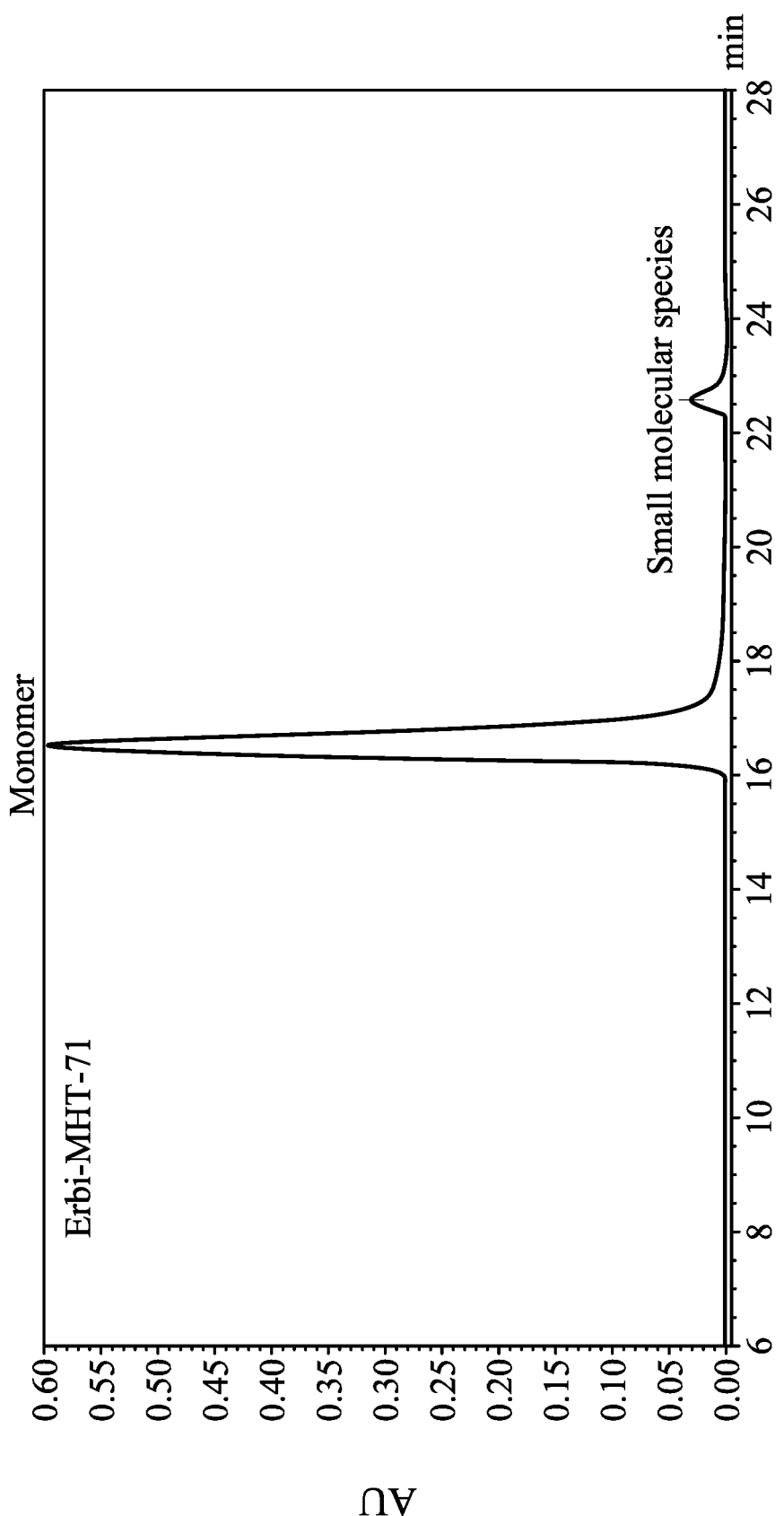
FIG. 14B shows a SEC profile of Erbitux-MHT-71 in accordance with one embodiment of the present disclosure.

FIG. 14A shows that the DAR of the ADC mainly distributes at 2 and 4. The average DAR of the Erbitux®-MHT-71 is about 3.6. The conjugation efficiency is about 95%. FIG. 14B shows that no significant HMWS was produced.

Example 15

Conjugation of HLX-07-MHT-71 in Aqueous Phase 0.5 mL of HLX-07 (produced by Henlix Inc.)(initial concentration: 4.4 mg/mL) was treated with 3.6 µL of 10 mM TCEP (2.4 molar equivalent) in borate buffer for 2 hours at 37° C. Next, 140 µL of 755 µM linker-toxin MHT-71 (7 molar equivalent) prepared in dd$H_2O$ was added to the above-mentioned antibody solution for 30 minutes at 4° C. (pure aqueous phase). 20 µL of 0.1 M cysteine was added to stop the reaction. A desalting column (ThermoFisher Scientific, MWCO: 40K) was used to purify HLX-07-MHT-71. During elution, the buffer was changed to PBS buffer (2.67 mM KCl, 1.47 mM $KH_2PO_4$, 137.93 mM NaCl, 8.06 mM $Na_2HPO_4$-$7H_2O$). HIC and SEC were used to determine the average DAR and HMWS.

Figure 15:
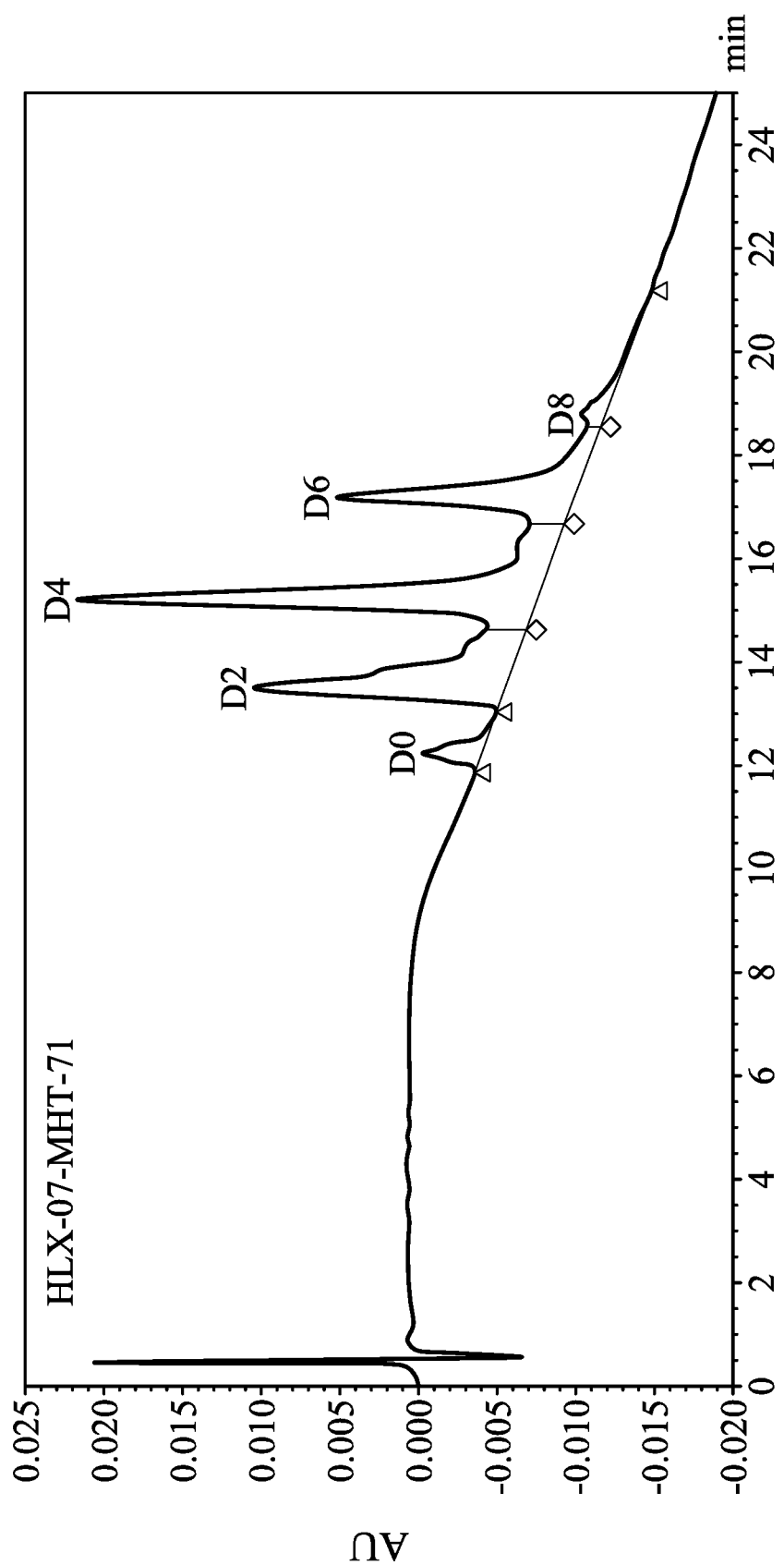
FIG. 15 shows a HIC profile of HLX-07-MHT-71 in accordance with one embodiment of the present disclosure.

FIG. 15 shows that the DAR of the ADC mainly distributes at 2 and 4. The average DAR of the HLX-07-MHT-71 is about 3.8. The conjugation efficiency is about 96%.

Example 16

Conjugation of Anti-EpCAM-MHT-71 in Aqueous Phase

60 µL of anti-EpCAM Ab (clone EpAb3-5, IgG2b) (produced by Dr. Han-Chung Wu's lab) (initial concentration: 3.9 mg/mL) was treated with 3.3 µL of 5 mM TCEP (8 molar equivalent) in borate buffer for 5 hours at 37° C. Next, 10.4 µL of 3 mM linker-toxin MHT-71 (15 molar equivalent) prepared in dd$H_2O$ was added to the above-mentioned antibody solution for 1 hour at 4° C. (pure aqueous phase). 0.5 µL of 0.2 M cysteine was added to stop the reaction. A desalting column (ThermoFisher Scientific, MWCO: 40K) was used to purify anti-EpCAM-MHT-71. During elution, the buffer was changed to PBS buffer (2.67 mM KCl, 1.47 mM $KH_2PO_4$, 137.93 mM NaCl, 8.06 mM $Na_2HPO_4$-$7H_2O$). The conjugation profile of anti-EpCAM-MHT-71 was analyzed by HIC. Unconjugated anti-EpCAM Ab peak was disappeared, indicating that all of the anti-EpCAM antibodies were conjugated with linker-toxin MHT-71.

Figure 16A:
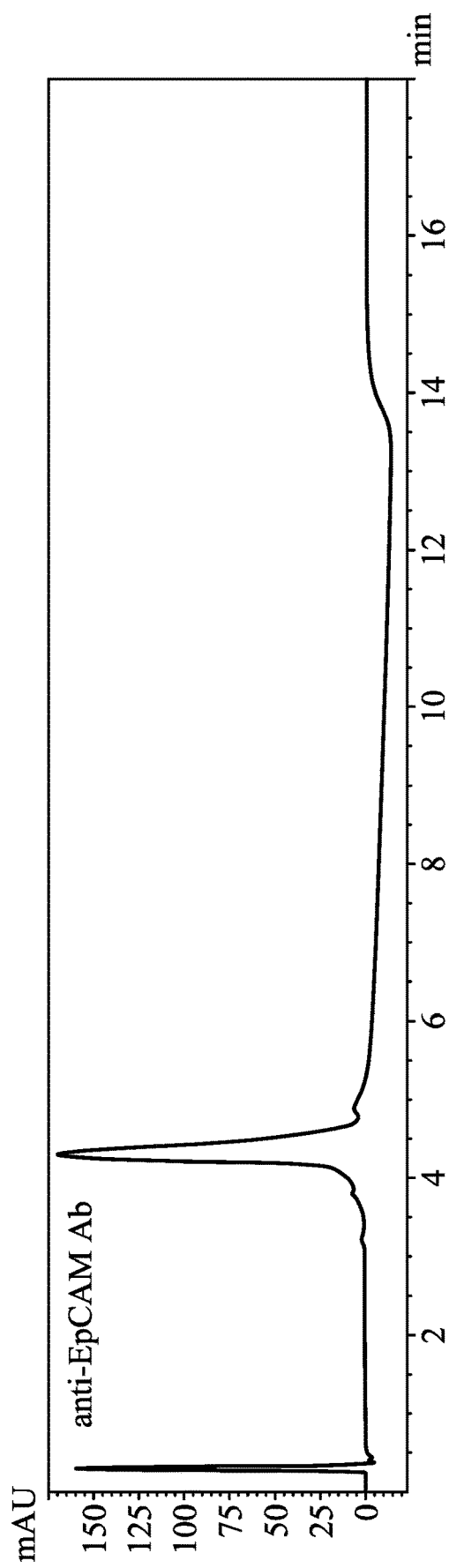
FIG. 16A a HIC profile of unconjugated anti-EpCAM Ab in accordance with one embodiment of the present disclosure.
Figure 16B:
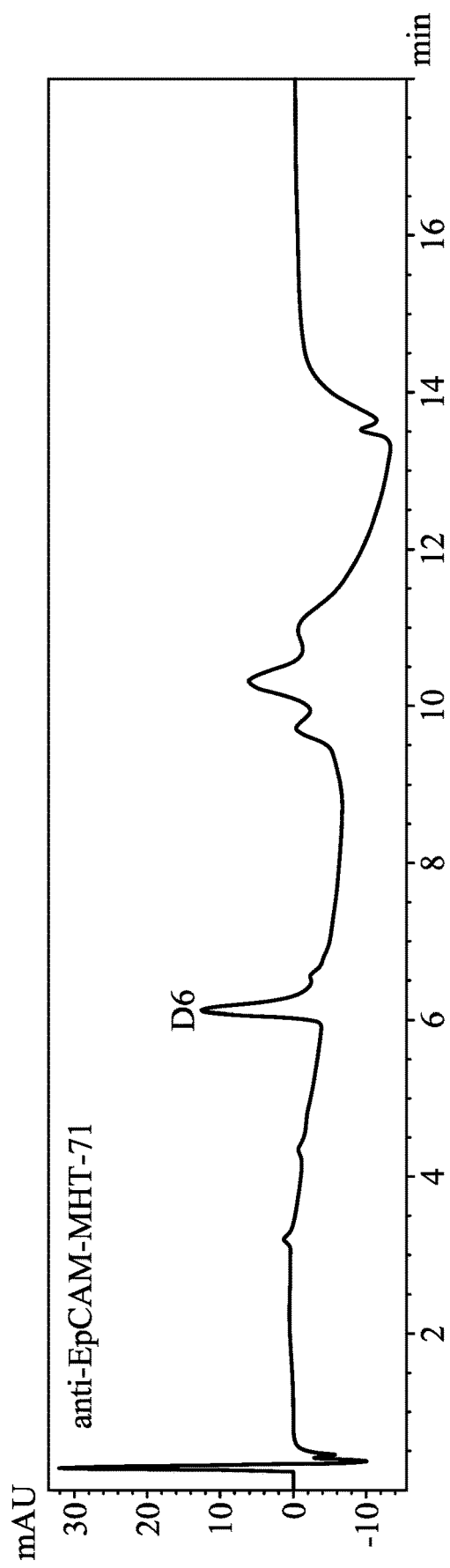
FIG. 16B a HIC profile of conjugated anti-EpCAM-MHT-71 in accordance with one embodiment of the present disclosure.

FIG. 16A shows the HIC profile of unconjugated anti-EpCAM Ab and FIG. 16B shows the HIC profile of anti-EpCAM Ab conjugated with linker-toxin MHT-71.

Thermal Stress Test

Example 17

500 µL of 3 mg/mL Erbitux, Erbitux-L1-MMAE (commercial linker-toxin MC-Val-Cit-PAB-MMAE (L1-MMAE); Concortis Biotherapeutics), Erbitux-MHT-87, Erbitux-MHT-71, or Erbitux-WHY-46 in PBS were incubated at 40° C. water bath and were sampled at 0, 1 and 2 weeks for SEC analysis. A Waters PDA 996 HPLC with the Yarra 3 µm SEC-3000 (300×7.8 mm) column was used to separate antibody monomer and aggregation products by size. The mobile phase consisted of 0.020 M potassium phosphate, 0.025 M potassium chloride, and isopropanol 5% (v/v), pH 6.95. 30 µL of samples were injected into the column at a flow rate of 0.5 mL/min and separated under isocratic conditions. Absorbance was detected at 280 nm. All species eluting prior to the main peak were integrated together and are reported as high molecular weight species (HMWS).

Figure 17A:
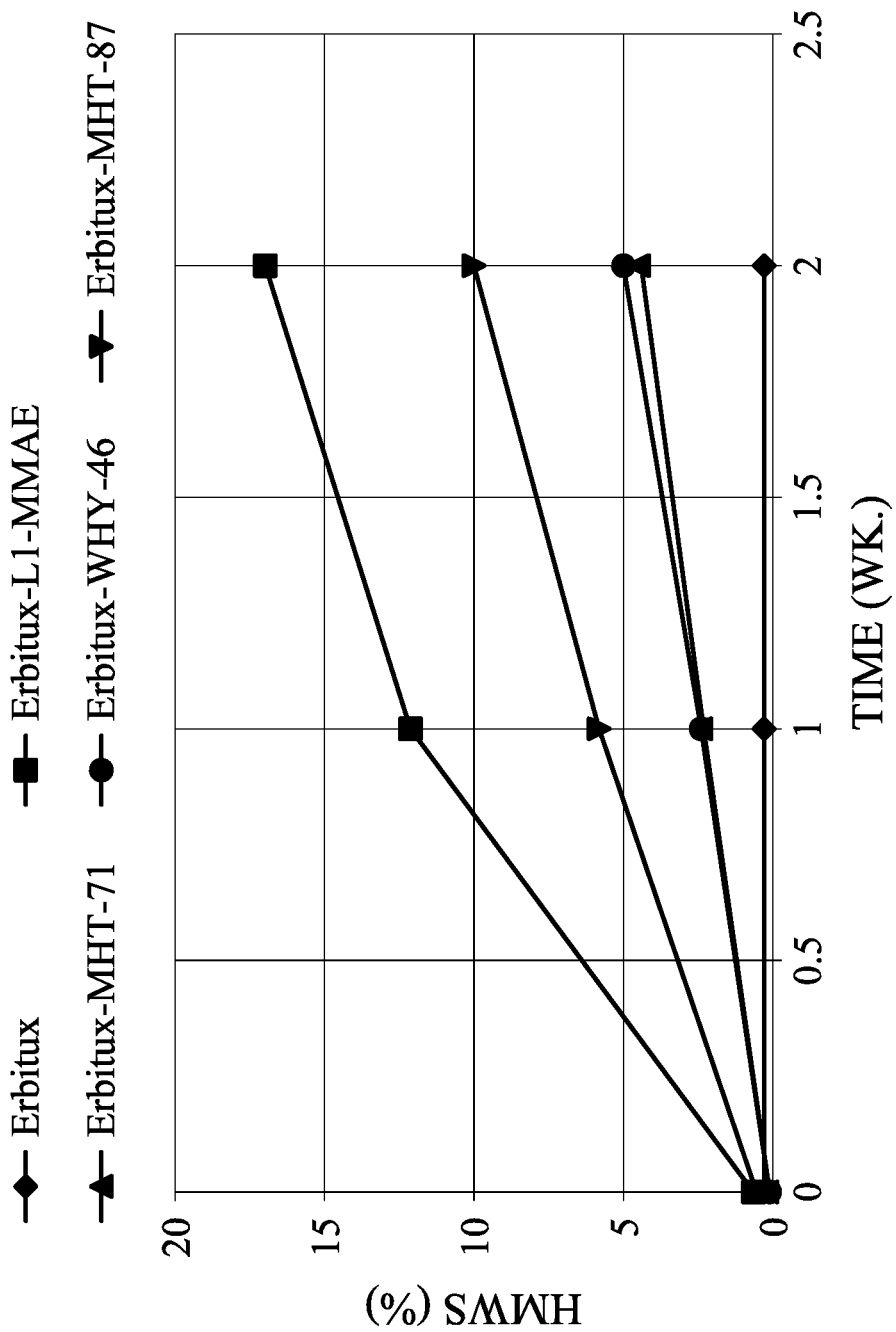
FIG. 17A shows the results of a thermal-stress stability test at 40° C. for Erbitux and Erbitux-ADCs in accordance with some embodiments of the present disclosure.

FIG. 17A shows that Erbitux-MHT-71 and Erbitux-WHY-46 whose linkers contain sugar amino acid unit(s) had lower percentages of HMWS than Erbitux-L1-MMAE and Erbitux-MHT-87 whose linkers do not contain any sugar amino acid unit. Therefore, this experiment demonstrated that the linkers with sugar amino acid unit(s) not only increase its hydrophilicity but also significantly improve the thermal stability of ADCs.

Example 18

500 µL of 3 mg/mL Erbitux, Erbitux-L1-MMAE (commercial linker-toxin MC-Val-Cit-PAB-MMAE (L1-MMAE); Concortis Biotherapeutics), Erbitux-MHT-87, Erbitux-MHT-71, and Erbitux-WHY-46 in PBS were incubated in a water bath at 50° C. Then the antibody and ADCs were sampled at 0, 4, 7 and 24 hours for SEC analysis. A Waters PDA 996 HPLC with the Yarra 3 µm SEC-3000 (300×7.8 mm) column was used to separate antibody monomer and aggregation products by size. The mobile phase consisted of 0.020 M potassium phosphate, 0.025 M potassium chloride, and isopropanol 5% (v/v), pH 6.95. 30 µL of samples were injected into the column at a flow rate of 0.5 mL/min and separated under isocratic conditions. Absorbance was detected at 280 nm. All species eluting prior to the main peak were integrated together and are reported as high molecular weight species (HMWS).

Figure 17B:
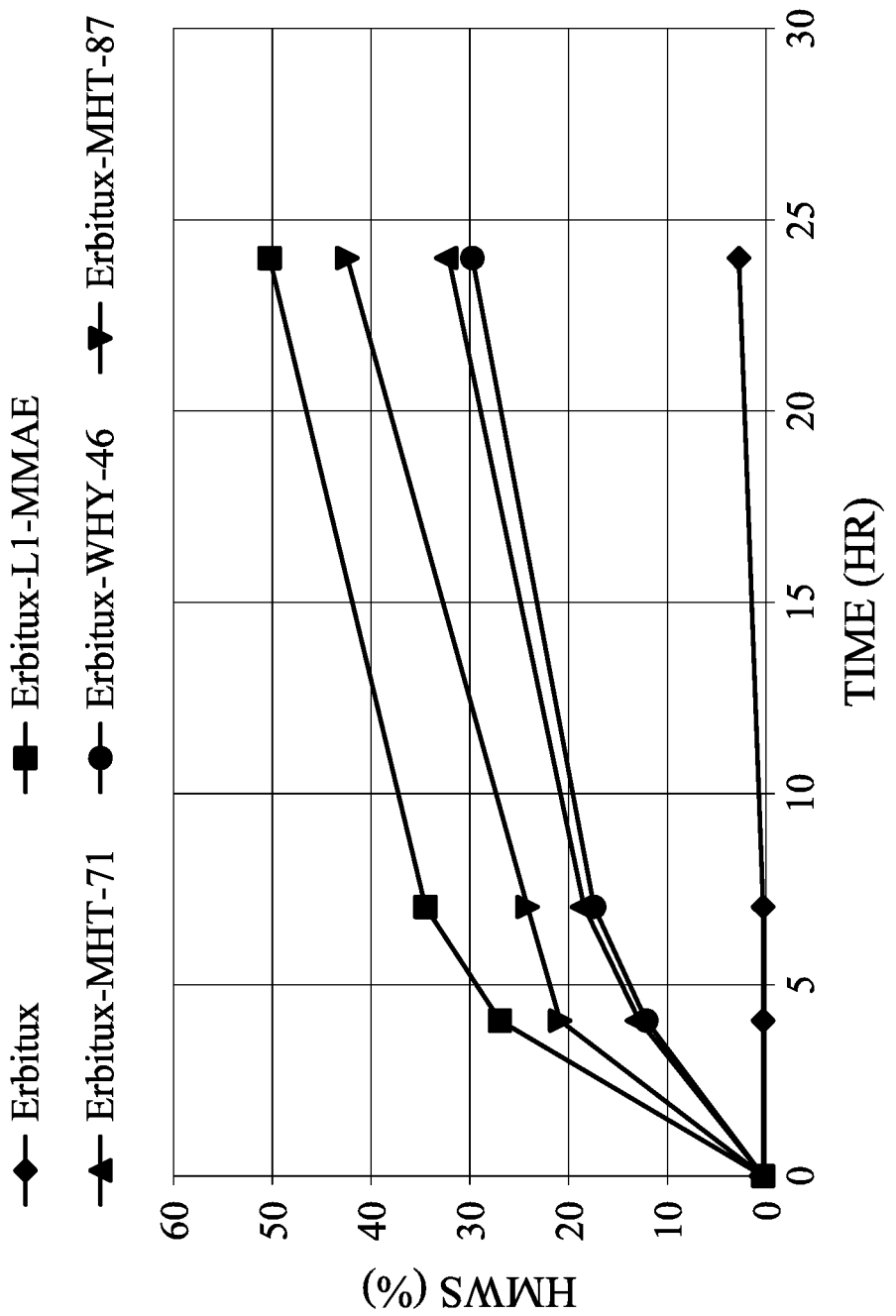
FIG. 17B shows the results of a thermal-stress stability test at 50° C. for Erbitux and Erbitux-ADCs in accordance with some embodiments of the present disclosure.

FIG. 17B showed Erbitux-MHT-71 and Erbitux-WHY-46 whose linkers contain sugar amino acid unit(s) had lower HMWS percentages than Erbitux-L1-MMAE and Erbitux-MHT-87 whose linkers do not contain any sugar amino acid unit. Therefore, this experiment demonstrated that the linkers with sugar amino acid unit(s) not only increase its hydrophilicity but also significantly improve the thermal stability of ADCs.

Storage Test

Example 19

Erbitux-MHT-71 conjugated in aqueous phase was purified by a desalting column. During elution, the buffer was changed to 20 mM sodium citrate, 6.3% (w/v) trehalose, 0.2 mg/mL polysorbate 80, pH 6.0 (SGN). Erbitux-MHT-71 was divided into 100 µL/tube and stored at 4° C. for the storage stability test. Erbitux-MHT-71 was sampled every week or every two weeks for antibody concentration, HIC and SEC analysis for 17 weeks.

Figure 18:
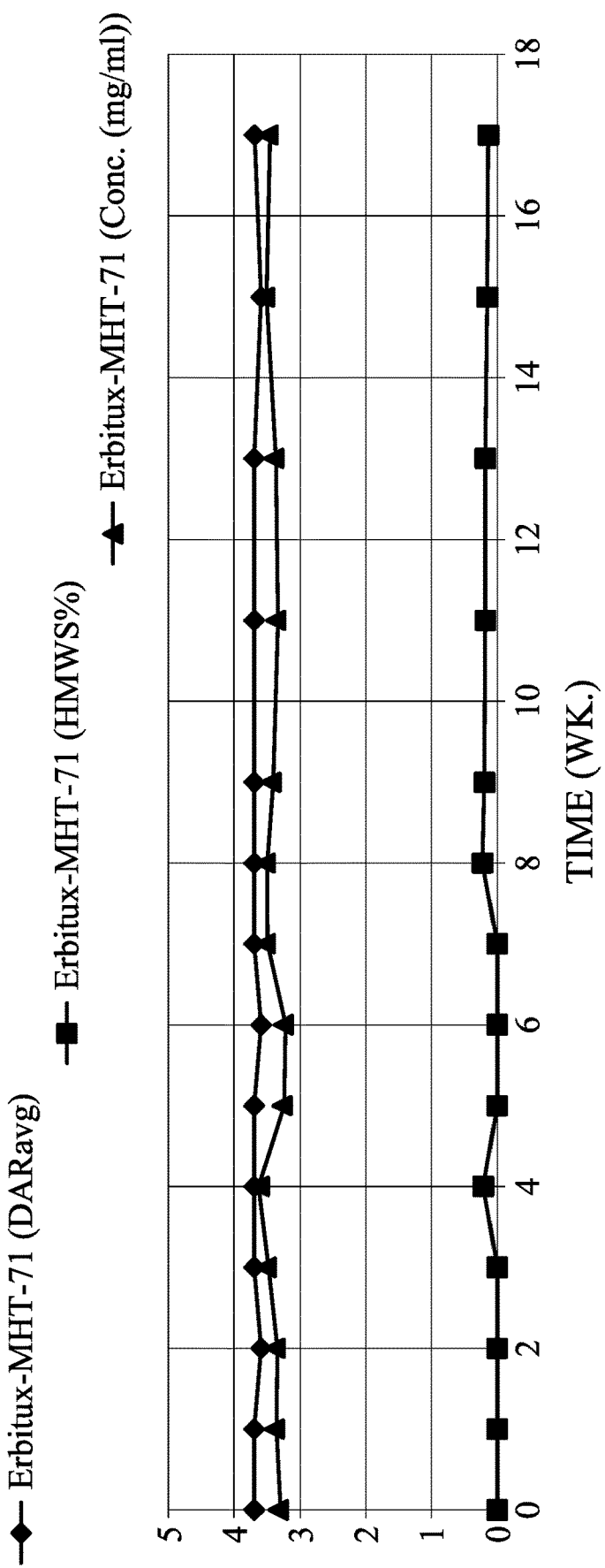
FIG. 18 shows the results of a storage stability test for liquid form of Erbitux-MHT-71 at 4° C. in accordance with some embodiments of the present disclosure.

FIG. 18 shows that the antibody concentration of Erbitux-MHT-71 has no significant change (<10%) over four months, the average DAR of Erbitux-MHT-71 has no significant change (<5%) over four months, and the production of HMWS of Erbitux-MHT-71 was still very low (≤0.2%) after four months.

Potency Test

Example 20

EGFR-expressing head and neck cancer cell lines FaDu and non-EGFR-expressing head and neck cancer cell lines RPMI 2650 were treated with ADCs containing 9 kinds of glycopeptide linkers to analyze their selective toxicity in different EGFR-expressing tumor cells.

FaDu cells and RPMI cells were respectively seeded in Corning CellBIND 96-well plates at densities of $2.5 \times 10^3$ and $4 \times 10^3$ cells/well. After incubation for 24 hours at 37° C., 5% $CO_2$ incubator, the old medium was removed and the ADCs containing media were added to the cells at concentrations ranging from $10^{-7}$ to $10^{-13}$ M for FaDu cells or ranging from $10^{-6}$ to $10^{-12}$ M for RPMI 2650 cells (serial dilutions). The cells were then incubated for 120 hours at 37° C., 5% $CO_2$ incubator. After 120-hour incubation, the cells were rinsed once and assayed for cell viability with the MTT method. The old medium was aspirated and 100 µL of 0.5 mg/mL MTT containing medium was added into each well. After incubation for 4 hours, the MTT reagent was removed and the precipitate was dissolved in DMSO. The photometry intensity of the cells was measured by the microplate reader (Multiskan Ascent, Thermo Labsystems) of absorbance wavelength at 570 nm. Cell viability was calculated by the following equation. Cell viability was calculated by the following equation.

Cell Viability (%)=(Ins−Inb)/(Inc−Inb)×100%

In this equation, "Ins" is the photometry intensity of the cells incubated with a given toxin, "Inb" is the intensity of a blank well without cell seeding, and "Inc" is the intensity of the cells incubated with the culture medium only (positive control).

The in vitro viability of FaDu cells after exposure to toxins for 120 hours at various drug concentrations (n=6) were recorded, and the data were fitted to obtain IC50 values using Sigmoidal model of Origin software.

Table 3 shows the IC50 value of ADCs containing 9 kinds of glycopeptide linkers in EGFR-expressing head and neck cancer cell lines FaDu cells are significantly less than 0.5 nM. The potency of ADCs containing 9 kinds of glycopeptide linkers in FaDu cells is very high. Except for Erbitux-MHT-93, ADCs containing eight other kinds of glycopeptide linkers have high selective toxicity in tumor cells. The selective toxicity is more than 2000 times in the EGFR-expressing head and neck cancer cell lines FaDu cells than in the non-EGFR-expressing head and neck cancer cell lines RPMI 2650 cells. The selective toxicity is superior to the selective toxicity (about 1246 times) of Erbitux-L1-MMAE conjugated by commercial linker-toxin MC-Val-Cit-PAB-MMAE (Concortis Biotherapeutics) and the selective toxicity effect (about 366 times) of Erbitux-MHT-87 whose linkers do not contain any sugar amino acid unit.

TABLE 3

| | IC50 (nM) | | In vitro selective toxicity |
|---|---|---|---|
| | RPMI 2650 EGFR expression | FaDu | |
| | 0 | 2+ | |
| Erbitux-L1-MMAE | 107.2 | 0.086 | 1246 |
| Erbitux-MHT-87 | 27.1 | 0.074 | 366 |
| Erbitux-MHT-47 | 80.0 | 0.037 | 2162 |
| Erbitux-MHT-71 | 247 | 0.074 | 3337 |
| Erbitux-MHT-93 | 57.0 | 0.16 | 356 |
| Erbitux-FCW-016 | >200 | 0.068 | >2941 |
| Erbitux-CCH-028 | >1000 | 0.148 | >6756 |
| Erbitux-CCH-035 | >1000 | 0.176 | >5681 |
| Erbitux-CCH-038 | >1000 | 0.137 | >7299 |
| Erbitux-WHY-46 | >200 | 0.091 | >2197 |
| Erbitux-CCH-041 | >1000 | 0.120 | >8333 |

Tumor Growth Inhibition Test

Example 21

$1 \times 10^6$ of FaDu cells were subcutaneous injected to C.B-17 SCID mice at Day 0. The length and width of the tumor were measured and the tumor size was calculated by (length×width×width×½) (mm³) and recorded. At Day 8, when the average tumor size was about 100 mm³, vehicle (DPBS), 5 mg/kg Erbitux®, 5 mg/kg Erbitux-MHT-47, 5 mg/kg Erbitux-MHT-71, 5 mg/kg Erbitux-L1-MMAE (commercial linker-toxin MC-Val-Cit-PAB-MMAE (L1-MMAE); Concortis Biotherapeutics), 0.1 mg/kg APEA-AF (commercial AF; Concortis Biotherapeutics), 0.1 mg/kg MMAE (Concortis Biotherapeutics) were intravenously injected (10 mL/kg B.W. injectionvolumn) once for the pharmacodynamic experiment (n=6). Tumor growth and body weight of the mice were observed twice every week. The calculation formula of Tumor Growth Inhibition (TGI) is TGI (%), [1−(Δ drug treated group tumor volume/Δ vehicle group tumor volume]×100. During the experiment, if the tumor is more than 10% of body weight of mice, the tumor volume is more than 1500 mm³, or other adverse reactions occurred concurrently, mice were sacrificed using $CO_2$ due to humanitarian considerations.

Figure 19:
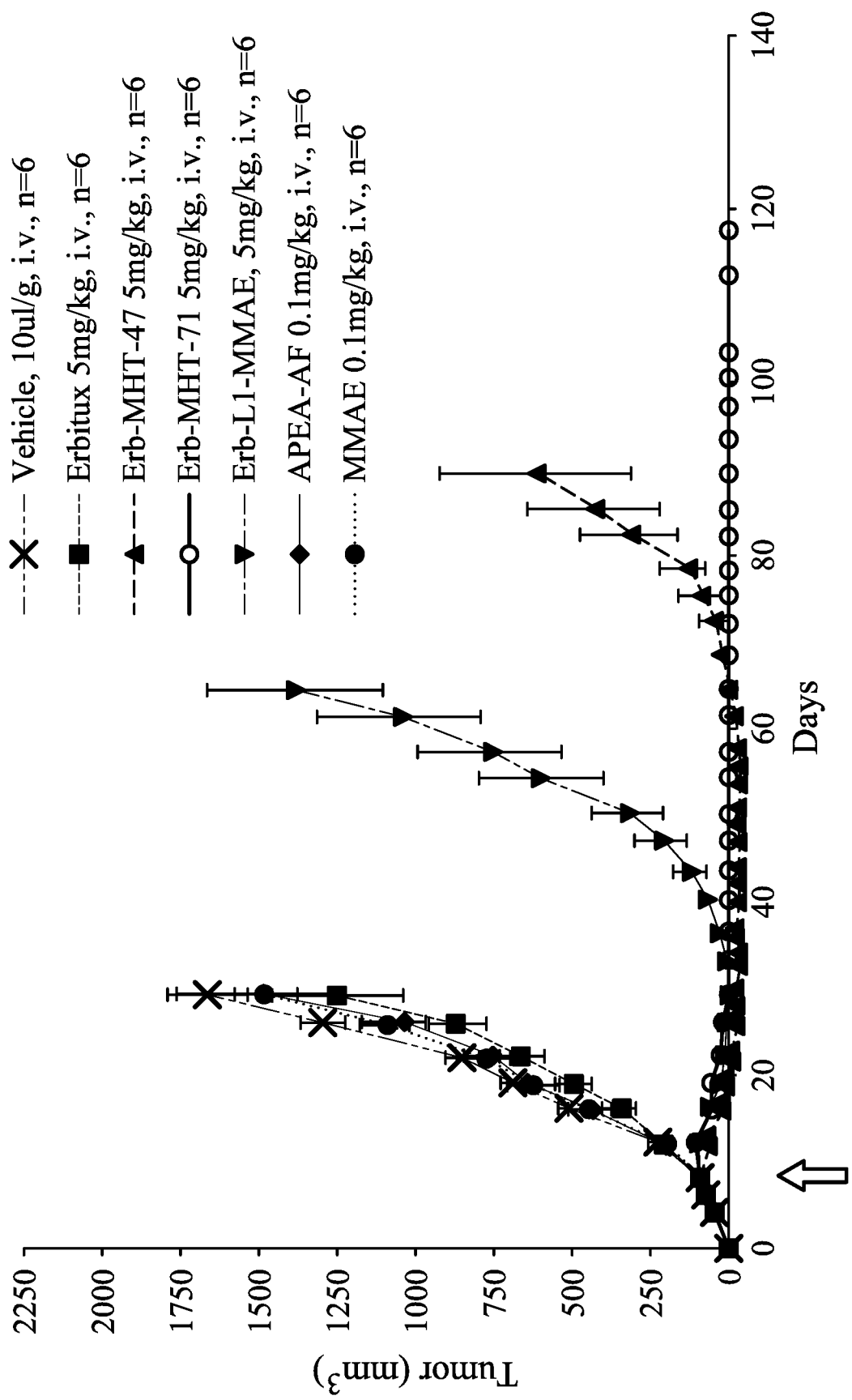
FIG. 19 shows the results of a tumor growth change for Erbitux, Erbitux-ADCs, APEA-AF, and MMAE injected mice in accordance with some embodiments of the present disclosure.

After 8 days of treatment with drugs (Erbitux, Erbitux-ADCs, APEA-AF, and MMAE), tumor growths of Erbitux-MHT-47, Erbitux-MHT-71, and Erbirux-L1-MMAE groups were significantly inhibited. At Day 29, TGI of Erbitux-MHT-47, Erbitux-MHT-71 and Erbirux-L1-MMAE groups were 106±1%, 106±1%, and 105±8%, respectively, while TGI of Erbitux group is 27±14% (referring to Table 4). FIG. 19 shows that a recurrence of the tumor was observed in Erbitux-L1-MMAE group at Day 36. A recurrence of the tumor was observed in Erbitux-MHT-47 group at Day 54-61. However, there was no recurrence of the tumor observed in Erbitux-MHT-71 group until Day 117.

TABLE 4

| | TGI (%) ± SEM Day 8-29 |
|---|---|
| Vehicle (DPBS) | 0 |
| Erbitux ® (5 mg/kg) | 27 ± 14 |
| Erbitux-MHT-47 (5 mg/kg) | 106 ± 1 |
| Erbitux-MHT-71 (5 mg/kg) | 106 ± 1 |
| Erbitux-L1-MMAE (5 mg/kg) | 105 ± 8 |
| APEA-AF (0.1 mg/kg) | 11 ± 17 |
| MMEA (0.1 mg/kg) | 12 ± 6 |

Figure 20:
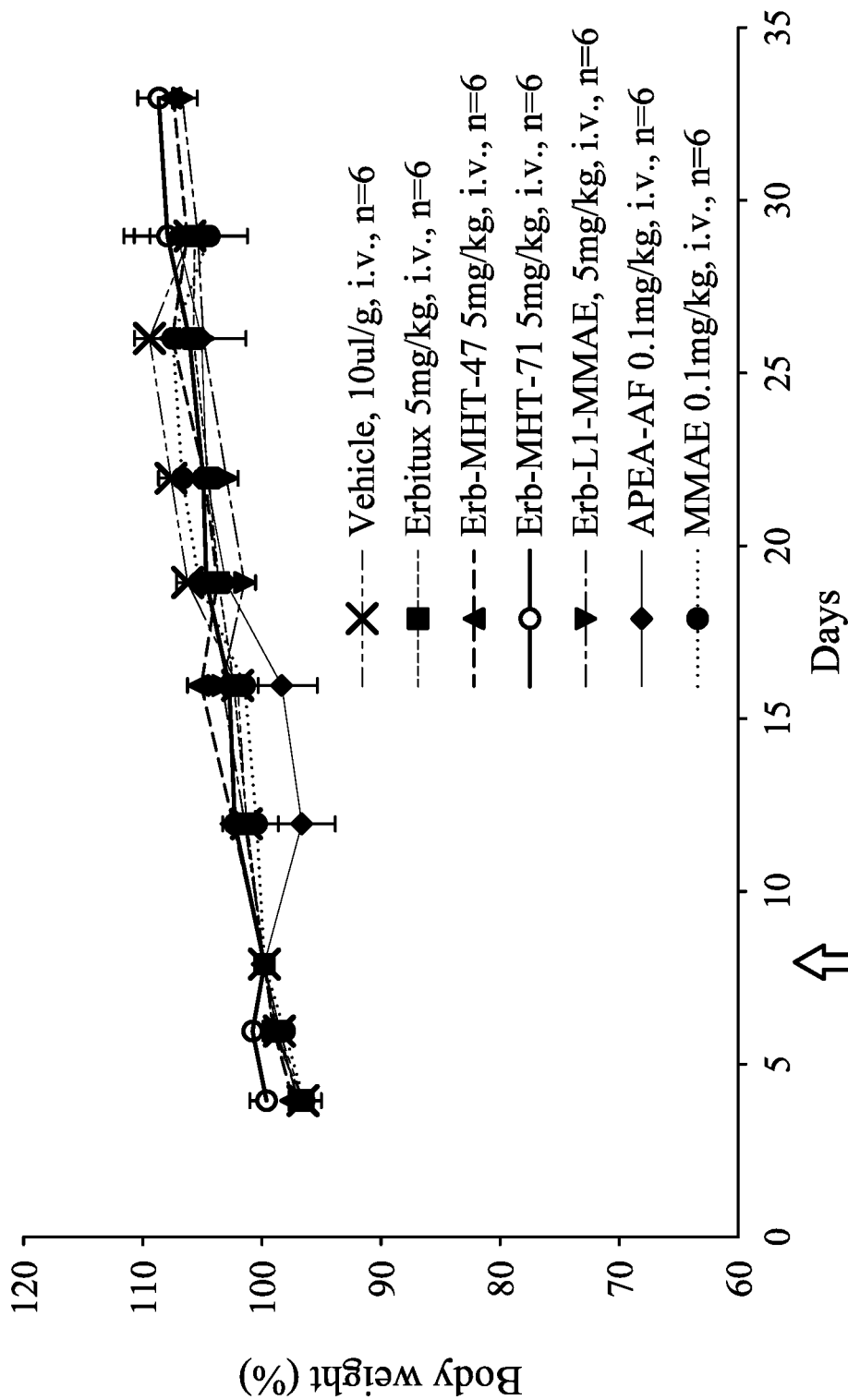
FIG. 20 shows the results of a body weight change for Erbitux, Erbitux-ADCs, APEA-AF, and MMAE injected mice in accordance with some embodiments of the present disclosure.

FIG. 20 shows that no weight losing or other significant abnormal clinical symptoms occurred after drug administration (Erbitux, Erbitux-ADCs, APEA-AF, and MMAE).

TABLE 5

| | BW (%) ± SEM Day 8-29 |
|---|---|
| Vehicle (DPBS) | 106 ± 5 |
| Erbitux ® (5 mg/kg) | 106 ± 1 |
| Erbitux-MHT-47 (5 mg/kg) | 106 ± 1 |
| Erbitux-MHT-71 (5 mg/kg) | 108 ± 2 |
| Erbitux-L1-MMAE (5 mg/kg) | 106 ± 1 |
| APEA-AF (0.1 mg/kg) | 108 ± 4 |
| MMEA (0.1 mg/kg) | 106 ± 4 |

It will be apparent to those skilled in the art that various modifications and variations may be made to the disclosed embodiments. It is intended that the specification and examples be considered as exemplary only, with the true scope of the disclosure being indicated by the following claims and their equivalents.

What is claimed is:

1. An antibody-drug conjugate (ADC) of formula (I) or a pharmaceutically acceptable salt thereof:

wherein
p is an integer ranging from 1 to 26;
A is a full-length antibody; and
-(L-D) is a linker-drug unit,
wherein L is a linker unit having a glycopeptide, and D is a drug unit,
wherein the linker unit is —C-SAAs-AAs-, wherein C— is a conjugating unit selected from a group consisting of

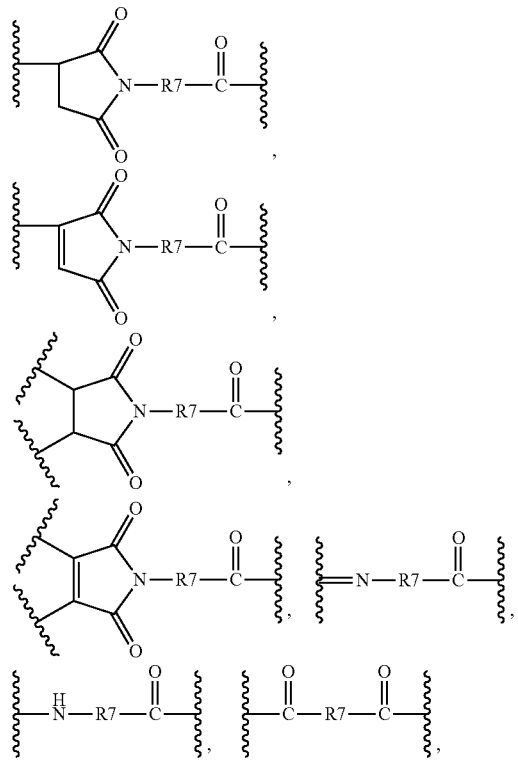

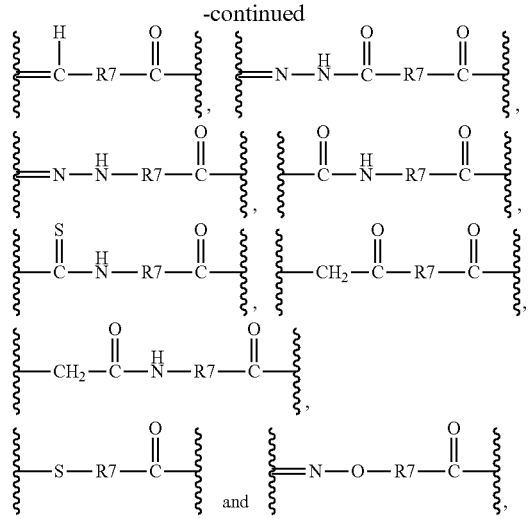

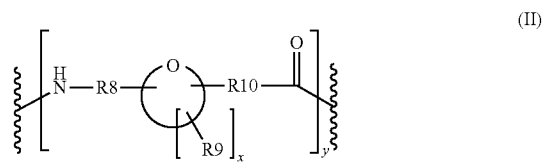

wherein R7 is selected from a group consisting of —C1-C10 alkylene-, —C3-C8 carbocyclo-, —O-(C1-C8 alkyl)-, -arylene-, —C1-C10 alkylene-arylene-, -arylene-C1-C10 alkylene-, —C1-C10 alkylene-(C3-C8 carbocyclo)-, —(C3-C8 carbocyclo)-C1-C10 alkylene-, —C3-C8 heterocyclo-, —C1-C10 alkylene-(C3-C8 heterocyclo)-, -(C3-C8 heterocyclo)-C1-C10 alkylene-, —(CH$_2$CH$_2$O)r- and —(CH$_2$CH$_2$O)r-CH$_2$—, and r is an integer ranging from 1 to 10;

-SAAs- is a sugar amino acid unit of formula (II):

wherein x is an integer ranging from 1 to 8, y is an integer ranging from 1 to 4,

○ is a tetrahydrofuran, dihydrofuran, tetrahydropyran or dihydropyran ring, R8 and R10 are each, independently, a single bond, methylene, hydroxymethylene, ethylene, ethylidene, hydroxyethylene, hydroxyethylidene, dihydroxyethylene, dihydroxyethylidene, vinylene, vinylidene, propylene, propylidene, trimethylene, hydroxypropylene, hydroxypropylidene, hydroxytrimethylene, dihydroxypropylene, dihydroxypropylidene, dihydroxytrimethylene, trihydroxypropylene, trihydroxypropylidene or trihydroxytrimethylene, each R9 is, independently, hydroxyl, methyl, hydroxymethyl, ethyl, hydroxyethyl, dihydroxyethyl, propyl, hydroxypropyl, dihydroxypropyl or trihydroxypropyl or any two R9 in the same ring carbon together with the carbon to which they are attached form a carbonyl group, or any two R9, R8 and any one R9, or R10 and any one R9 form a second tetrahydrofuran, dihydrofuran, tetrahydropyran or dihydropyran ring that fuses to the original tetrahydrofuran, dihydrofuran, tetrahydropyran or dihydropyran ring, or any two R9, R8 and any one R9, or R10 and any one R9 together with a methylene, ethylidene, 1-propylidene, 2-propylidene or benzylidene group form a cyclic acetal or ketal ring that fuses to the original tetrahydrofuran, dihydrofuran, tetrahydropyran or dihydropyran ring; and -AAs- is a peptide unit of formula (III):

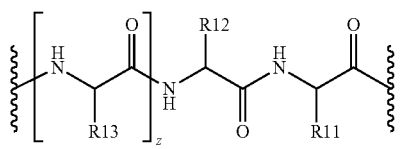
(III)

wherein z is an integer ranging from 0 to 10, R11 is —(CH$_2$)$_3$NHC(=NH)NH$_2$, —(CH$_2$)$_3$NH$_2$, —(CH$_2$)$_3$NHCONH$_2$, —(CH$_2$)$_4$NHC(=NH)NH$_2$, —(CH$_2$)$_4$NH$_2$ or —(CH$_2$)$_4$NHCONH$_2$, R12 is H, methyl, ethyl, propyl, isopropyl, cyclopropyl, butyl, sec-butyl, isobutyl, tert-butyl, cyclobutyl, phenyl or benzyl, R13 is hydrogen, methyl, isopropyl, cyclopropyl, butyl, sec-butyl, isobutyl, tert-butyl, cyclobutyl, cyclohexyl, phenyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl, 3-pyridylmethyl or 4-pyridylmethyl, wherein the antibody is conjugated to the linker unit through a cysteine residue of the antibody.

2. The antibody-drug conjugate (ADC) as claimed in claim 1, wherein the antibody is a chimeric antibody, a humanized antibody, a human antibody, a mouse antibody, a rat antibody, a goat antibody, or a rabbit antibody.

3. The antibody-drug conjugate (ADC) as claimed in claim 1, wherein the antibody is a therapeutic antibody used for the treatment of tumor, chronic lymphocytic leukemia (CLL), or acute myeloid leukemia (AML).

4. The antibody-drug conjugate (ADC) as claimed in claim 1, wherein the antibody comprises Herceptin, Erbitux, HLX-07, EG12014, anti-EpCAM Ab and IgG1, Rituximab, Ibritumomab tiuxetan, Tositumomab, Brentuximab vedotin, Alemtuzumab, IGN101, Adecatumumab, Labetuzumab, huA33, Pemtumomab, Oregovomab, CC49 (minretumomab), cG250, J591, MOv18, MORAb-003 (farletuzumab), 3F8, ch14.18, KW-2871, hu3S193, IgN311, Bevacizumab, IM-2C6, CDP791, Etaracizumab, Volociximab, Cetuximab, Panitumumab, Nimotuzumab, 806, Trastuzumab, Pertuzumab, MM-121, AMG 102, METMAB, SCH 900105, AVE1642, IMC-A12, MK-0646, R1507, CP 751871, KB004, IIIA4, Mapatumumab (HGS-ETR1), HGS-ETR2, CS-1008, Denosumab, Sibrotuzumab, F19, 8106, humanized anti HER2 mAb, OvaRex, Panorex, Cetuximab Erbitux, Vitaxin, Campath I/H, Smart MI95, LymphoCide, Smart ID10, Oncolym, Allomune, Avastin, Epratuzamab, or CEAcide.

5. The antibody-drug conjugate (ADC) as claimed in claim 1, wherein C— is the conjugating unit selected from a group consisting of

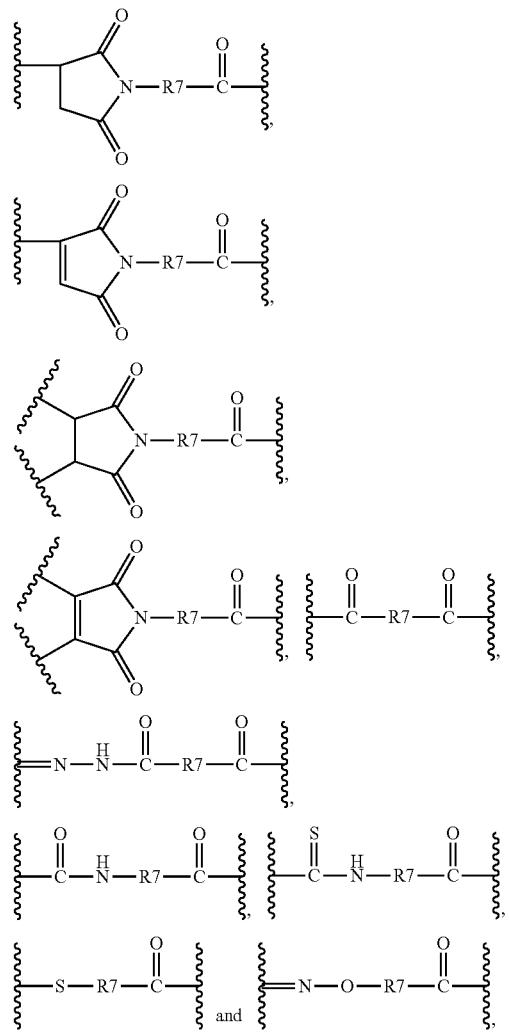
and wherein R7 is selected from a group consisting of -1,5-pentylene-, -1,6-hexylene-, -1,4-cyclohexylene-, —(CH$_2$CH$_2$O)r-CH$_2$— and —(CH$_2$CH$_2$O)r-CH$_2$—CH$_2$—, and r is an integer ranging from 2-5.

6. The antibody-drug conjugate (ADC) as claimed in claim 1, wherein -SAAs- is the sugar amino acid unit selected from a group consisting of

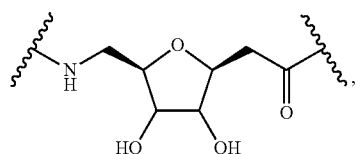

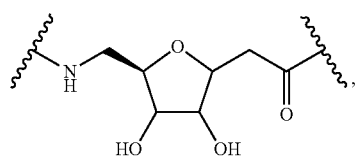

89
-continued
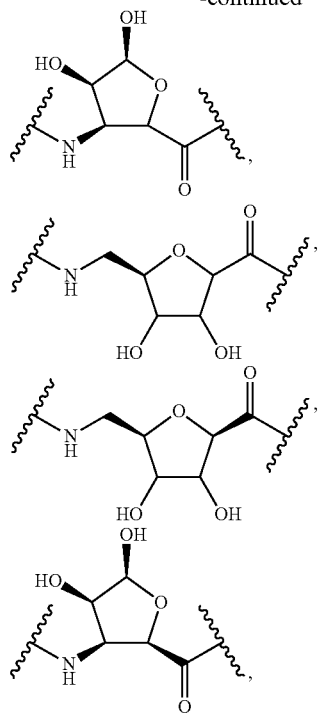
90
-continued
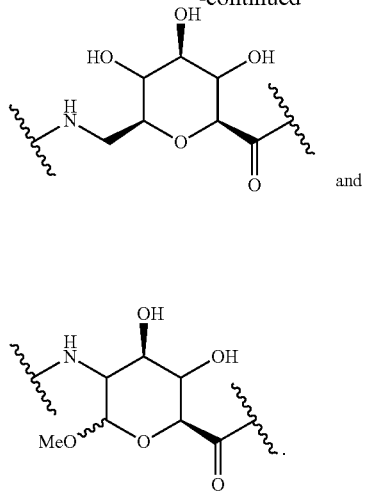
7. The antibody-drug conjugate (ADC) as claimed in claim 1, wherein -AAs- is the peptide unit selected from a group consisting of -Val-Cit-, -Val-Lys-, -Val-Arg-, -Phe-Cit-, -Phe-Lys- and -Phe-Arg-.
8. The antibody-drug conjugate (ADC) as claimed in claim 1, wherein the drug unit is the cytotoxic agent selected from a group consisting of
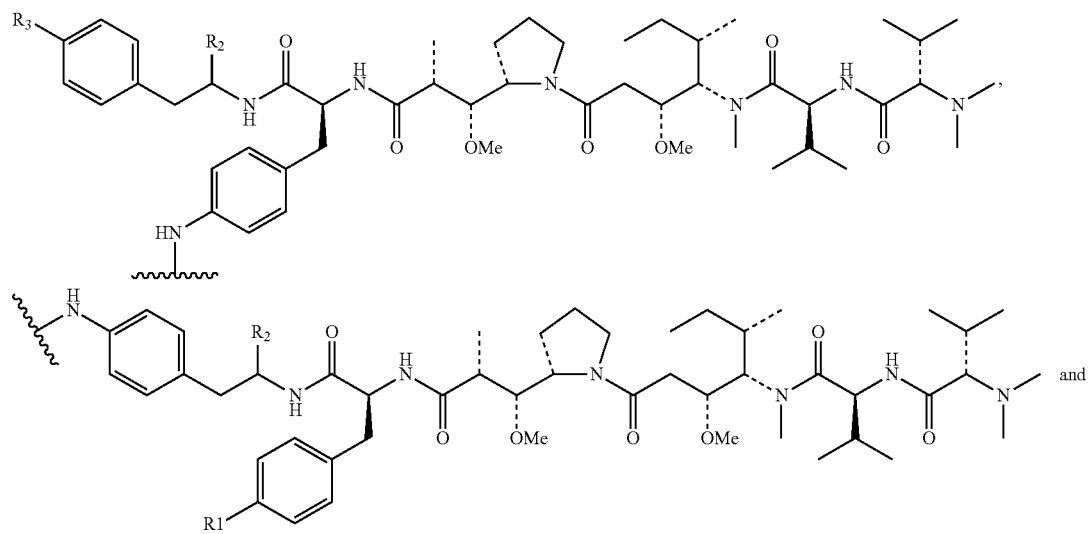
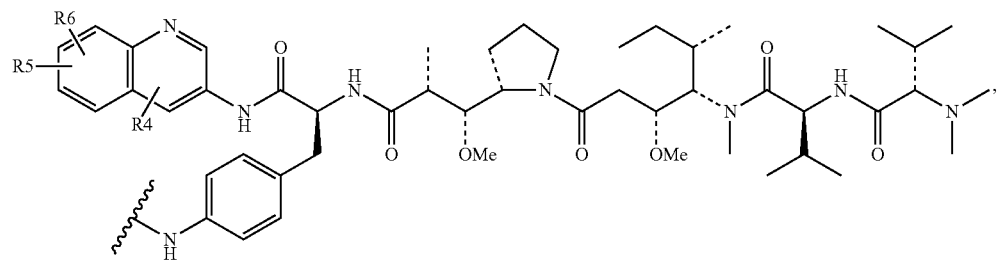

wherein R1, R2, R3, R4, R5 and R6 are each, independently, hydrogen, amino, nitro, halogen, hydroxyl, methoxy, ethoxy, carboxylic acid, methoxycarbonyl, ethoxycarbonyl, methylamino, dimethylamino, ethylamino, diethylamino, 1-pyrrolidinyl, 1-piperidinyl, 1-piperazinyl, aminocarbonyl, methylaminocarbonyl, dimethylaminocarbonyl, ethylaminocarbonyl, diethylaminocarbonyl, 1-pyrrolidinylcarbonyl, 1-piperidinylcarbonyl, 1-piperazinylcarbonyl, methyl, ethyl, propyl, isopropyl or phenyl.

9. The antibody-drug conjugate (ADC) as claimed in claim 1, wherein the drug unit has a cytostatic or cytotoxic activity against a target cell.

10. The antibody-drug conjugate (ADC) as claimed in claim 1, wherein the drug unit is a cytotoxic agent selected from a group consisting of amanitins, anthracyclines, auristatins, baccatins, calicheamicins, camptothecins, cemadotins, colchicines, colcimids, combretastatins, cryptophysins, discodermolides, duocarmycins, echinomycins, eleutherobins, epothilones, estramustines, lexitropsins, maytansinoids, netropsins, puromycins, pyrrolobenzodiazepines, rhizoxins, taxanes, tubulysins, and vinca alkaloids.

* * * * *